United States Patent [19]

Barker

[11] Patent Number: 5,457,105
[45] Date of Patent: Oct. 10, 1995

[54] QUINAZOLINE DERIVATIVES USEFUL FOR TREATMENT OF NEOPLASTIC DISEASE

[75] Inventor: Andrew J. Barker, Macclesfield, England

[73] Assignee: Zeneca Limited, London, England

[21] Appl. No.: 284,293

[22] Filed: Aug. 2, 1994

Related U.S. Application Data

[63] Continuation of Ser. No. 5,280, Jan. 19, 1993, abandoned.

[30] Foreign Application Priority Data

Jan. 20, 1992 [GB] United Kingdom ............. 9201095
Jun. 26, 1992 [GB] United Kingdom ............. 9213572
Nov. 12, 1992 [GB] United Kingdom ............. 9223735

[51] Int. Cl.$^6$ ............. A61K 31/51; A61K 31/535; C07D 239/82; C07D 239/74
[52] U.S. Cl. ............. 514/234.5; 514/243; 514/253; 514/259; 544/115; 544/119; 544/231; 544/284; 544/293
[58] Field of Search ............. 544/284, 293, 544/115, 119, 231; 514/253, 259, 234.5, 243

[56] References Cited

U.S. PATENT DOCUMENTS

| | | | |
|---|---|---|---|
| 3,985,742 | 10/1976 | Foster ............. | 544/284 |
| 3,985,749 | 10/1976 | Foster ............. | 544/284 |
| 4,464,375 | 8/1984 | Kobayashi et al. ............. | 544/293 |
| 4,640,920 | 2/1987 | Boyle et al. ............. | 514/248 |
| 4,684,657 | 8/1987 | Boyle ............. | 514/313 |
| 4,808,715 | 2/1989 | Boyle et al. ............. | 544/235 |

FOREIGN PATENT DOCUMENTS

| | | |
|---|---|---|
| 46572 | 3/1982 | European Pat. Off. .. |
| 0520722 | 12/1992 | European Pat. Off. .. |
| 20577 | 2/1981 | Japan . |
| 143266 | 9/1982 | Japan . |
| 13765 | 1/1984 | Japan . |
| 2033894 | 5/1980 | United Kingdom . |
| 2160201 | 12/1985 | United Kingdom . |
| 9214716 | 9/1992 | WIPO . |
| 9220642 | 11/1992 | WIPO . |

OTHER PUBLICATIONS

Iyer, R. N. et al., Journal of Scientific and Industrial Research, vol. 15C, 1956, pp. 1–7.
Chemical Abstracts, Iyer; vol. 51, 1957 Abstract No. 9625D, 9625G; Iyer; "Studies in Potential Amebicides".
Chemical Abstracts, Cronin; vol. 70, 1969; Abstract No. 68419U; "Hypotensive and Bronchodilatory Quinolines, Isoquinolines and Quinazolines" p. 397.
Chemical Abstracts, Botros; vol. 80, 1974; Abstract No. 70768G; "Synthesis of Certain Nitroquinazoline Derivatives Structurally Related to Some Chemotherapeutic Agents" p. 343.
Chemical Abstracts LI; vol. 92; 1980; Abstract No. 76445U; "Synthesis of Shangrolin Analogs as Antimalerial Agents" p. 674.
Chemical Abstracts Lin; vol. 96, 1982; Abstract No. 122728W; "Studies on Antiarrhythmics" p. 695.
Burke; "Protein–Tyrosine Kinase Inhibitors"; Drugs of the Future, vol. 17, No. 2, 1992; pp. 119–131.
Toi et al, "Antineoplastic Effect of Erbstatin on Human Mammary and Esophageal Tumors in Athymic Nude Mice", Eur. J. Cancer, vol. 26, No. 6, pp. 722–724, 1990.
Yoneda et al, "The Antiproliferative Effects of Tyrosine Kinase Inhibitors Tyrphostins on a Human Squamous Cell Carcinoma in Vitro and in Nude Mice[1]", Cancer Research 51, 4430–4435, Aug. 15, 1991.
Honma et al, "Herbimycin A, an Inhibitor of Tyrosine Kinase, Prolongs Survival of Mice Inoculated with Myeloid Leukemia C1 Cells with High Expression of v–abl Tyrosine Kinase[1]", Cancer Research 52, 4017–4020, Jul. 15, 1992.
Chemical Abstracts, 107, 134278H p. 3 (1987).
Chemical Abstracts 58, 9268 p. 4 (1963).
Oakes; "Polyazanaphthalenes. Part VII.1 Some Derivatives of Quinazoline and 1,3,5–Triazanaphthalene" J. Chemical Society; 1962, 4679 p. 4.

Primary Examiner—Mukund J. Shah
Assistant Examiner—Matthew V. Grumbling
Attorney, Agent, or Firm—Cushman Darby & Cushman

[57] ABSTRACT

The invention concerns quinazoline derivatives of the formula I

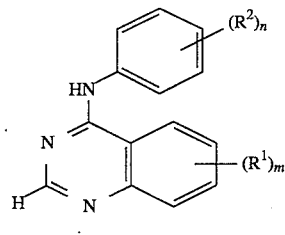

wherein
m is 1, 2 or 3 and each $R^1$ includes hydroxy, amino, carboxy, carbamoyl, ureido, (1–4C)alkoxycarbonyl, N-(1–4C)alkylcarbamoyl, N,N-di-[(1–4C)alkyl]carbamoyl, hydroxyamino, (1–4C)alkoxyamino, (2–4C)alkanoyloxyamino, trifluoromethoxy, (1–4C)alkyl, (1–4C)alkoxy and (1–3C)alkylenedioxy;

n is 1 or 2 and each $R^2$ includes hydrogen, hydroxy, halogeno, trifluoromethyl, amino, nitro, cyano and (1–4C)alkyl;

or a pharmaceutically-acceptable salt thereof;

processes for their preparation; pharmaceutical compositions containing them; and the use of the receptor tyrosine kinase inhibitory properties of the compounds in the treatment of cancer.

29 Claims, No Drawings

QUINAZOLINE DERIVATIVES USEFUL FOR TREATMENT OF NEOPLASTIC DISEASE

This is a continuation of application Ser. No. 08/005,280, filed on Jan. 19, 1993, which was abandoned upon the filing hereof.

The invention relates to quinazoline derivatives, or pharmaceutically-acceptable salts thereof, which possess anti-cancer activity and are accordingly useful in methods of treatment of the human or animal body. The invention also relates to processes for the manufacture of said quinazoline derivatives, to pharmaceutical compositions containing them and to their use in the manufacture of medicaments of use in the production of an anti-cancer effect in a warm-blooded animal such as man.

Many of the current treatment regimes for cancer utilise compounds which inhibit DNA synthesis. Such compounds are toxic to cells generally but their toxic effect on the rapidly dividing tumour cells can be beneficial. Alternative approaches to anti-cancer agents which act by mechanisms other than the inhibition of DNA synthesis have the potential to display enhanced selectivity of action against cancer cells.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Several such oncogenes give rise to the production of peptides which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al. *Ann. Reports in Med. Chem.* 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor and an intracellular portion which functions as a kinase to phosphorylate tyrosine amino acids in proteins and hence to influence cell proliferation. It is known that such kinases are frequently present in common human cancers such as breast cancer (Sainsbury et al., *Brit. J. Cancer,* 1988, 58, 458; Guerin et al., *Oncogene Res.,* 1988, 3, 21), gastrointestinal cancer such as colon, rectal or stomach cancer (Bolen et al., *Oncogene Res.,* 1987, 1, 149), leukaemia (Konaka et al., *Cell,* 1984, 37, 1035) and ovarian, bronchial or pancreatic cancer (European Patent Specification No. 0400586). As further human tumour tissues are tested for receptor tyrosine kinase activity it is expected that its widespread prevalance will be established in further cancers such as thyroid and uterine cancer. It is also known that tyrosine kinase activity is rarely detected in normal cells whereas it is more frequently detectable in malignant cells (Hunter, *Cell,* 1987, 50, 823). It has been shown more recently (W J Gullick, *Brit. Med. Bull.,* 1991, 47, 87) that epidermal growth factor receptor which possesses tyrosine kinase activity is overexpressed in many human cancers such as brain, lung squamous cell, bladder, gastric, breast, head and neck, oesophageal, gynaecological and thyroid tumours.

Accordingly it has been recognised that an inhibitor of receptor tyrosine kinase should be of value as a selective inhibitor of the growth of mammalian cancer cells (Yaish et al. *Science,* 1988, 242, 933). Support for this view is provided by the demonstration that erbstatin, a receptor tyrosine kinase inhibitor, specifically attenuates the growth in athymic nude mice of a transplanted human mammary carcinoma which expresses epidermal growth factor (EGF) receptor tyrosine kinase but is without effect on the growth of another carcinoma which does not express EGF receptor tyrosine kinase (Toi et al., *Eur. J. Cancer Clin. Oncol.,* 1990, 26, 722.) Various derivatives of styrene are also stated to possess tyrosine kinase inhibitory properties (European Patent Application Nos. 0211363, 0304493 and 0322738) and to be of use as anti-tumour agents. The in vivo inhibitory effect of two such styrene derivatives has been demonstrated against the growth of human squamous cell carcinoma inoculated into nude mice (Yoneda et al., *Cancer Research,* 1991, 51, 4430). Accordingly it has been indicated that receptor tyrosine kinase inhibitors will prove to be useful in the treatment of a variety of human cancers. Various known tyrosine kinase inhibitors are disclosed in a more recent review by T R Burke Jr. (*Drugs of the Future,* 1992, 17, 119).

We have now found that certain quinazoline derivatives possess anti-cancer properties which are believed to arise from their receptor tyrosine kinase inhibitory properties.

Many quinazoline derivatives are already known but we are not aware of any public disclosure that any such quinazoline derivative possesses anti-cancer properties arising from receptor tyrosine kinase inhibitory properties.

It is known from UK Patent Application No. 2033894 that certain quinazoline derivatives possess analgesic and anti-inflammatory properties. The compounds, and pharmaceutical compositions containing them, are disclosed by way of a generic formula II (set our hereinafter) wherein $R^1$ is hydrogen, halogeno, trifluoromethyl or nitro;

$R^2$ is hydrogen, halogeno, alkyl or alkoxy; and $R^3$ is hydrogen or alkyl.

With one exception, all of the examples or named compounds therein require $R^1$ to be a substituent other than hydrogen. The exception is the compound 4-(N-methylanilino)quinazoline i.e. each of $R^1$ and $R^2$ is hydrogen and $R^3$ is methyl. It is believed that the quinazoline derivatives disclosed hereinafter do not embrace any of the specifically disclosed compounds of UK Patent Specification No. 2033894.

Further known quinazoline derivatives mentioned in UK 2033894 include the compounds 4-anilinoquinazoline and 4-anilino-6-chloroquinazoline [*J. Org. Chem.*, 1976, 41, 2646 and U.S. Pat. No. 3,985,749 respectively], known for use in the treatment of coccidiosis.

It is known from *Chemical Abstracts*, volume 107, abstract number 134278h, that certain 4-(4'-hydroxyanilino)quinazoline derivatives have been tested for antiarrythmic properties. Compounds mentioned as chemical intermediates include 4-(4'-hydroxyanilino)-6-methoxyquinazoline and 4-(4'-hydroxyanilino)-6,7-methylenedioxyquinazoline. It is known from *Chemical Abstracts*, volume 70, abstract number 68419u, that certain 4-aminoquinazoline derivatives possess bronchodilator and/or hypotensive properties. One such compound disclosed is 4-anilino-6,7-dimethoxyquinazoline- It is further known from *Chemical Abstracts*, volume 92, abstract number 76445u, that certain 6,7,8-trimethoxyquinazoline derivatives possess antimalarial properties. One compound mentioned as a chemical intermediate is 4-(4'-hydroxyanilino)-6,7,8-trimethoxyquinazoline.

It is further known from *Chemical Abstracts*, volume 58, abstract number 9268, that certain 4-(4'-azoanilino)quinazoline derivatives are dyestuffs. A compound mentioned therein as an intermediate is 6-amino-4-(4'-aminoanilino- )quinazoline. It is also known from *J. Chem. Soc.*, 1962, 4679 that 4-chloro-6-methylquinazoline reacts with aniline to furnish 4-anilino-6-methylquinazoline.

According to one aspect of the invention there is provided a quinazoline derivative of the formula I (set out hereinafter) wherein m is 1, 2 or 3 and each $R^1$ is independently hydroxy, amino, carboxy, carbamoyl, ureido, (1–4C)alkoxycarbonyl, N-(1–4C)alkylcarbamoyl, N,N-di-[(1–4C)alkyl]carbamoyl, hydroxyamino, (1–4C)alkoxyamino, (2–4C)alkanoyloxyamino, trifluoromethoxy, (1–4C)alkyl, (1–4C)alkoxy, (1–3C)alkylenedioxy, (1–4C)alkylamino, di-[(1–4C)alkyl]amino, pyrrolidin-1-yl, piperidino, morpholino, piperazin-1-yl, 4-(1–4C)alkylpiperazin-1-yl, (1–4C)alkylthio, (1–4C)alkylsulphinyl, (1–4C)alkylsulphonyl, halogeno-(1–4C)alkyl (other than trifluoromethyl), hydroxy-(1–4C)alkyl, (2–4C)alkanoyloxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]-carbamoyl-(1–4C)alkyl, amino-(1–4C)alkyl, (1–4C)alkylamino-(1–4C)alkyl, di-[(1–4C)alkyl]amino-(1–4C)alkyl, piperidino-(1–4C)alkyl, morpholino-(1–4C)alkyl, piperazin-1-yl-(1–4C)alkyl, 4-(1–4C)alkylpiperazin-1-yl-(1–4C)alkyl, hydroxy-(2–4C)alkoxy-(1–4C)alkyl, (1–4C)alkoxy-(2–4C)alkoxy-(1–4C)alkyl, hydroxy-(2–4C)alkylamino-(1–4C)alkyl, (1–4C)alkoxy-(2–4C)alkylamino-(1–4C)alkyl, (1–4C)alkylthio(1–4C)alkyl, hydroxy-(2–4C)alkylthio-(1–4C)alkyl, (1–4C)alkoxy-(2–4C)alkylthio-(1–4C)alkyl, phenoxy-(1–4C)alkyl, anilino-(1–4C)alkyl, phenylthio-(1–4C)alkyl, cyano-(1–4C)alkyl, halogeno-(2–4C)alkoxy, hydroxy-(2–4C)alkoxy, (2–4C)alkanoyloxy-(2–4C)alkoxy, (1–4C)alkoxy-(2–4C)alkoxy, carboxy-(1–4C)alkoxy, (1–4C)alkoxycarbonyl-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, amino-(2–4C)alkoxy, (1–4C)alkylamino-(2–4C)alkoxy, di-[(1–4C)alkyl]amino-(2–4C)alkoxy, (2–4C)alkanoyloxy, hydroxy-(2–4C)alkanoyloxy, (1–4C)alkoxy-(2–4C)alkanoyloxy, phenyl-(1–4C)alkoxy, phenoxy-(2–4C)alkoxy, anilino-(2–4C)alkoxy, phenylthio-(2–4C)alkoxy, piperidino-(2–4C)alkoxy, morpholino-(2–4C)alkoxy, piperazin-1-yl-(2–4C)alkoxy, 4-(1–4C)alkylpiperazin-1-yl-(2–4C)alkoxy, halogeno-(2–4C)alkylamino, hydroxy-(2–4C)alkylamino, (2–4C)alkanoyloxy-(2–4C)alkylamino, (1–4C)alkoxy-(2–4C)alkylamino, carboxy-(1–4C)alkylamino, (1–4C)alkoxycarbonyl-(1–4C)alkylamino, carbamoyl-(1–4C)alkylamino, N-(1–4C)alkylcarbamoyl-(1–4C)alkylamino, N,N-di-[(1–4C)alkyl]carbamoyl-(1–4C)alkylamino, amino-(2–4C)alkylamino, (1–4C)alkylamino-(2–4C)alkylamino, di-[(1–4C)alkyl]amino-(2–4C)alkylamino, phenyl-(2–4C)alkylamino, phenoxy-(2–4C)alkylamino, anilino-(2–4C)alkylamino, phenylthio-(2–4C)alkylamino, (2–4C)alkanoylamino, (1–4C)alkoxycarbonylamino, (1–4C)alkylsulphonylamino, benzamido, benzenesulphonamido, 3-phenylureido, 2-oxopyrrolidin-1-yl, 2,5-dioxopyrrolidin-1-yl, halogeno-(2–4C)alkanoylamino, hydroxy-(2–4C)alkanoylamino, (1–4C)alkoxy-(2–4C)alkanoylamino, carboxy-(2–4C)alkanoylamino, (1–4C)alkoxycarbonyl-(2–4C)alkanoylamino, carbamoyl-(2–4C)alkanoylamino, N-(1–4C)alkylcarbamoyl-(2–4C)alkanoylamino, N,N-di-[(1–4C)alkyl]carbamoyl-(2–4C)alkanoylamino, amino-(2–4C)alkanoylamino, (1–4C)alkylamino-(2–4C)alkanoylamino or di-[(1–4C)alkyl]amino-(2–4C)alkanoylamino, and wherein said benzamido or benzenesulphonamido substituent or any anilino, phenoxy or phenyl group in a $R^1$ substituent may optionally bear one or two halogeno, (1–4C)alkyl or (1–4C)alkoxy substituents; n is 1 or 2 and each $R^2$ is independently hydrogen, hydroxy, halogeno, trifluoromethyl, amino, nitro, cyano, (1–4C)alkyl, (1–4C)alkoxy, (1–4C)alkylamino, di-[(1–4C)alkyl]amino, (1–4C)alkylthio, (1–4C)alkylsulphinyl or (1–4C)alkylsulphonyl; or a pharmaceutically-acceptable salt thereof; except that 4-(4,-hydroxyanilino)-6-methoxyquinazoline, 4-(4,-hydroxyanilino)-6,7-methylenedioxyquinazoline, 4-(4,-hydroxyanilino)-6,7,8-trimethoxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof are excluded.

According to a further aspect of the invention there is provided a quinazoline derivative of the formula I as defined hereinbefore wherein in addition $R^2$ may be (2–4C)alkanoylamino, benzamido or (2–4C)alkanoyl, and wherein said benzamido group may optionally bear one or two halogeno, (1–4C)alkyl or (1–4C)alkoxy substituents; or a pharmaceutically-acceptable salt thereof.

According to a further aspect of the invention there is provided a quinazoline derivative of the formula I wherein m is 1, 2 or 3 and each $R^1$ is independently hydroxy, amino, carboxy, carbamoyl, ureido, (1–4C)alkoxycarbonyl, N-(1–4C)alkylcarbamoyl, N,N-di-[(1–4C)alkyl]carbamoyl, (1–4C)alkyl, (1–4C)alkoxy, (1–3C)alkylenedioxy, (1–4C)alkylamino, di-[(1–4C)alkyl]amino, (1–4C)alkylthio, (1–4C)alkylsulphinyl, (1–4C)alkylsulphonyl, halogeno-(1–4C)alkyl (other than trifluoromethyl), hydroxy-(1–4C)alkyl, (2–4C)alkanoyloxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]-carbamoyl-(1–4C)alkyl, amino-(1–4C)alkyl, (1–4C)alkylamino-(1–4C)alkyl, di-[(1–4C)alkyl]amino-(1–4C)alkyl, piperidino-(1–4C)alkyl, morpholino-(1–4C)alkyl, piperazin-1-yl-(1–4C)alkyl, 4-(1–4C)alkylpiperazin-1-yl-(1–4C)alkyl, hydroxy-(2–4C)alkoxy-(1–4C)alkyl, (1–4C)alkoxy-(2–4C)alkoxy(1–4C)alkyl, hydroxy-(2–4C)alkylamino-(1–4C)alkyl, (1–4C)alkoxy-(2–4C)alkylamino-(1–4C)alkyl, (1–4C)alkylthio(1–4C)alkyl, hydroxy-(2–4C)alkylthio-(1–4C)alkyl, (1–4C)alkoxy-(2–4C)alkylthio-(1–4C)alkyl, halogeno-(2–4C)alkoxy, hydroxy-(2–4C)alkoxy, (2–4C)alkanoyloxy-(2–4C)alkoxy, (1–4C)alkoxy-(2–4C)alkoxy, carboxy-(1–4C)alkoxy, (1–4C)alkoxycarbonyl-(1–4C)alkoxy, carbamoyl-(1–4C)alkoxy, N-(1–4C)alkylcarbamoyl-(1–4C)alkoxY, N,N-di-[(1–4C)alkyl]carbamoyl-(1–4C)alkoxy, amino-(2–4C)alkoxy, (1–4C)alkylamino-(2–4C)alkoxy, di-[(1–4C)alkyl]amino-(2–4C)alkoxy, halogeno-(2–4C)alkylamino, hydroxy-(2–4C)alkylamino, (2–4C)alkanoyloxy-(2–4C)alkylamino, (1–4C)alkoxy-(2–4C)alkylamino, carboxy-(1–4C)alkylamino, (1–4C)alkoxycarbonyl-(1–4C)alkylamino, carbamoyl-(1–4C)alkylamino, N-(1–4C)alkylcarbamoyl-(1–4C)alkylamino, N,N-di-[(1–4C)alkyl]carbamoyl-(1–4C)alkylamino, amino-(2–4C)alkylamino, (1–4C)alkylamino-(2–4C)alkylamino, di-[(1–4C)alkyl]amino-(2–4C)alkylamino, (2–4C)alkanoylamino, (1–4C)alkoxycarbonylamino, (1–4C)alkylsulphonylamino, benzamido, benzenesulphonamido, halogeno-(2–4C)alkanoylamino, hydroxy-(2–4C)alkanoylamino, (1–4C)alkoxy-(2–4C)alkanoylamino, carboxy- (2–4C)alkanoylamino, (1–4C)alkoxycarbonyl-(2–4C)alkanoylamino, carbamoyl-(2–4C)alkanoylamino, N-(1–4C)alkylcarbamoyl-(2–4C)alkanoylamino, N,N-di-[(1–4C)alkyl]carbamoyl-(2–4C)alkanoylamino, amino-(2–4C)alkanoylamino, (1–4C)alkylamino-(2–4C)alkanoylamino or di-[(1–4C)alkyl]amino-(2–4C)alkanoylamino, and wherein said benzamido or benzenesulphonamido substituent may optionally bear one or two halogeno, (1–4C)alkyl or (1–4C)alkoxy substituents; n is 1 or 2 and each $R^2$ is independently hydrogen, hydroxy, halogeno, trifluoromethyl, amino, nitro, cyano, (1–4C)alkyl, (1–4C)alkoxy, (1–4C)alkylamino, di-[(1–4C)alkyl]amino, (1–4C)alkylthio, (1–4C)alkylsulphinyl or (1–4C)alkylsulphonyl; or a pharmaceutically-acceptable salt thereof; except that 4-(4'-hydroxyanilino)-6-methoxyquinazoline, 4-(4'-hydroxyanilino)-6,7-methylenedioxyquinazoline, 4-(4'-hydroxyanilino)-6,7,8-trimethoxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof are excluded.

According to a further aspect of the invention there is provided a quinazoline derivative of the formula I wherein m is 1 or 2 and each $R^1$ is independently hydroxy, amino, carboxy, (1–4C)alkoxycarbonyl, (1–4C)alkyl, (1–4C)alkoxy, (1–3C)alkylenedioxy, (1–4C)alkylamino, di-[(1–4C)alkyl]amino, (1–4C)alkylthio, (1–4C)alkylsulphinyl, (1–4C)alkylsulphonyl, hydroxy-(1–4C)alkyl, (1–4C)alkoxy-(1–4C)alkyl, amino-(1–4C)alkyl, (1–4C)alkylamino-(1–4C)alkyl, di-[(1–4C)alkyl]amino-(1–4C)alkyl, hydroxy-(2–4C)alkoxy, (1–4C)alkoxy-(2–4C)alkoxy, carboxy-(1–4C)alkoxy, (1–4C)alkoxycarbonyl-(1–4C)alkoxy, (2–4C)alkanoylamino, (1–4C)alkylsulphonylamino, benzamido or benzenesulphonamido, and wherein said last 2 substituents may optionally bear one or two halogeno, (1–4C)alkyl or (1–4C)alkoxy substituents; n is 1 or 2 and each $R^2$ is independently hydrogen, hydroxy, halogeno, trifluoromethyl, amino, nitro, cyano, (1–4C)alkyl, (1–4C)alkoxy, (1–4C)alkylamino, di-[(1–4C)alkyl]amino, (1–4C)alkylthio, (1–4C)alkylsulphinyl or (1–4C)alkylsulphonyl; or a pharmaceutically-acceptable salt thereof; except that 4-(4,-hydroxyanilino)-6-methoxyquinazoline, 4-(4'-hydroxyanilino)-6,7-methylenedioxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof are excluded.

The chemical formulae referred to herein by Roman numerals are set out for convenience on a separate sheet hereinafter. In this specification the term "alkyl" includes both straight and branched chain alkyl groups but references to individual alkyl groups such as "propyl" are specific for the straight chain version only. An analogous convention applies to other generic terms.

Within the present invention it is to be understood that a quinazoline of the formula I may exhibit the phenomenon of tautomerism and that the formulae drawings within this specification can represent Only one of the possible tautomeric forms. It is to be understood that the invention encompasses any tautomeric form which possesses anti-cancer activity and is not to be limited merely to any one tautomeric form utilised within the formulae drawings.

The quinazolines of the formula I are unsubstituted at the 2-position. This is specifically indicated in formula I by the hydrogen atom at the 2-position. It is to be understood that the $R^1$ groups are located only on the benzo position of the quinazoline ring.

It is also to be understood that certain quinazolines of the formula I can exist in solvated as well as unsolvated forms such as, for example, hydrated forms. It is to be understood that the invention encompasses all such solvated forms which possess anti-cancer activity.

Suitable values for the generic radicals referred to above include those set out below.

A suitable value for $R^1$ or $R^2$ when it is (1–4C)alkyl is, for example, methyl, ethyl, propyl, isopropyl, butyl, isobutyl, sec-butyl or tert-butyl; when it is (1–4C)alkoxy is, for example, methoxy, ethoxy, propoxy, isopropoxy or butoxy; when it is (1–4C)alkylamino is, for example, methylamino, ethylamino or propylamno; when it is di-[(1–4C)alkyl]amino is, for example, dimethylamino, N-ethyl-N-methylamino, diethylamino, N-methyl-N-propylamino or dipropylamino; when it is (1–4C)alkylthio is, for example, methylthio, ethylthio or propylthio; when it is (1–4C)alkylsulphinyl is, for example, methylsulphinyl, ethylsulphinyl or propylsulphinyl; when it is (1–4C)alkylsulphonyl is, for example, methylsulphonyl, ethylsulphonyl or propylsulphonyl; and when it is (2–4C)alkanoylamino is, for example, acetamido, propionamido or butyramido.

Suitable values for each $R^1$ substituent which may be present on the quinazoline ring include, for example:

for (1–4C)alkoxycarbonyl: methoxycarbonyl, ethoxycarbonyl, propoxycarbonyl and tert-butoxycarbonyl;

for N-(1–4C)alkylcarbamoyl: N-methylcarbamoyl, N-ethylcarbamoyl and N-propylcarbamoyl;

for N,N-di-[ (1–4C)alkyl]carbamoyl: N,N-dimethylcarbamoyl, N-ethyl-N-methylcarbamoyl and N,N-diethylcarbamoyl;

for (1–4C)alkoxyamino: methoxyamino, ethoxyamino and propoxyamino;

for (2–4C)alkanoyloxyamino: acetoxyamino, propionyloxyamino and butyryloxyamino;

for (1–3C)alkylenedioxy: methylenedioxy, ethylenedioxy and propylenedioxy;

for 4-(1–4C)alkylpiperazin-1-yl: 4-methylpiperazin-1-yl and 4-ethylpiperazin-1-yl;

for halogeno-(1–4C)alkyl: fluoromethyl, chloromethyl, bromomethyl, difluoromethyl, dichloromethyl, dibromomethyl, 2-fluoroethyl, 2-chloroethyl and 2-bromoethyl but trifluoromethyl is excluded;

for hydroxy-(1–4C)alkyl: hydroxymethyl, 1-hydroxyethyl, 2-hydroxyethyl and 3-hydroxypropyl;

for (2–4C)alkanoyloxy-(1–4C)alkyl: acetoxymethyl, propionyloxymethyl, butyryloxymethyl, 2-acetoxyethyl and 3-acetoxypropyl;

for (1–4C)alkoxy-(1–4C)alkyl: methoxymethyl, ethoxymethyl, 1-methoxyethyl, 2-methoxyethyl, 2-ethoxyethyl and 3-methoxypropyl;

for carboxy-(1–4C)alkyl: carboxymethyl, 1-carboxyethyl, 2-carboxyethyl and 3-carboxypropyl;

for (1–4C)alkoxycarbonyl(1–4C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;

for carbamoyl-(1–4C)alkyl: carbamoylmethyl, 1-carbamoylethyl, 2-carbamoylethyl and 3-carbamoylpropyl;

for N-(1–4C)alkylcarbamoyl(1–4C)alkyl: N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;

for N,N-di-[ (1–4C)alkyl]carbamoyl-(1–4C) alkyl: N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl;

for amino-(1–4C)alkyl: aminomethyl, 1-aminoethyl, 2-aminoethyl and 3-aminopropyl;

for (1–4C)alkylamino-(1–4C)alkyl: methylaminomethyl, ethylaminomethyl, 1-methylaminoethyl, 2-methylaminoethyl, 2-ethylamimoethyl and 3-methylaminopropyl;

for di-[(1–4C)alkyl]amino(1–4C)alkyl: dimethylaminomethyl, diethylaminomethyl, 1-dimethylaminoethyl, 2-dimethylaminoethyl and 3-dimethylaminopropyl;

for piperidino-(1–4C)alkyl: piperidinomethyl and 2-piperidinoethyl;

for morpholino-(1–4C)alkyl: morpholinomethyl and 2-morpholinoethyl;

for piperazin-1-yl-(1–4C)alkyl: piperazin-1-ylmethyl and 2 -(piperazin-1-yl)ethyl;

for 4- ( 1–4C)alkylpiperazin-1-yl-( 1–4C) alkyl: 4-methylpiperazin-1-ylmethyl, 4-ethylpiperazin-1-ylmethyl, 2-(4-methylpiperazin-1-yl)ethyl and 2-(4-ethylpiperazin-1-yl)ethyl;

for hydroxy-(2–4C)alkoxy( 1–4C)alkyl: 2-hydroxyethoxymethyl, 3-hydroxypropoxymethyl, 2-(2-hydroxyethoxy)ethyl and 2-(3-hydroxypropoxy)ethyl;

for ( 1–4C)alkoxy- (2–4C)alkoxy( 1–4C)alkyl: 2-methoxyethoxymethyl, 2-ethoxyethoxymethyl, 3-methoxypropoxymethyl, 3-ethoxypropoxymethyl, 2-(2-methoxyethoxy)ethyl and 2-(2-ethoxyethoxy)ethyl;

for hydroxy-(2–4C)alkylamino( 1–4C)alkyl: 2-hydroxyethylaminomethyl, 3-hydroxypropylaminomethyl, 2-(2-hydroxyethylamino)ethyl and 2-(3-hydroxypropylamino)ethyl;

for (1–4C)alkoxy-(2–4C)-alkylamino-(1–4C)alkyl: 2-methoxyethylaminomethyl, 2-ethoxyethylaminomethyl, 3-methoxypropylaminomethyl, 2-(2-methoxyethylamino)ethyl and 2-(2-ethoxyethylamino)ethyl;

for (1–4C)alkylthio-(1–4C)alkyl: methylthiomethyl, ethylthiomethyl, 2-methylthioethyl, 2-ethylthioethyl, 3-methylthiopropyl and 3-ethylthiopropyl;

for hydroxy-(2–4C)alkylthio-( 1–4C)alkyl: 2-hydroxyethylthiomethyl, 3-hydroxypropylthiomethyl, 2-(2-hydroxyethylthio)ethyl and 2-(3-hydroxypropylthio)ethyl;

for (1–4C)alkoxy-(2–4C)alkylthio( 1–4C)alkyl: 2-methoxyethylthiomethyl, 2-ethoxyethylthiomethyl, 3-methoxypropylthiomethyl, 2-(2-methoxyethylthio)ethyl and 2-(2-ethoxyethylthio)ethyl;

for phenoxy-(1–4C)alkyl: phenoxymethyl, 2-phenoxyethyl and 3-phenoxypropyl;

for anilino-(1–4C)alkyl: anilinomethyl, 2-anilinoethyl and 3-anilinopropyl;

for phenylthio-(1–4C)alkyl; phenylthiomethyl, 2-phenylthioethyl and 3-phenylthiopropyl;

for cyano-(1–4C)alkyl: cyanomethyl, 2-cyanoethyl and 3-cyanopropyl;

for halogeno-(2–4C)alkoxy: 2-fluoroethoxy, 2-chloroethoxy, 2-bromoethoxy, 3-fluoropropoxy and 3-chloropropoxy;

for hydroxy-(2–4C)alkoxy: 2-hydroxyethoxy, 3-hydroxypropoxy and 4-hydroxybutoxy;

for (2–4C)alkanoyloxy-(2–4C)alkoxy: 2-acetoxyethoxy, 2-propionyloxyethoxy, 2-butyryloxyethoxy and 3-acetoxypropoxy;

for (1–4C)alkoxy-(2–4C)alkoxy: 2-methoxyethoxy, 2-ethoxyethoxy, 3-methoxypropoxy and 4-methoxybutoxy;

for carboxy-(1–4C)alkoxy: carboxymethoxy, 1-carboxyethoxy, 2-carboxyethoxy and 3-carboxypropoxy;

for (1–4C)alkoxycarbonyl( 1–4C)alkoxy: methoxycarbonylmethoxy, ethoxycarbonylmethoxy, 1-methoxycarbonylethoxy, 2-methoxycarbonylethoxy, 2-ethoxycarbonylethoxy and 3-methoxycarbonylpropoxy;

for carbamoyl-(1–4C)alkoxy: carbamoylmethoxy, 1-carbamoylethoxy, 2-carbamoylethoxy and 3-carbamoylpropoxy;

for N-(1–4C)alkylcarbamoyl( 1–4C)alkoxy: N-methylcarbamoylmethoxy, N-ethylcarbamoylmethoxy, 2-(N-methylcarbamoyl)ethoxy, 2-(N-ethylcarbamoyl)ethoxy and 3-(N-methylcarbamoyl)propoxy;

for N,N-di-[(1–4C)alkyl]carbamoyl-( 1–4C) alkoxy: N,N-dimethylcarbamoylmethoxy, N-ethyl-N-methylcarbamoylmethoxy, N,N-diethylcarbamoylmethoxy, 2-(N,N-dimethylcarbamoyl)ethoxy, 2-(N,N-diethylcarbamoyl)ethoxy and 3-(N,N-dimethylcarbamoyl)propoxy;

for amino-(2–4C)alkoxy: 2-aminoethoxy and 3-aminopropoxy;

for (1–4C)alkylamino-(2–4C)alkoxy: 2-methylaminoethoxy, 2-ethylaminoethoxy, 2-propylaminoethoxy, 3-methylaminopropoxy and 3-ethylaminopropoxy;

for di-[(1–4C)alkyl]amino( 2–4C)alkoxy: 2-dimethylaminoethoxy, 2-(N-ethyl-N-methyl)ethoxy, 2-diethylaminoethoxy, 2-dipropylaminoethoxy, 3-dimethylaminopropoxy and 3-diethylaminopropoxy;

for (2–4C)alkanoyloxy: acetoxy, propionyloxy and butyryloxy;

for hydroxy-(2–4C)alkanoyloxy: 2-hydroxyacetoxy, 3-hydroxypropionyloxy and 4-hydroxybutyryloxy;

for (1–4C)alkoxy-(2–4C)alkanoyloxy: 2-methoxyacetoxy, 2-ethoxyacetoxy and 3-methoxypropionyloxy;

for phenyl-(1–4C)alkoxy: benzyloxy, 2-phenylethoxy and 3-phenylpropoxy;

for phenoxy-(2–4C)alkoxy: 2-phenoxyethoxy, 3-phenoxypropoxy and 4-phenoxybutoxy;

for anilino-(2–4C)alkoxy: 2-anilinoethoxy, 3-anilinopropoxy and 4-anilinobutoxy;

for phenylthio-(2–4C)alkoxy: 2-phenylthioethoxy, 3-phenylthiopropoxy and 4-phenylthiobutoxy;

for piperidino-(2–4C)alkoxy: 2-piperidinoethoxy and 3-piperidinopropoxy;

for morpholino-(2–4C)alkoxy: 2-morpholinoethoxy and 3-morpholinopropoxy;

for piperazin-1-yl-(2–4C)alkoxy: 2-(piperazin-1-yl)ethoxy and 3-(piperazin-1-yl)propoxy;

for 4-(1–4C)alkylpiperazin-1-yl( 2–4C)alkoxy: 2-(4-methylpiperazin-1-yl)ethoxy and 3-(4-methylpiperazin-1-yl)propoxy;

for halogeno-(2–4C)alkylamino: 2-fluoroethylamino, 2-chloroethylamino, 2-bromoethylamino, 3-fluoropropylamino and 3-chloropropylamino;

for hydroxy-(2–4C)alkylamino: 2-hydroxyethylamino, 3-hydroxypropylamino and 4-hydroxybutylamino;

for (2–4C)alkanoyloxy( 2–4C)alkylamino: 2-acetoxyethylamino, 2-propionyloxyethylamino, 2-butyryloxyethylamino and 3-acetoxypropylamino;

for (1–4C)alkoxy-(2–4C)alkylamino: 2-methoxyethylamino, 2-ethoxyethylamino, 3-methoxypropylamino and 3-ethoxypropylamino;

for carboxy-(1–4C)alkylamino: carboxymethylamino, 1-carboxyethylamino, 2-carboxyethylamino and 3-carboxypropylamino;

for (1–4C)alkoxycarbonyl( 1–4C)alkylamino: methoxycarbonylmethylamino, ethoxycarbonylmethylamino, 1-methoxycarbonylethylamino, 2-methoxycarbonylethylamino, 2-ethoxycarbonylethylamino and 3-methoxycarbonylpropylamino;

for carbamoyl-(1–4C)alkylamino: carbamoylmethylamino, 1-carbamoylethylamino, 2-carbamoylethylamino and 3-carbamoylpropylamino;

for N-(1–4C)alkylcarbamoyl( 1–4C)alkylamino: N-methylcarbamoylmethylamino, N-ethylcarbamoylmethylamino, 2-(N-methylcarbamoyl)ethylamino, 2-(N-ethylcarbamoyl)ethylamino and 3-(N-methylcarbamoyl)propylamino;

for N,N-di-[ (1–4C)alkyl] carbamoyl-(1–4C)alkylamino: N,N-dimethylcarbamoylmethylamino, N-ethyl-N-methylcarbamoylmethylamino N,N-diethylcarbamoylmethylamino, 2-(N,N-dimethylcarbamoyl)ethylamino, 2-(N,N-diethylcarbamoyl)ethylamino and 3-(N,N-dimethylcarbamoyl)propylamino;

for amino-(2–4C)alkylamino: 2-aminoethylamino, 3-aminopropylamino and 4-aminobutylamino;

for (1–4C)alkylamino( 2–4C)alkylamino: 2-methylaminoethylamino, 2-ethylaminoethylamino, 2-propylaminoethylamino, 3-methylaminopropylamino, 3-ethylaminopropylamino and 4-methylaminobutylamino;

for di-[ (1–4C)alkyl]amino-2-dimethylaminoethylamino, (2–4C ) alkylamino: 2-(N-ethyl-N-methylamino)ethylamino, 2-diethylaminoethylamino, 2-dipropylaminoethylamino, 3-dimethylaminopropylamino, 3-diethylaminopropylamino and 4-dimethylaminobutylamino;

for phenyl-(1–4C)alkylamino: benzylamino, phenethylamino and 3-phenylpropylamino;

for phenoxy-(2–4C)alkylamino: 2-phenoxyethylamino and 3-phenoxypropylamino;

for anilino-(2–4C)alkylamino: 2-anilinoethylamino and 3-anilinopropylamino;

for phenylthio-(2–4C)alkylamino: 2-phenylthioethylamino and 3-phenylthiopropylamino;

for (1–4C)alkoxycarbonylamino: methoxycarbonylamino, ethoxycarbonylamino and propoxycarbonylamino;

for (1–4C)alkylsulphonylamino: methylsulphonylamino, ethylsulphonylamino and propylsulphonylamino;

for halogeno-(2–4C)alkanoylamino: 2-chloroacetamido, 2-bromoacetamido, 3-chloropropionamido and 3-bromopropionamido;

for hydroxy-(2–4C)alkanoylamino: 2-hydroxyacetamido, 3-hydroxypropionamido and 4-hydroxybutyramido;

for (1–4C)alkoxy-(2–4C)alkanoylamino: 2-methoxyacetamido, 2-ethoxyacetamido, 2-propoxyacetamido, 3-methoxypropionamido, 3-ethoxypropionamido and 4-methoxybutyramido;

for carboxy-(2–4C)alkanoylamino: 2-carboxyacetamido, 3-carboxypropionamido and 4-carboxybutyramido;

for (1–4C)alkoxycarbonyl( 2–4C)alkanoylamino: 2-methoxycarbonylacetamido, 2-ethoxycarbonylacetamido, 3-methoxycarbonylpropionamido and 3-ethoxycarbonylpropionamido;

for carbamoyl-(2–4C)alkanoylamino: 2-carbamoylacetamido, 3-carbamoylpropionamido and 4-carbamoylbutyramido;

for N-(1–4C)alkylcarbamoyl( 2–4C)alkanoylamino: 2-(N-methylcarbamoyl)acetamido, 2-(N-ethylcarbamoyl)acetamido, 3-(N-methylcarbamoyl)propionamido, 3-(N-ethylcarbamoyl)propionamido and 4-(N-methylcarbamoyl)butyramido;

for N,N-di-[(1–4C)alkyl]-carbamoyl-(2–4C)alkanoylamino: 2-(N,N-dimethylcarbamoyl)acetamido, 2-(N-ethyl-N-methylcarbamoyl)acetamido, 2-(N,N-diethylcarbamoyl)acetamido, 3-(N,N-dimethylcarbamoyl)propionamido, 3-(N,N-diethylcarbamoyl)propionamido and 4-(N,N-dimethylcarbamoyl)butyramido;

for amino-(2–4C)alkanoylamino: 2-aminoacetamido, 3-aminopropionamido and 4-aminobutyramido;

for (1–4C)alkylamino-(2–4C)alkanoylamino: 2-methylaminoacetamido, 2-ethylaminoacetamido, 2-propylaminoacetamido, 3-methylaminopropionamido, 3-ethylaminopropionamido and 4-methylaminobutyramido;

for di-[(1–4C)alkyl]amino-(2–4C)alkanoylamino: 2-dimethylaminoacetamido, 2-(N-ethyl-N-methylamino)acetamido, 2-diethylaminoacetamido, 3-dimethylaminopropionamido, 3-diethylaminopropionamido and 4-dimethylaminobutyramido.

When $R^1$ is (1–3C)alkylenedioxy the oxygen atoms of each such group occupy adjacent positions on the quinazoline ring.

Suitable values for the substituents which may be present on the phenyl ring when $R^1$ is benzamido or benzenesulphonamido, $R^2$ is benzamido or on a $R^1$ substituent which contains an anilino, phenoxy or phenyl group include, for example:

for halogeno: fluoro, chloro and bromo;

for (1–4C)alkyl: methyl, ethyl and propyl;

for (1–4C)alkoxy: methoxy, ethoxy and propoxy.

A suitable value for $R^2$ when it is halogeno is, for example, fluoro, chloro, bromo or iodo; and when it is (2–4C)alkanoyl is, for example, acetyl, propionyl or butyryl.

A suitable pharmaceutically-acceptable salt of a quinazoline derivative of the invention is, for example, an acid-addition salt of a quinazoline derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a quinazoline derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention include, for example, quinazoline derivatives of the formula I, or pharmaceutically-acceptable salts thereof, subject to the exclusions defined hereinbefore, wherein:

(a) m is 1 or 2 and each $R^1$ is independently hydroxy, (1–4C)alkoxycarbonyl, (1–4C)alkyl, (1–4C)alkoxy or (1–3C)alkylenedioxy; and n and $R^2$ have any of the meanings defined hereinbefore or in this section relating to particular novel compounds of the invention;

(b) m is 1 or 2 and each $R^1$ is independently hydroxy, amino, (1–4C)alkoxycarbonyl, (1–4C)alkyl, (1–4C)alkoxy, (1–3C)alkylenedioxy, halogeno-(1–4C)alkyl (but trifluoromethyl is excluded), (1–4C)alkylamino-(1–4C)alkyl, di-[(1–4C)alkyl]amino-(1–4C)alkyl, piperidino-(1–4C)alkyl, morpholino-(1–4C)alkyl, piperazin-1-yl-(1–4C)alkyl, hydroxy-(2–4C)alkylthio-(1–4C)alkyl, hydroxy-(2–4C)alkoxy, (1–4C)alkoxy-(2–4C)alkoxy, (1–4C)alkoxycarbonyl-(1–4C)alkoxy, carbamoyl-(1–4C)alkoxy, (1–4C)alkylamino-(2–4C)alkoxy, di-[(1–4C)alkyl]amino-(2–4C)alkoxy, hydroxy-(2–4C)alkylamino, (1–4C)alkoxy-(2–4C)alkylamino, (1–4C)alkylamino-(2–4C)alkylamino, di-[(1–4C)alkyl]amino-(2–4C)alkylamino, (2–4C)alkanoylamino, hydroxy-(2–4C)alkanoylamino or (1–4C)alkoxy-(2–4C)alkanoylamino; and n and $R^2$ have any of the meanings defined hereinbefore or in this section relating to particular novel compounds of the invention;

(c) m is 1 or 2 and each $R^1$ is independently hydroxy, (1–4C)alkoxy, (1–3C)alkylenedioxy, hydroxy-(2–4C)alkoxy, (1–4C)alkoxy-(2–4C)alkoxy, (1–4C)alkoxycarbonyl-(1–4C)alkoxy, carbamoyl-(1–4C)alkoxy or di-[(1–4C)alkyl]amino-(2–4C)alkoxy; and n and $R^2$ have any of the meanings defined hereinbefore or in this section relating to particular novel compounds of the invention;

(d) m is 1 or 2 and each $R^1$ is independently amino, hydroxy-(2–4C)alkylamino, (1–4C)alkoxy-(2–4C)alkylamino, di-[(1–4C)alkyl]amino-(2–4C)alkylamino, (2–4C)alkanoylamino, hydroxy-(2–4C)alkanoylamino or (1–4C)alkoxy-(2–4C)alkanoylamino; and n and $R^2$ have any of the meanings defined hereinbefore or in this section relating to particular novel compounds of the invention;

(e) m is 1, 2 or 3 and each $R^1$ is independently hydroxy, amino, carboxy, ureido, (1–4C)alkoxycarbonyl, hydroxyamino, trifluoromethoxy, (1–4C)alkyl, (1–4C)alkoxy, (1–3C)alkylenedioxy, (1–4C)alkylamino, di-[(1–4C)alkyl]amino, piperidino, morpholino, piperazin-1-yl, 4-(1–4C)alkylpiperazin-1-yl, (1–4C)alkylthio, halogeno-(1–4C)alkyl (but trifluoromethyl is excluded), (1–4C)alkoxy-(1–4C)alkyl, (1–4C)alkylamino-(1–4C)alkyl, di-[(1–4C)alkyl]amino-(1–4C)alkyl, piperidino-(1–4C)alkyl, morpholino-(1–4C)alkyl, piperazin-1-yl-(1–4C)alkyl, hydroxy-(2–4C)alkoxy-(1–4C)alkyl, (1–4C)alkoxy-(2–4C)alkoxy-(1–4C)alkyl, (1–4C)alkylthio-(1–4C)alkyl, hydroxy-(2–4C)alkylthio-(1–4C)alkyl, anilino-(1–4C)alkyl, phenylthio-(1–4C)alkyl, cyano-(1–4C)alkyl, halogeno-(2–4C)alkoxy, hydroxy-(2–4C)alkoxy, (1–4C)alkoxy-(2–4C)alkoxy, (1–4C)alkoxycarbonyl-(1–4C)alkoxy, carbamoyl-(1–4C)alkoxy, (1–4C)alkylamino-(2–4C)alkoxy, di-[(1–4C)alkyl]amino-(2–4C)alkoxy, (1–4C)alkoxy-(2–4C)alkanoyloxy, phenyl-(1–4C)alkoxy, phenoxy-(2–4C)alkoxy, anilino-(2–4C)alkoxy, piperidino-(2–4C)alkoxy, morpholino-(2–4C)alkoxy, piperazin-1-yl-(2–4C)alkoxy, hydroxy-(2–4C)alkylamino, (1–4C)alkoxy-(2–4C)alkylamino, (1–4C)alkylamino-(2–4C)alkylamino, di-[(1–4C)alkyl]amino( 2–4C)alkylamino, (2–4C)alkanoylamino, benzamido, 3-phenylureido, 2-oxopyrrolidin-1-yl, halogeno-(2–4C)alkanoylamino, hydroxy-(2–4C)alkanoylamino, (1–4C)alkoxy-(2–4C)alkanoylamino or (1–4C)alkoxycarbonyl-(2–4C)alkanoylamino; and n and $R^2$ have any of the meanings defined hereinbefore or in this section relating to particular novel compounds of the invention;

(f) m is 1 or 2 and each $R^1$ is independently hydroxy, amino, ureido, (1–4C)alkoxycarbonyl, trifluoromethoxy, (1–4C)alkyl, (1–4C)alkoxy, (1–3C)alkylenedioxy, (1–4C)alkylamino, di-[(1–4C)alkyl]amino, piperidino, morpholino, (1–4C)alkylthio, halogeno-(1–4C)alkyl (but trifluoromethyl is excluded), cyano-(1–4C)alkyl, halogeno-(2–4C)alkoxy, hydroxy-(2–4C)alkoxy, (1–4C)alkoxy-(2–4C)alkoxy, carbamoyl-(1–4C)alkoxy, (1–4C)alkoxy-(2–4C)alkanoyloxy, phenyl-(1–4C)alkoxy, anilino-(2–4C)alkoxy, (1–4C)alkoxy-(2–4C)alkylamino, (2–4C)alkanoylamino, halogeno-(2–4C)alkanoylamino, 3-phenylureido, 2-oxopyrrolidin-1-yl or (1–4C)alkoxy-(2–4C)alkanoylamino; and n and $R^2$ have any of the meanings defined hereinbefore or in this section relating to particular novel compounds of the invention;

(g) n is 1 or 2 and each $R^2$ is independently hydrogen, halogeno, trifluoromethyl, nitro, cyano, (1–4C)alkyl, di-[(1–4C)alkyl]amino or (1–4C)alkylthio; and m and $R^1$ have any of the meanings defined hereinbefore or in this section relating to particular novel compounds of the invention;

(h) n is 1 or 2 and each $R^2$ is independently halogeno, trifluoromethyl or (1–4C)alkyl; and m and R have any of the meanings defined hereinbefore or in this section relating to particular novel compounds of the invention; or (i) n is 1 or 2 and each $R^2$ is independently hydrogen, hydroxy, halogeno, trifluoromethyl, amino, nitro, cyano or (1–4C)alkyl; and m and $R^1$ have any of the meanings defined hereinbefore or in this section relating to particular novel compounds of the invention.

A preferred compound of the invention is a quinazoline derivative of the formula I wherein m is 1 or 2 and each $R^1$ is independently hydroxy, methyl, ethyl, methoxy, ethoxy or methylenedioxy;

n is 1 and $R^2$ is hydrogen, fluoro, chloro, bromo, iodo, methyl or ethyl;

or a pharmaceutically-acceptable acid-addition salt thereof;

except that 4-anilino-6-methylquinazoline or the hydrochloride salt thereof and 4-anilino-6,7-dimethoxyquinazoline or the hydrochloride salt thereof are excluded.

A further preferred compound of the invention is a quinazoline derivative of the formula I wherein $(R1)m$ is 6-hydroxy, 7-hydroxy, 6,7-dihydroxy, 6-methyl, 7-methyl, 6-methoxy, 7-methoxy, 6,7-dimethoxy or 6,7-methylenedioxy; and $(R^2)_n$ is 3'-chloro, 3'-bromo or 3'-methyl; or a pharmaceutically-acceptable acid-addition salt thereof.

A specific preferred compound of the invention is the following quinazoline derivative of the formula I, or a pharmaceutically-acceptable acid-addition salt thereof:

6,7-dimethoxy-4-(3'-methylanilino)quinazoline, 6,7-dimethoxy-4-(3'-chloroanilino)quinazoline, 6,7-dimethoxy-4-(3'-bromoanilino)quinazoline, 6,7-methylenedioxy-4-(3'-methylanilino)quinazoline, 7-methoxy-4-(3'-methylanilino)quinazoline, 7-hydroxy-4-(3'-methylanilino)quinazoline, 6-methyl-4-(3'-methylanilino)quinazoline or 7-methoxycarbonyl-4-(3'-methylanilino)quinazoline.

A further preferred compound of the invention is a quinazoline derivative of the formula I wherein m is 1 or 2 and each $R^1$ is independently hydroxy, amino, methoxycarbonyl, ethoxycarbonyl, methyl, ethyl, methoxy, ethoxy, methylenedioxy, dibromomethyl, dimethylaminomethyl, piperazin-1-ylmethyl, 2-hydroxyethylthiomethyl, 2-hydroxyethoxy, 3-hydroxypropoxy, 2-methoxyethoxy, 2-ethoxyethoxy, 3-methoxypropoxy, 3-ethoxypropoxy, methoxycarbonylmethoxy, ethoxycarbonylmethoxy, carbamoylmethoxy, 2-dimethylaminoethoxy, 2-diethylaminoethoxy, 2-hydroxyethylamino, 3-hydroxypropylamino, 2-methoxyethylamino, 2-ethoxyethylamino, 3-methoxypropylamino, 3-ethoxypropylamino, 2-dimethylaminoethylamino, 2-diethylaminoethylamino, 3-dimethylaminopropylamino, 3-diethylaminopropylamino, acetamido, propionamido, 2-methoxyacetamido or 2-ethoxyacetamido;

n is 1 or 2 and each $R^2$ is independently fluoro, chloro, bromo, trifluoromethyl, methyl or ethyl;

or a pharmaceutically-acceptable salt thereof.

A further preferred compound of the invention is a quinazoline derivative of the formula I wherein $(R^1)_m$ is 6-hydroxy, 7-hydroxy, 6,7-dihydroxy, 6-amino, 7-amino, 6-methyl, 6,7-dimethyl, 7-methoxy, 6,7-dimethoxy, 6-hydroxy-7-methoxy, 7-hydroxy-6-methoxy, 6,7-methylenedioxy, 6-(2-hydroxyethylthiomethyl), 7-(2-hydroxyethoxy)-6-methoxy, 6,7-di-(2-hydroxyethoxy), 6-methoxy-7-(2-methoxyethoxy), 7-carbamoylmethoxy-6-methoxy, 7-(2-dimethylaminoethoxy)-6-methoxy, 6-(2-methoxyethylamino), 6-acetamido or 7-(2-methoxyacetamido); and $R^2)_n$ is 4'-fluoro, 3'-chloro, 3N-bromo, 3'-methyl, 3'-trifluoromethyl or 4'-fluoro-3N-trifluoromethyl;

or a pharmaceutically-acceptable acid-addition salt thereof.

A further preferred compound of the invention is a quinazoline derivative of the formula I wherein $(R^1)_m$ is 6-amino, 7-amino, 6-(2-methoxyethylamino), 6-acetamido or 7-(2-methoxyacetamido); and $(R^2)_n$ is 3'-chloro, 3'-methyl or 3'-trifluoromethyl;

or a pharmaceutically-acceptable acid addition salt thereof.

A further specific preferred compound of the invention is the following quinazoline derivative of the formula I, or a pharmaceutically-acceptable acid-addition salt thereof:

6,7-dimethoxy-4-(3'-trifluoromethylanilino)quinazoline, 6-hydroxy-7-methoxy-4-(3'-methylanilino)quinazoline, 7-hydroxy-6-methoxy-4-(3'-methylanilino)quinazoline, 7-amino-4-(3'-methylanilino)quinazoline, 6-amino-4-(3'-methylanilino)quinazoline, 6-amino-4-(3'-chloroanilino)quinazoline, 6-acetamido-4-(3'-methylanilino)quinazoline, 6-(2-methoxyethylamino)-4-(3'-methylanilino)quinazoline, 7-(2-methoxyacetamido)-4-(3'-methylanilino)quinazoline, 7-(2-hydroxyethoxy)-6-methoxy-4-(3'-methylanilino)quinazoline or 7-(2-methoxyethoxy)-6-methoxy-4-(3'-methylanilino)quinazoline.

A further preferred compound of the invention is a quinazoline derivative of the formula I wherein m is 1, 2 or 3 and each $R^1$ is independently hydroxy, amino, ureido, methoxycarbonyl, ethoxycarbonyl, hydroxyamino, trifluoromethoxy, methyl, ethyl, methoxy, ethoxy, propoxy, isopropoxy, butoxy, methylenedioxy, ethylenedioxy, methylamino, ethylamino, dimethylamino, diethylamino, piperidino, morpholino, methylthio, ethylthio, bromomethyl, dibromomethyl, methoxymethyl, piperidinomethyl, morpholinomethyl, piperazin-1-ylmethyl, methoxyethoxymethyl, methylthiomethyl, 2-hydroxyethylthiomethyl, anilinomethyl, phenylthiomethyl, cyanomethyl, 2-bromoethoxy, 2-hydroxyethoxy, 3-hydroxypropoxy, 2-methoxyethoxy, 2-ethoxyethoxy, 3-methoxypropoxy, 3-ethoxypropoxy, methoxycarbonylmethoxy, ethoxycarbonylmethoxy, carbamoylmethoxy, 2-dimethylaminoethoxy, 2-diethylaminoethoxy, 2-methoxyacetoxy, benzyloxy, 2-anilinoethoxy, 2-piperidinoethoxy, 2-morpholinoethoxy, 2-(piperazin-1-yl)ethoxy, 2-hydroxyethylamino, 3-hydroxypropylamino, 2-methoxyethylamino, 2-ethoxyethylamino, 3-methoxypropylamino, 3-ethoxypropylamino, 2-dimethylaminoethylamino, 2-diethylaminoethylamino, 3-dimethylaminopropylamino, 3-diethylaminopropylamino, acetamido, propionamido, benzamido, 3-phenylureido, 2-chloroacetamido, 2-oxopyrrolidin-1-yl, 2-hydroxyacetamido, 2-methoxyacetamido or 2-ethoxyacetamido;

n is 1 or 2 and each $R^2$ is independently hydrogen, fluoro, chloro, bromo, trifluoromethyl, nitro, cyano, methyl or ethyl;

or a pharmaceutically-acceptable salt thereof.

A further preferred compound of the invention is a quinazoline derivative of the formula I wherein $(R^1)_m$ is 6-hydroxy, 7-hydroxy, 6,7-dihydroxy, 6-amino, 7-amino, 6-ureido, 6-trifluoromethoxy, 6-methyl, 6,7-dimethyl, 6-methoxy, 7-methoxy, 6,7-dimethoxy, 6,7-diethoxy, 6-hydroxy-7-methoxy, 7-hydroxy-6-methoxy, 6-amino-7-methoxy, 6-amino-7-methylthio, 5-amino-6,7-dimethoxy, 6-methoxy-7-isopropoxy, 6,7-methylenedioxy, 6,7-ethylenedioxy, 6-dimethylamino, 6-methoxymethyl, 6-(2-methoxyethoxymethyl), 6-cyanomethyl, 7-(2-hydroxyethoxy)-6-methoxy, 6,7-di-(2-hydroxyethoxy), 6-(2-methoxyethoxy), 6-methoxy-7-(2-methoxyethoxy), 6,7-di-(2-methoxyethoxy), 7-(2-bromoethoxy)-6-methoxy, 7-benzyloxy-6-methoxy, 6-(2-methoxyethylamino), 6-acetamido, 6-(2-chloroacetamido), 6-(2-methoxyacetamido) or 7-(2-methoxyacetamido)}; and $R^2)_n$ is hydrogen, 4'-fluoro, 3'-chloro, 3'-bromo, 3',4'-dichloro, 4'-fluoro-3'-chloro, 3'-trifluoromethyl, 4'-fluoro-3'-trifluoromethyl, 3'-nitro, 3'-nitro-4'-chloro, 3'-nitro-4'-fluoro or 3'-methyl;

or a pharmaceutically-acceptable acid-addition salt thereof.

A further specific preferred compound of the invention is the following quinazoline derivative of the formula I, or a pharmaceutically-acceptable acid-addition salt thereof:
4-(3'-chloro-4'-fluoroanilino)-6,7-dimethoxyquinazoline,
4-(3',4'-dichloroanilino)-6,7-dimethoxyquinazoline, 6,7-dimethoxy-4-(3'-nitroanilino)quinazoline, 6,7-diethoxy-4-(3'-methylanilino)quinazoline, 6-methoxy-4-(3'-methylanilino)quinazoline, 4-(3'-chloroanilino)-6-methoxyquinazoline, 6,7-ethylenedioxy-4-(3'-methylanilino)quinazoline, 6-amino-7-methoxy-4-(3'-methylanilino)quinazoline, 4-(3'-methylanilino)-6-ureidoquinazoline or 6-(2-methoxyethoxymethyl)-4-(3'-methylanilino)quinazoline.

A further preferred compound of the invention is a quinazoline derivative of the formula I wherein $(R^1)_m$ is 6-hydroxy, 7-hydroxy, 6,7-dihydroxy, 6-amino, 7-amino, 6-ureido, 6-trifluoromethoxy, 6-methyl, 6,7-dimethyl, 6-methoxy, 7-methoxy, 6,7-dimethoxy, 6,7-diethoxy, 6-hydroxy-7-methoxy, 7-hydroxy-6-methoxy, 6-amino-7-methoxy, 6-amino-7-methylthio, 5-amino-6,7-dimethoxy, 6-methoxy-7-isopropoxy, 6,7-methylenedioxy, 6,7-ethylenedioxy, 6-methylamino, 7-methylamino, 6-dimethylamino, 6-amino-7-methylamino, 6-methoxymethyl, 6-bromomethyl, 6-(2-methoxyethoxymethyl), 6-cyanomethyl, 6-methylthiomethyl, 6-phenylthiomethyl, 7-(2-hydroxyethoxy)-6-methoxy, 6,7-di-(2-hydroxyethoxy), 6-(2-bromoethoxy), 6-(2-methoxyethoxy), 6-methoxy-7-(2-methoxyethoxy), 6,7-di-(2-methoxyethoxy), 7-(2-bromoethoxy)-6-methoxy, 7-benzyloxy-6-methoxy, 6-(2-methoxyethylamino), 6-acetamido, 6-benzamido, 6-(2-chloroacetamido), 6-(2-methoxyacetamido) or 7-(2-methoxyacetamido); and $R^2)_n$ is hydrogen, 4'-fluoro, 3'-chloro, 3'-bromo, 3',4'-dichloro, 4'-fluoro-3'-chloro, 3'-trifluoromethyl, 4'-fluoro-3'-trifluoromethyl, 3'-nitro, 3'-nitro-4'-chloro, 3'-nitro-4'-fluoro or 3'-methyl;

or a pharmaceutically-acceptable acid-addition salt thereof.

A further specific preferred compound of the invention is the following quinazoline derivative of the formula I, or a pharmaceutically-acceptable acid-addition salt thereof:

6,7-di-(2-methoxyethoxy)-4-(3'-methylanilino)quinazoline, 6-dimethylamino-4-(3'-methylanilino)quinazoline or 6-benzamido-4-(3'-methylanilino)quinazoline.

A quinazoline derivative of the formula I, or a pharmaceutically-acceptable salt thereof, may be prepared by any process known to be applicable to the preparation of chemically-related compounds. A suitable process is, for example, illustrated by that used in UK Patent Application No. 2033894. Such processes, when used to prepare a quinazoline derivative of the formula I, or a pharmaceutically-acceptable salt thereof, are provided as a further feature of the invention and are illustrated by the following representative examples in which, unless otherwise stated, $R^1$, m, n and $R^2$ have any of the meanings defined hereinbefore for a quinazoline derivative of the formula I. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

(a) The reaction, conveniently in the presence of a suitable base, of a quinazoline of the formula III (set out hereinafter), wherein Z is a displaceable group, with an aniline of the formula IV.

A suitable displaceable group Z is, for example, a halogeno, alkoxy, aryloxy or sulphonyloxy group, for example a chloro, bromo, methoxy, phenoxy, methanesulphonyloxy or toluene-p-sulphonyloxy group.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

The reaction is preferably carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10° to 150° C., preferably in the range 20° to 80° C.

The quinazoline derivative of the formula I may be obtained from this process in the form of the free base or alternatively it may be obtained in the form of a salt with the acid of the formula H–Z wherein Z has the meaning defined hereinbefore. When it is desired to obtain the free base from the salt, the salt may be treated with a suitable base as defined hereinbefore using a conventional procedure.

(b) For the production of those compounds of the formula I wherein $R^1$ or $R^2$ is hydroxy, the cleavage of a quinazoline derivative of the formula I wherein $R^1$ or $R^2$ is (1–4C)alkoxy.

The cleavage reaction may conveniently be carried out by any of the many procedures known for such a transformation. The reaction may be carried out, for example, by treatment of the quinazoline derivative with an alkali metal (1–4C)alkylsulphide such as sodium ethanethiolate or, for example, by treatment with an alkali metal diarylphosphide such as lithium diphenylphosphide. Alternatively the cleavage reaction may conveniently be carried out, for example, by treatment of the quinazoline derivative with a boron or aluminium trihalide such as boron tribromide. Such reactions are preferably carried out in the presence of a suitable inert solvent or diluent as defined hereinbefore and at a suitable temperature as illustrated in the accompanying Examples.

(c) For the production of those compounds of the formula I wherein $R^1$ or $R^2$ is a (1–4C)alkylsulphinyl or (1–4C)alkylsulphonyl group, the oxidation of a quinazoline derivative of the formula I wherein $R^1$ or $R^2$ is a (1–4C)alkylthio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, −25° to 50° C., conveniently at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a (1–4C)alkylsulphonyl group is required, it may be obtained by oxidation of the corresponding (1–4C)alkylsulphinyl compound as well as of the corresponding (1–4C)alkylthio compound.

(d) For the production of those compounds of the formula I wherein $R^1$ is amino, the reduction of a quinazoline derivative of the formula I wherein $R^1$ is nitro.

The reduction may conveniently be carried out by any of the many procedures known for such a transformation. The reduction may be carrried out, for example, by the hydrogenation of a solution of the nitro compound in an inert solvent or diluent as defined hereinbefore in the presence of a suitable metal catalyst such as palladium or platinum. A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example, 50° to 150° C., conveniently at or near 70° C.

(e) For the production of those compounds of the formula I wherein $R^1$ is (2–4C)alkanoylamino or substituted (2–4C)alkanoylamino, ureido, 3-phenylureido or benzamido, or $R^2$ is acetamido or benzamido, the acylation of a quinazoline derivative of the formula I wherein $R^1$ or $R^2$ is amino.

A suitable acylating agent is, for example, any agent known in the art for the acylation of amino to acylamino, for example an acyl halide, for example a (2–4C)alkanoyl chloride or bromide or a benzoyl chloride or bromide, conveniently in the presence of a suitable base, as defined hereinbefore, an alkanoic acid anhydride or mixed anhydride, for example a (2–4C)alkanoic acid anhydride such as acetic anhydride or the mixed anhydride formed by the reaction of an alkanoic acid and a (1–4C)alkoxycarbonyl halide, for example a (1–4C)alkoxycarbonyl chloride, in the presence of a suitable base as defined hereinbefore. For the production of those compounds of the formula I wherein $R^1$ is ureido or 3-phenylureido, a suitable acylating agent is, for example, a cyanate, for example an alkali metal cyanate such as sodium cyanate or, for example, an isocyanate such as phenyl isocyanate. In general the acylation is carried out in a suitable inert solvent or diluent as defined hereinbefore and at a temperature, in the range, for example, –30° to 120° C., conveniently at or near ambient temperature.

(f) For the production of those compounds of the formula I wherein $R^1$ is (1–4C)alkoxy or substituted (1–4C)alkoxy or $R^1$ is (1–4C)alkylamino or substituted (1–4C)alkylamino, the alkylation, preferably in the presence of a suitable base as defined hereinbefore, of a quinazoline derivative of the formula I wherein $R^1$ is hydroxy or amino as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1–4C)alkyl chloride, bromide or iodide or a substituted (1–4C)alkyl chloride, bromide or iodide, in the presence of a suitable base as defined hereinbefore, in a suitable inert solvent or diluent as defined hereinbefore and at a temperature in the range, for example, 10° to 140° C., conveniently at or near ambient temperature.

(g) For the production of those compounds of the formula I wherein $R^1$ is a carboxy substituent or a substituent which includes a carboxy group, the hydrolysis of a quinazoline derivative of the formula I wherein $R^1$ is a (1–4C)alkoxycarbonyl substituent or a substituent which includes a (1–4C)alkoxycarbonyl group.

The hydrolysis may conveniently be performed, for example, under basic conditions as illustrated in the accompanying Examples.

(h) For the production of those compounds of the formula I wherein $R^1$ is an amino-, oxy-, thio- or cyano-substituted (1–4C)alkyl substituent, the reaction, preferably in the presence of a suitable base as defined hereinbefore, of a quinazoline derivative of the formula I wherein $R^1$ is a (1–4C)alkyl substituent bearing a displaceable group as defined hereinbefore with an appropriate amine, alcohol, thiol or cyanide.

The reaction is preferably carried out in a suitable inert solvent or diluent as defined hereinbefore and at a temperature in the range, for example, 10 to 100° C., conveniently at or near ambient temperature.

When a pharmaceutically-acceptable salt of a quinazoline derivative of the formula I is required, it may be obtained, for example, by reaction of said compound with, for example, a suitable acid using a conventional procedure.

Many of the intermediates defined herein are novel, for example, those of the formula III and these are provided as a further feature of the invention. Moreover some of the starting materials for use in process variant (d) described hereinbefore, namely those compounds of the formula I wherein m is 2 or 3 and one of the $R^1$ groups is nitro, are not only novel but also active as inhibitors of receptor tyrosine kinase. Accordingly these compounds are provided as a further feature of the invention.

As stated hereinbefore the quinazoline derivative defined in the present invention possesses anti-cancer activity which is believed to arise from the receptor tyrosine kinase inhibitory activity of the compound. These properties may be assessed, for example, using one or more of the procedures set out below:

(a) An in vitro assay which determines the ability of a test compound to inhibit the enzyme receptor tyrosine kinase. Receptor tyrosine kinase was obtained in partially purified form from A-431 cells (derived from human vulval carcinoma) by procedures related to those described by Carpenter et al., *J. Biol. Chem.*, 1979, 254, 4884, Cohen et al., *J. Biol. Chem.*, 1982, 257, 1523 and by Braun et al., *J. Biol. Chem.*, 1984, 259, 2051.

A-431 cells were grown to confluence using Dulbecco's modified Eagle's medium (DMEM) containing 5% fetal calf serum (FCS). The obtained cells were homogenised in a hypotonic borate/EDTA buffer at pH 10.1. The homogenate was centrifuged at 400 g for 10 minutes at 0°–4° C. The supernatant was centrifuged at 25,000 g for 30 minutes at 0°–4° C. The pelleted material was suspended in 30 mM Hepes buffer at pH 7.4 containing 5% glycerol, 4 mM benzamidine and 1% Triton X-100, stirred for 1 hour at 0°–4° C., and recentrifuged at 100,000 g for 1 hour at 0°–4° C. The supernatant, containing solubilised receptor tyrosine kinase, was stored in liquid nitrogen.

For test purposes 40 µl of the enzyme solution so obtained was added to a mixture of 400 µl of a mixture of 150 mM Hepes buffer at pH 7.4, 500 µM sodium orthovanadate, 0.1% Triton X-100, 10% glycerol, 200 µl water, 80 µl of 25 mM DTT and 80pl of a mixture of 12.5 mM manganese chloride, 125 mM magnesium chloride and distilled water. There was thus obtained the test enzyme solution.

Each test compound was dissolved in dimethylsulphoxide (DMSO) to give a 50 mM solution which was diluted with 40 mM Hepes buffer containing 0.1% Triton X-100, 10% glycerol and 10% DMSO to give a 500 µM solution. Equal volumes of this solution and a solution of epidermal growth factor (EGF; 20 µg/ml) were mixed.

[γ-$^{32}$P]ATP (3000 Ci/mM, 250 µCi) was diluted to a volume of 2 ml by the addition of a solution of ATP (100 µM) in distilled water. An equal volume of a 4 mg/ml solution of the peptide Arg-Arg-Leu-Ile-Glu-Asp-Ala-Glu-Tyr-Ala-Ala-Arg-Gly in a mixture of 40 mM Hepes buffer at pH 7.4, 0.1% Triton X-100 and 10% glycerol was added.

The test compound/EGF mixture solution (5 µl) was added to the test enzyme solution (10 µl) and the mixture was incubated at 0°–4° C. for 30 minutes. The ATP/peptide mixture (10 µl) was added and the mixture was incubated at 25° C. for 10 minutes. The phosphorylation reaction was terminated by the addition of 5% trichloroacetic acid (40 µl) and bovine serum albumin (BSA; 1 mg/ml, 5 µl). The mixture was allowed to stand at 4° C. for 30 minutes and then centrifuged. An aliquot (40 µl) of the supernatant was placed onto a strip of Whatman p 81 phosphocellulose paper. The strip was washed in 75 mM phosphoric acid (4×10 ml) and blotted dry. Radioactivity present in the filter paper was measured using a liquid scintillation counter (Sequence A). The reaction sequence was repeated in the absence of the EGF (Sequence B) and again in the absence of the test compound (Sequence C).

Receptor tyrosine kinase inhibition was calculated as follows:

$$\% \text{ Inhibition} = \frac{100 - (A - B)}{C - B} \times 100$$

The extent of inhibition was then determined at a range of concentrations of test compound to give an $IC_{50}$ value.

(b) An in vitro assay which determines the ability of a test compound to inhibit the growth of the human naso-pharyngeal cancer cell line KB.

KB cells were seeded into wells at a density of $1 \times 10^4$–$1.5 \times 10^4$ cells per well and grown for 24 hours in DMEM supplemented with 5% FCS (charcoal-stripped). Cell growth was determined after incubation for 3 days by the extent of metabolism of MTT tetrazolium dye to furnish a bluish colour. Cell growth was then determined in the presence of EGF (10 ng/ml) or in the presence of EGF (10 ng/ml) and a test compound at a range of concentrations. An $IC_{50}$ value could then be calculated.

(c) An in vivo assay in a group of male rats which determines the ability of a test compound (usually administered orally as a ball-milled suspension in 0.5% polysorbate) to inhibit the stimulation of liver hepatocyte growth caused by the administration of the growth factor TGFα (400 µg/kg subcutaneously, usually dosed twice, 3 and 7 hours respectively after the administration of the test compound).

In a control group of rats, the administration of TGFα causes on average a 5-fold stimulation of liver hepatocyte growth.

Cell-growth in the control and test animals is determined as follows:

On the morning of the day after the dosing of the test compound (or 0.5% polysorbate in the control group), the animals are dosed with bromodeoxyuridine (BrdU; 100 mg/kg intraperitoneally). The animals are killed four hours later and the livers are excised. Slices are cut from each liver and the uptake of BrdU is determined by a conventional immunohistochemical technique similar to that described on pages 267 and 268 of an article by Goldsworthy et al. in Chemically Induced Cell Proliferation: Implications for Risk Assessment, Wiley-Liss Inc., 1991, pages 253–284. Further tests were carried out using a range of doses of the test compounds to allow the calculation of an approximate $ED_{50}$ value for the inhibition of liver hepatocyte proliferation as determined by inhibition of the uptake of BrdU.

Although the pharmacological properties of the compounds of the formula I vary with structural change as expected, in general activity possessed by compounds of the formula I may be demonstrated at the following concentrations or doses in one or more of the above tests (a), (b) and (c):

Test (a): $IC_{50}$ in the range, for example, 0.0005–1 µM;

Test (b): $IC_{50}$ in the range, for example, 0.01–10 µM;

Test (c): $ED_{50}$ in the range, for example, 1–100 mg/kg.

Thus, by way of example, the compound 6,7-dimethoxy-4-(3'-methylanilino)quinazoline has an $IC_{50}$ of 0.005 µM in Test (a), an $IC_{50}$ of 0.05 µM in Test (b) and an $ED_{50}$ of <5 mg/kg in Test (c); the compound 6,7-dimethoxy-4-(3'-trifluoromethylanilino)quinazoline has an $IC_{50}$ of 0.01 µM in Test (a) and an $IC_{50}$ of 0.3 µM in Test (b); the compound 6-amino-4-(3'-methylanilino)quinazoline has an $IC_{50}$ of 0.055 µM in Test (a), an $IC_{50}$ of 1 µM in Test (b) and an $ED_{50}$ of <5 mg/kg in Test (c); the compound 6-acetamido-4-(3'-methylanilino)quinazoline has an $IC_{50}$ of 0.01 µM in Test (a) and an $IC_{50}$ of 0.65 µM in Test (b); and the compound 7-(2-hydroxyethoxy)-6-methoxy-4-(3'-methylanilino)quinazoline has an $IC_{50}$ of 0.005 µM in Test (a) and an $IC_{50}$ of 0.14 µM in Test (b).

As stated hereinbefore the compound 4-anilino-6,7-dimethoxyquinazoline is known and is stated to possess bronchodilator and/or hypotensive properties. There is no disclosure that the other quinazoline derivatives excluded from the definition of the invention possess pharmacological properties.

According to a further aspect of the invention there is provided a pharmaceutical composition which comprises a quinazoline derivative of the formula I, or a pharmaceutically-acceptable salt thereof, as defined hereinbefore or a quinazoline derivative selected from 4-(4'-hydroxyanilino)-6-methoxyquinazoline, 4-(4'-hydroxyanilino)- 6,7-methylenedioxyquinazoline, 4-(4'-hydroxyanilino)-6,7,8-trimethoxyquinazoline, 6-amino-4-(4'-aminoanilino)quinazoline and 4-anilino-6-methylquinazoline or the hydrochloride salt thereof, in association with a pharmaceutically-acceptable diluent or carrier.

The composition may be in a form suitable for oral administration, for example as a tablet or capsule, for parenteral injection (including intraveous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The quinazoline will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a quinazoline derivative of the formula I as defined hereinbefore for use in a method of treatment of the human or animal body by therapy.

We have now found that the compounds of the present invention and those known compounds excluded from the definition of the compounds of the invention possess anti-cancer properties which are believed to arise from their receptor tyrosine kinase inhibitory activity.

Thus according to this aspect of the invention there is provided the use of a quinazoline derivative of the formula I, or a pharmaceutically-acceptable salt thereof, as defined hereinbefore or a quinazoline derivative selected from 4-(4'-hydroxyanilino)-6-methoxyquinazoline, 4-(4'-hydroxyanilino)-6,7-methylenedioxyquinazoline, 4-(4'-hydroxyanilino)-6,7,8-trimethoxyquinazoline, 6-amino-4-{4'-aminoanilino)quinazoline, 4-anilino-6-methylquinazoline or the hydrochloride salt thereof and 4-anilino-6,7-dimethoxyquinazoline or the hydrochloride salt thereof in the manufacture of a medicament for use in the production of an anti-cancer effect in a warm-blooded animal such as man.

According to a further feature of this aspect of the invention there is provided a method for producing an anti-cancer effect in a warm-blooded animal, such as man, in need of such treatment which comprises administering to said animal an effective amount of a quinazoline derivative as defined immediately above.

As stated above the size of the dose required for the therapeutic or prophylactic treatment of a particular cancer will necessarily be varied depending on the host treated, the route of administration and the severity of the illness being treated. A unit dose in the range, for example, 1–100 mg/kg, preferably 1–50 mg/kg is envisaged.

The anti-cancer treatment defined hereinbefore may be applied as a sole therapy or may involve, in addition to the quinazoline derivative of the invention, one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred antimetabolites disclosed in European Patent Application No. 239362 such as N-{5-[N-(3,4-dihydro-2-methyl-4-oxoquinazolin-6-ylmethyl)-N-methylamino]-2-thenoyl}-L-glutamic acid; intercalating antibiotics, for example adriamycin and bleomycin; enzymes, for example asparaginase; topoisomerase inhibitors, for example etoposide; biological response modifiers, for example interferon; and anti-hormones, for example anti-oestrogens such as 'NOLVADEX' (tamoxifen) or, for example antiandrogens such as 'CASODEX' (4'-cyano-3-(4-fluorophenylsulphonyl)-2-hydroxy-2-methyl-3' -(trifluoromethyl)propionanilide. Such conjoint treatment may be achieved by way of the simultaneous, sequential or separate dosing of the individual components of the treatment. According to this aspect of the invention there is provided a pharmaceutical product comprising a quinazoline derivative of the formula I as defined hereinbefore or a quinazoline derivative selected from 4-(4'-hydroxyanilino)-6-methoxyquinazoline, 4-(4'-hydroxyanilino)-6,7-methylenedioxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof and an additional anti-tumour substance as defined hereinbefore for the conjoint treatment of cancer.

As stated above the quinazoline derivative defined in the present invention is an effective anti-cancer agent, which property is believed to arise from its receptor tyrosine kinase inhibitory properties. Such a quinazoline derivative of the invention is expected to possess a wide range of anti-cancer properties as receptor tyrosine kinases have been implicated in many common human cancers such as leukaemia and breast, lung, colon, rectal, stomach, prostate, bladder, pancreas and ovarian cancer. Thus it is expected that a quinazoline derivative of the invention will possess anti-cancer activity against these cancers. It is in addition expected that a quinazoline of the present invention will possess activity against a range of leukaemias, lymphoid malignancies and solid tumours such as carcinomas and sarcomas in tissues such as the liver, kidney, prostate and pancreas.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multilicities are shown as follows: s, singlet; d, doublet; t, triplet; m, multiplet;

(vii) intermediates were not generally fully characterised and purity was assessed by thin layer chromatography (TLC), infra-red (IR) or NMR analysis;

(viii) the following abbreviations have been used:

DMF N,N-dimethylformamide;

DMA N,N-dimethylacetamide;

THF tetrahydrofuran.

EXAMPLE 1

A mixture of 4-chloro-6,7-dimethoxyquinazoline (0.3 g), 3-methylaniline (0.143 g) and isopropanol (5 ml) was stirred and heated to reflux for 1 hour. The mixture was cooled to ambient temperature. The precipitate was filtered off and washed with cold isopropanol and with diethyl ether. There was thus obtained 6,7-dimethoxy-4-(3'-methylanilino-)quinazoline hydrochloride (0.226 g, 51%), m.p. 248°–249° C.

NMR Spectrum: ($CD_3SOCD_3$) 2.36 (s, 3H), 3.99 (s, 3H), 4.02 (s, 3H), 7.13 (d, 1H), 7.38 (s, 1H), 7.39 (t, 1H), 7.49 (s, 2H), 8.34 (s, 1H), 8.80 (s, 1H);

Elemental Analysis: Found C, 61.4; H, 5.4; N, 12.5;

$C_{17}H_{17}N_3O_2$. HCl requires C, 61.4; H, 5.4; N, 12.7%.

The 4-chloro-6,7-dimethoxyquinazoline used as a starting material was obtained as follows:

A mixture of 4,5-dimethoxyanthranilic acid (19.7 g) and formamide (10 ml) was stirred and heated to 190° C. for 5 hours. The mixture was allowed to cool to approximately 80° C. and water (50 ml) was added. The mixture was stored at ambient temperature for 3 hours. The precipitate was isolated, washed with water and dried. There was thus obtained 6,7-dimethoxyquinazolin-4-one (3.65 g).

A mixture of a portion (2.06 g) of the material so obtained, thionyl chloride (20 ml) and DMF (1 drop) was stirred and heated to reflux for 2 hours. The mixture was evaporated and the residue was partitioned between ethyl acetate and a saturated aqueous sodium bicarbonate solution. The organic phase was washed with water, dried ($MgSO_4$) and evaporated. The residue was purified by column chromatography using increasingly polar mixtures of methylene chloride and ethyl acetate as eluent. There was thus obtained the required starting material (0.6 g, 27%).

EXAMPLE 2

The procedure described in Example 1 was repeated except that the appropriate aniline was used in place of 3-methylaniline and, where appropriate, the appropriate substituted 4-chloroquinazoline was used in place of 4-chloro-6,7-dimethoxyquinazoline. There were thus obtained, as hydrochloride salts, the compounds described in the following table, the structures of which were confirmed by proton magnetic resonance spectroscopy and by elemental analysis.

TABLE I

| Example 2 Compd. No. | $(R^1)_m$ | $R^2$ | m.p. (°C.) |
| --- | --- | --- | --- |
| 1 | 6,7-dimethoxy | 3'-chloro | 245–247 |
| 2[a] | 6,7-dimethoxy | 3'-bromo | >250 (decomposes) |
| 3[b] | 6,7-methylenedioxy | 3'-methyl | >280 |
| 4[c] | 7-methoxy | 3'-methyl | 232–233 |
| 5[d] | 7-methoxycarbonyl | 3'-methyl | 206–211 |

Notes a. The product gave the following analytical data: Found C, 48.3; H, 3.6; N, 10.4; $C_{16}H_{14}BrN_3O_2$. HCl requires C, 48.4; H, 3.8; N, 10.6%; and the following characteristic NMR data: $(CD_3SOCD_3)$ 4.0 (s, 3H), 4.22 (s, 3H), 7.36 (s, 1H), 7.5 (m, 2H), 7.76 (m, 1H), 8.02 (m, 1H), 8.35 (s, 1H), 8.66 (s, 1H).

b. The product gave the following analytical data: Found C, 60.3; H, 4.3; N, 13.3; $C_{16}H_{13}N_3O_2$. 1.08 HCl requires C, 60.2, H, 4.4; N, 13.2%.

and the following characteristic NMR data $(CD_3SOCD_3)$ 2.36 (s, 3H), 6.37 (s, 2H), 7.13 (d, 2H), 7.35 (t, 1H), 7.37 (s, 1H), 7.49 (m, 2H), 8.28 (s, 1H), 8.78 (s, 1H).

The 4-chloro-6,7-methylenedioxyquinazoline used as a starting material was obtained from 4,5-methylenedioxyanthranilic acid using analogous procedures to those described in the portion of Example 1 which is concerned with the preparation of starting materials.

c. The 4-chloro-7-methoxyquinazoline used as a starting material was obtained from 4-methoxyanthranilic acid using analogous procedures to those described in the portion of Example 1 which is concerned with the preparation of starting materials.

d. The reaction mixture was heated to reflux for 2 hours. A precipitate was not deposited when the mixture was cooled to ambient temperature. The mixture was poured into water (50 ml) and a saturated aqueous ammonium hydroxide solution was added dropwise. The resultant precipitate was isolated, washed with water and dried. There was thus obtained 7-methoxycarbonyl-4-(3'-methylanilino)quinazoline in 47% yield.

The product gave the following analytical data: Found C, 69.8; H, 5.2; N, 13.9; $C_{17}H_{15}N_3O_2$ requires C, 69.6; H, 5.2; N, 14.3%;

and the following characteristic NMR data: $(CD_3SOCD_3)$ 2.36 (s, 3H), 3.95 (s, 3H), 6.98 (d, 1H), 7.29 (t, 1H), 7.67 (m, 2H), 8.08 (m, 1H), 8.29 (d, 1H), 8.68 (s, 1H), 8.70 (s, 1H).

The 4-chloro-7-methoxycarbonylquinazoline used as a starting material was obtained as follows:

Using an analogous procedure to that described in the first paragraph of the portion of Example 1 which is concerned with the preparation of starting materials, 4-carboxyanthranilic acid (14.2 g) was reacted with formamide to give 7-carboxyquinazolin-4-one (8.5 g). A mixture of a portion (4 g) of the material so obtained, methanol (40 ml) and concentrated sulphuric acid (2 ml) was stirred and heated to reflux for 6 hours. The mixture was cooled to ambient temperature and the precipitate was isolated. There was thus obtained 7-methoxycarbonylquinazolin-4-one (5.7 g).

A mixture of a portion (0.5 g) of the material so obtained, phosphoryl chloride (2 ml) and DMF (1 drop) was stirred and heated to reflux for 2 hours. The mixture was evaporated to give 4-chloro-7-methoxycarbonylquinazoline which was used without further purification.

EXAMPLE 3

A mixture of 4-chloro-6-methylquinazoline (0.5 g), 3-methylaniline (0.33 g) and isopropanol (10 ml) was stirred and heated to reflux for 1 hour. The mixture was cooled to ambient temperature. The precipitate was filtered off and washed with cold isopropanol and with diethyl ether. There was thus obtained 6-methyl-4-(3'-methylanilino)quinazoline (0.61 g, 76%), m.p. 243°–245° C.

NMR Spectrum: $(CD_3SOCD_3)$ 2.38 (s, 3H), 2.57 (s, 3H), 7.1–8.0 (m, 6H), 8.77 (s, 1H), 8.88 (s, 1H);

Elemental Analysis: Found C, 67.0; H, 5.5; N, 14.5; $C_{16}H_{15}N_3$. HCl requires C, 67.2; H, 5.6; N, 14.7%.

The 4-chloro-6-methylquinazoline used as a starting material was obtained as follows:

A mixture of 6-methylquinazolin-4-one (10 g; *J. Med. Chem.*, 1989, 32, 847), phosphoryl chloride (12.5 ml), N,N-dimethylaniline (14.25 ml) and toluene (150 ml) was stirred and heated to reflux for 2.5 hours. The mixture was poured onto ice and the organic layer was separated, washed with water, dried ($MgSO_4$) and evaporated. There was thus obtained the required starting material as a solid (10.4 g, 93%) which was used without further purification.

EXAMPLE 4

A mixture of 7-methoxy-4-(3'-methylanilino)quinazoline (0.106 g), sodium ethanethiolate (0.336 g) and DMF (5 ml) was stirred and heated to 140° C. for 4 hours. The mixture was evaporated and the residue was purified by column chromatography using a 45:55:0.2 v/v mixture of water, methanol and trifluoroacetic acid as eluent. There was thus obtained 7-hydroxy-4-(3'-methylanilino)quinazoline (0.068 g, 41%), m.p. 52°–60° C.

Elemental Analysis: Found C, 51.6; H, 3.6; N, 10.3; $C_{15}H_{13}N_3O$. $1.4CF_3CO_2H$ requires C, 52.0; H, 3.5; N, 10.2%.

EXAMPLE 5

Using an analogous procedure to that described in Example 4, 6,7-dimethoxy-4-(3'-chloroanilino)quinazoline was reacted with sodium ethanethiolate to give 6,7-dihydroxy-4-(3'-chloroanilino)quinazoline in 68% yield, m.p. 233°–235° C.

Elemental Analysis: Found C, 46.3; H, 2.7; N, 10.0;

$C_{14}H_{10}ClN_3O_2$. $1.18CF_3CO_2H$ requires C, 46.6; H, 2.7; N, 10.0%.

EXAMPLE 6

The procedure described in Example 1 was repeated except that the appropriate aniline was used in place of 3-methylaniline and, where appropriate, the appropriate substituted 4-chloroquinazoline was used in place of 4-chloro-6,7-dimethoxyquinazoline. There were thus obtained, as hydrochloride salts, the compounds described in the following table, the structures of which were confirmed by proton magnetic resonance spectroscopy and by elemental analysis.

TABLE II

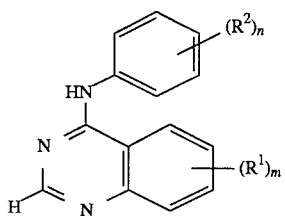

| Example 6 Compd. No. | $(R^1)_m$ | $(R^2)_n$ | m.p. (°C.) |
|---|---|---|---|
| 1[a] | 6,7-dimethoxy | 3'-trifluoromethyl | 261–262 |
| 2[b] | 6,7-dimethoxy | 4'-fluoro-3'-trifluoromethyl | 260–261 |
| 3[c] | 6,7-dimethoxy | 4'-fluoro | 227–230 |
| 4[d,e] | 6,7-dimethyl | 3'-methyl | 263–272 |
| 5[d,f] | 6,7-dimethyl | 3'-chloro | — |
| 6[g] | 6-dibromomethyl | 3'-methyl | 247–252 |

Notes a. The product gave the following analytical data: Found C, 52.9; H, 4.0; N, 10.6; $C_{17}H_{14}F_3N_3O_2$. HCl. $0.1(CH_3)_2CHOH$ requires C, 53.0; H, 4.0; N, 10.7%; and the following characteristic NMR data: $(CD_3SOCD_3)$ 4.0 (s, 3H), 4.03 (s, 3H), 7.37 (s, 1H), 7.64 (d, 1H), 7.73 (t, 1H), 8.09 (d, 1H), 8.16 (s, 1H), 8.39 (s, 1H), 8.89 (s, 1H), 11.59 (broad s, 1H).

b. The product gave the following analytical data: Found C, 50.3; H, 3.7; N, 9.9; $C_{17}H_{13}F_4N_3O_2$. HCl. 0.5EtOH requires C, 50.7; H, 3.6; N, 9.9%; and the following characteristic NMR data: $(CD_3SOCD_3)$ 4.0 (s, 3H), 4.03 (s, 3H), 7.37 (s, 1H), 7.65 (t, 1H), 8.1–8.25 (m, 2H), 8.44 (s, 1H), 8.89 (s, 1H), 11.76 (s, 1H).

c. The product, obtained initially as the hydrochloride salt, was converted into the corresponding free base as follows: The salt was partitioned between ethyl acetate and 1N aqueous sodium hydroxide solution. The organic phase was washed with brine, dried (MgSO$_4$) and evaporated. The material so obtained was triturated under ethyl acetate. There was thus obtained the required free base, m.p. 227°–230° C.;

NMR Spectrum: $(CD_3SOCD_3)$ 3.94 (s, 3H), 3.98 (s, 3H), 7.16–7.25 (m, 3H), 7.7–7.8 (m, 3H), 8.40 (s, 1H), 9.5 (s, 1H);

Elemental Analysis: Found C, 64.1; H, 4.7; N, 13.8; $C_{16}H_{14}FN_3O_2$ requires C, 64.2; H, 4.7; N, 14.0%.

d. Two equivalents of triethylamine were added to the reaction mixture prior to the reaction mixture being heated to reflux for 3 hours. The mixture was cooled to ambient temperature and partitioned between methylene chloride and water. The organic phase was dried (MgSO$_4$) and evaporated. The residue was recrystallised from isopropanol to give the required product.

e. The product gave the following analytical data: Found C, 70.7; H, 6.3; N, 14.3; $C_{17}H_{17}N_3$. 0.7HCl requires C, 70.7; H, 6.15; N, 14.5%;

and the following characteristic NMR data: $(CD_3SOCD_3)$ 2.36 (s, 3H), 2.5 (s, 6H), 7.1–7.7 (m, 5H), 8.56 (s, 1H), 8.77 (s, 1H).

The 4-chloro-6,7-dimethylquinazoline used as a starting material was obtained from 4,5-dimethylanthranilic acid (*Acta Chemica Scand.*, 1967, 21, 983) using analogous procedures to those described in the portion of Example 1 which is concerned with the preparation of starting materials.

f. The product gave the following analytical data: Found C, 58.2; H, 5.9; N, 10.6; $C_{16}H_{14}ClN_3$. 1.3 HCl. $0.8(CH_3)_2CHOH$ requires C, 58.2; H, 5.8; N, 11.0%;

and the following characteristic NMR data: $(CD_3SOCD_3)$ 2.5 (s, 6H), 7.37 (m, 1H), 7.51 (t, 1H), 7.73 (s, 1H), 7.78 (m, 1H), 7.96 (t, 1H), 8.74 (s, 1H), 8.92 (s, 1H), 11.5 (broad s, 1H).

g. The product gave the following analytical data: Found C, 41.4; H, 3.4; N, 9.1; $C_{16}H_{13}BrN_3$. HCl. $1.1H_2O$ requires C, 41.4; H, 3.5; N, 9.1;

and the following characteristic NMR data: $(CD_3SOCD_3)$ 2.38 (s, 3H), 7.18 (d, 1H), 7.40 (t, 1H), 7.49 (m, 2H), 7.51 (s, 1H), 7.94 (d, 1H), 8.29 (m, 1H), 8.91 (s, 1H), 9.10 (d, 1H), 11.7 (s, 1H).

The 4-chloro-6-dibromomethylquinazoline used as a starting material was obtained as follows:

A mixture of 4-chloro-6-methylquinzoline (7.3 g) [obtained by the reaction 6-methyl-4-oxo-3,4-dihydroquinazoline (European Patent Application No. 86304148.9) with thionyl chloride], N-bromosuccinimide (7.32 g) dibenzoyl peroxide (0.1 g) and carbon tetrachloride (200 ml) was stirred and heated to reflux for 6 hours. The mixture was evaporated and the residue was purified by column chromatography using increasingly polar mixtures of methylene chloride and ethyl acetate as eluent. There were thus obtained in turn 4-chloro-6-dibromomethylquinazoline (0.5 g) and 6-bromomethyl-4-chloroquinazoline (4 g).

EXAMPLE 7

Ammonium formate (3.6 g) was added to a stirred mixture of 4-(3'-methylanilino)-7-nitroquinazoline (4 g), 10% palladium-on-charcoal catalyst (0.4 g) and ethanol (200 ml) and the mixture was stirred at ambient temperature for 3 hours. The mixture was filtered and the filtrate was evaporated. The residue was partitioned between methylene chloride and water. The organic phase was dried (MgSO$_4$) and evaporated. The residue was recrystallised from ethanol. There was thus obtained 7-amino-4-(3'-methylanilino)quinazoline (3.39 g), m.p. 196°–197° C.

NMR Spectrum: $(CD_3SOCD_3)$ 2.32 (s, 3H), 5.96 (broad s, 2H), 6.7–6.9 (m, 3H), 7.23 (t, 1H), 7.6 (m, 2H), 8.21 (d, 1H), 8.38 (s, 1H);

Elemental Analysis: Found C, 69.1; H, 6.8; N, 19.0; $C_{15}H_{14}N_4$. $C_2H_5OH$ requires C, 69.1; H, 6.8; N, 18.9%.

The 4-(3'-methylanilino)-7-nitroquinazoline used as a starting material was obtained as follows:

Using an analogous procedure to that described in the portion of Example 1 which is concerned with the preparation of starting materials, 4-nitroanthranilic acid was converted into 4-chloro-7-nitroquinazoline. Using an analogous procedure to that described in Example 1 except that the reactants were stirred together at ambient temperature for 20 minutes, 4-chloro-7-nitroquinazoline was reacted with 3-methylaniline to give 4-(3'-methylanilino)-7-nitroquinazoline.

EXAMPLE 8

Using an analogous procedure to that described in Example 7, 4-(3'-methylanilino)-6-nitroquinazoline was reduced to give 6-amino-4-(3'-methylanilino)quinazoline in 43% yield, m.p. 205°–206° C. NMR Spectrum: ($CD_3SOCD_3$) 2.32 (s, 3H), 5.6 (broad s, 2H), 6.8 (d, 1H), 7.2–7.7 (m, 6H), 8.34 (s, 1H);

Elemental Analysis: Found C, 71.7; H, 5.7; N, 22.4; $C_{15}H_{14}N_4$ requires C, 72.0; H, 5.6; N, 22.4%.

The 4-(3'-methylanilino)-6-nitroquinazoline used as a starting material was obtained as follows:

Using an analogous procedure to that described in the first paragraph of the portion of Example 1 which is concerned with the preparation of starting materials, 5-nitroanthranilic acid was reacted with formamide to give 6-nitroquinazolin-4-one in 82% yield, m.p. 268°–271° C.

A mixture of 6-nitroquinazolin-4-one (10 g), phosphorus pentachloride (16.4 g) and phosphoryl chloride (20 ml) was heated to reflux for 2 hours. The mixture was cooled to ambient temperature and hexane (700 ml) was added. The mixture was stored at 0° C. for 16 hours. The precipitate was isolated and partitioned between chloroform (700 ml) and water (550 ml). The aqueous layer was basified by the addition of 2N aqueous sodium hydroxide solution and extracted with chloroform (2×200 ml). The combined organic solutions were dried ($MgSO_4$) and evaporated. There was thus obtained 4-chloro-6-nitroquinazoline (1.6 g) which was used without further purification.

3-Methylaniline (0.139 g) was added to a mixture of 4-chloro-6-nitroquinazoline (0.25 g) and isopropanol (5 ml) and the mixture was stirred and heated to reflux for 2 hours. The mixture was cooled to ambient temperature and evaporated. The residue was purified by column chromatography using increasingly polar mixtures of hexane and ethyl acetate as eluent. There was thus obtained an oil which solidified on trituration under a mixture of diethyl ether and isopropanol. There was thus obtained 4-(3'-methylanilino)-6-nitroquinazoline (0.09 g, 26%), m.p. 248°–249° C. Mass Spectrum: (P+I) m/e 281.

Elemental Analysis: Found C, 64.0; H, 4.5; N, 18.6; $C_{15}H_{12}N_4O_2$. $0.25(CH_3)_2CHOH$ requires C, 64.1; H, 4.8; N, 18.9%.

EXAMPLE 9

Using an analogous preocedure to that described in Example 7, 4-(3'-chloroanilino)-6-nitroquinazoline was reduced to give 6-amino-4-(3'-chloroanilino)quinazoline in 18% yield, m.p. >150° C. (decomposes).

NMR Spectrum: ($CD_3SOCD_3$) 7.27 (m, 1H), 7.39 (d, 1H}, 7.45 (m, 2H), 7.66 (d, 1H), 7.74 (d, 1H), 7.97 (t, 1H), 8.60 (s, 1H);

Elemental Analysis: Found C, 56.4; H, 4.5; N, 18.4; $C_{14}H_{11}ClN_4$. 0.5 HCl. $0.5H_2O$ requires C, 56.4; H, 4.2; N, 18.8%.

The 4-(3'-chloroanilino)-6-nitroquinazoline used as a starting material was obtained as follows:

Triethylamine (2.53 g) and 3-chloroaniline (3.35 g) were added in turn to a stirred mixture of 4-chloro-6-nitroquinazoline (5 g) and isopropanol (40 ml). The mixture was stirred and heated to 80° C. for 1 hour. The mixture was cooled to ambient temperature and the precipitate was isolated and washed with diethyl ether. There was thus obtained the required starting material (5.09 g), m.p. 272°–274° C.

EXAMPLE 10

Using an analogous procedure to that described in Example 7, 6-nitro-4-(3'-trifluoromethylanilino)quinazoline was reduced to give 6-amino-4-(3'-trifluoromethylanilino)quinazoline in 38% yield, m.p. 190°–192° C.

NMR Spectrum: ($CD_3SOCD_3$) 5.7 (broad s, 2H), 7.28 (m, 1H), 7.38 (d, 1H), 7.40 (d, 1H), 7.6 (m, 2H), 8.23 (d, 1H), 8.35 (s, 1H), 8.42 (s, 1H);

Elemental Analysis: Found C, 57.4; H, 3.6; N, 17.6; $C_{15}H_{11}F_3N_4$. $0.5H_2O$ requires C, 57.5; H, 3.8; N, 17.9%.

The 6-nitro-4-(3'-trifluoromethylanilino)quinazoline used as a starting material was obtained as follows:

Triethylamine (3.46 g) and 3-trifluoromethylaniline (3.46 g) were added in turn to a stirred mixture of 4-chloro-6-nitroquinazoline (4.5 g) and isopropanol (30 ml). The mixture was heated to 80° C. for 1 hour. The mixture was cooled to ambient temperature and partitioned between methylene chloride and water. The organic phase was dried ($MgSO_4$) and evaporated. The residue was purified by column chromatography using increasingly polar mixtures of methylene chloride and ethyl acetate as eluent. There was thus obtained the required starting material (1.76 g), m.p. 206°–207° C.

EXAMPLE 11

Acetic anhydride (0.204 g) was added to a stirred solution of 6-amino-4-(3'-methylanilino)quinazoline (0.5 g) in DMA (5 ml) and the mixture was stirred at ambient temperature for 24 hours. The mixture was evaporated and the residue was recrystallised from a 4:1:2 mixture of isopropanol, acetone and water. There was thus obtained 6-acetamido-4-(3'-methylanilino)quinazoline (0.413 g).

NMR Spectrum: ($CD_3SOCD_3$) 2.12 (s, 3H), 2.33 (s, 3H), 6.93 (d, 1H), 7.28 (t, 1H), 7.6 (m, 2H), 7.73 (d, 1H), 7.84 (m, 1H), 8.49 (s, 1H), 8.64 (d, 1H), 9.68 (s, 1H);

Elemental Analysis: Found C, 69.6; H, 5.5; N, 19.1; $C_{17}H_{16}N_4O$ requires 69.8; H, 5.5; N, 19.2%.

EXAMPLE 12

Using an analogous procedure to that described in Example 11, 6-amino-4-(3'-chloroanilino)quinazoline was reacted with acetic anhydride to give 6-acetamido-4-(3'-chloroanilino)quinazoline in 50% yield, m.p. 260°–262° C.

NMR Spectrum: ($CD_3SOCD_3$) 2.13 (s, 3H), 7.13 (m, 1H), 7.39 (t, 1H), 7.8 (m, 3H), 8.03 (s, 1H), 8.56 (s, 1H), 8.66 (d, 1H), 9.87 (broad s, 1H), 10.24 (broad s, 1H);

Elemental Analysis: Found C, 61.2; H, 4.1; N, 18.0; $C_{16}H_{13}Cl_1N_4O$ requires C, 61.4; H, 4.2; N, 17.9%.

EXAMPLE 13

2-Methoxyacetyl chloride (0.094 g) was added to a stirred solution of 7-amino-4-(3'-methylanilino)quinazoline (0.206 g) in DMA (4 ml). The mixture was stirred and heated to 100° C. for 1 hour. The mixture was cooled to ambient temperature and poured into a mixture of methylene chloride and water. The mixture was basified to pH 9 by the addition of dilute aqueous sodium hydroxide solution. The organic layer was dried ($MgSO_4$) and evaporated. The residue was purified by column chromatography using initially a 100:1 mixture of methylene chloride and ethanol and then increasingly polar mixtures of methylene chloride and ethanol as eluent. There was thus obtained 7-(2-methoxyacetamido)-4-(3'-methylanilino)quinazoline (0.085 g), m.p. 222° C.

NMR Spectrum: $(CD_3SOCD_3)$ 2.34 (s, 3H), 3.42 (s, 3H), 4.08 (s, 2H), 6.9–7.9 (m, 4H), 8.21 (d, 1H), 8.48 (d, 1H), 8.52 (s, 1H), 9.6 (s, 1H), 10.2 (s, 1H);

Elemental Analysis: Found C, 66.6; H, 5.7; N, 17.0; $C_{18}H_{18}N_4O_2 \cdot 0.1H_2O$ requires C, 66.7; H, 5.6; N, 17.3%.

EXAMPLE 14

Using an analogous procedure to that described in Example 13 except that the reaction mixture was stirred at ambient temperature rather than being heated to 100° C., 6-amino-4-(3'-chloroanilino)quinazoline was reacted with 2-methoxyacetyl chloride to give 6-(2-methoxyacetamido)-4-(3'-chloroanilino)quinazoline in 41% yield, m.p. 177°–180° C.

NMR Spectrum: $(CD_3SOCD_3)$ 3.44 (s, 3H), 4.09 (s, 2H), 7.17 (m, 1H), 7.44 (t, 1H), 7.8 (m, 2H), 8.0 (m, 2H), 8.61 (s, 1H), 8.71 (d, 1H), 9.9 (s, 1H), 10.05 (s, 1H);

Elemental Analysis: Found C, 59.7; H, 4.4; N, 16.2; $C_{18}H_{18}N_4O_2$ requires C, 59.6; H, 4.4; N, 16.3%

EXAMPLE 15

Benzenesulphonyl chloride (0.158 g) was added to a stirred mixture of 7-amino-4-(3'-methylanilino)quinazoline (0.2 g), Eriethylamine (0.181 g) and methylene chloride (10 ml) which had been cooled to 3° C. The mixture was allowed to warm to ambient temperature and was stirred for 16 hours. The mixture was evaporated and the residue was purified by column chromatography using increasingly polar mixtures of methylene chloride and ethyl acetate as eluent. There was thus obtained 7-benzenesulphonamido-4-(3'-methylanilino)quinazoline (0.05 g), m.p. 180°–185° C. (decomposes).

Elemental Analysis: Found C, 61.5; H, 4.8; N, 13.4; $C_{21}H_{18}N_4O_2S \cdot H_2O$ requires C, 61.7; H, 4.4; N, 13.7%.

EXAMPLE 16

2-Bromoethanol (0.109 g) was added to a mixture of 7-amino-4-(3'-methylanilino)quinazoline (0.2 g), potassium carbonate (0.218 g) and DMA (6 ml). The mixture was stirred and heated to 110° C. for 1 hour. Further portions of 2-bromoethanol (3×0.109 g) were added periodically and the mixture was heated to 110° C. for 5 hours. The mixture was evaporated and the residue was purified by column chromatography using increasingly polar mixtures of methylene chloride and ethanol as eluent. The product so obtained was further purified by reverse phase column chromatography using initally a 25:75:0.2 mixture of methanol, water and trifluoroacetic acid and finally a 50:50:0.2 mixture of these solvents as eluent. There was thus obtained 7-(2-hydroxyethylamino)-4-(3'-methylanilino)quinazoline (0.027 g).

NMR Spectrum $(CD_3SOCD_3)$ 2.36 (s, 3H), 3.77 (t, 2H), 4.34 (t, 2H), 6.8–7.5 (m, 7H), 8.37 (d, 1H), 8.61 (s, 1H), 10.79 (s, 1H).

EXAMPLE 17

Using an analogous procedure to that described in Example 16, 6-amino-4-(3'-methylanilino)quinazoline was reacted with 2-bromoethyl methyl ether to give 6-(2-methoxyethylamino)-4-(3'-methylanilino)quinazoline in 20% yield, m.p. 163°–167° C.

NMR Spectrum: $(CD_3SOCD_3+CD_3CO_2D)$ 2.39 (s, 3H), 3.36 (s, 3H), 3.44 (t, 2H), 3.63 (t, 2H), 7.17 (d, 1H), 7.4–7.7 (m, 6H), 8.6 (s, 1H);

Elemental Analysis: Found C, 56.4; H, 5.0; N, 13.1; $C_{18}H_{20}N_4O \cdot CF_3CO_2H$ requires C, 56.8; H, 5.0; N, 13.3%.

EXAMPLE 18

Using an analogous procedure to that described in Example 7, 7-(3-dimethylaminopropylamino)-4-(3'-methylanilino)-6-nitroquinazoline was reduced to give 6-amino-7-(3-dimethylaminopropylamino)-4-(3,methylanilino)quinazoline in 56% yield, m.p. 60°–66° C.

NMR Spectrum: $(CD_3SOCD_3)$ 1.84 (m, 2H), 2.28 (s, 6H), 2.30 (s, 3H), 2.31 (m, 2H), 3.23 (m, 2H), 6.58 (s, 1H), 6.81 (d, 1H), 7.19 (t, 1H), 7.31 (s, 1H), 7.63 (m, 2H), 8.24 (s, 1H);

Elemental Analysis: Found C, 66.5; H, 7.6; N, 22.8; $C_{20}H_{26}N_6 \cdot 0.66H_2O$ requires C, 66.3; H, 7.6; N, 23.2%.

The 7-(3-dimethylaminopropylamino)-4-(3'-methylanilino)-6- nitroquinazoline used as a starting material was obtained as follows:

A mixture of 4-chloroanthranilic acid (17.2 g) and formamide (10 ml) was stirred and heated to 130° C. for 45 minutes and to 175° C. for 75 minutes. The mixture was allowed to cool to approximately 100° C. and 2-(2-ethoxyethoxy)ethanol (50 ml) was added. The solution so formed was poured into a mixture (250 ml) of ice and water. The precipitate was isolated, washed with water and dried. There was thus obtained 7-chloroquinazolin-4-one (15.3 g, 85%).

A portion (6 g) of the material so obtained was added portionwise to a stirred mixture of concentrated sulphuric acid (12 ml) and fuming nitric acid (12 ml). The mixture was heated to 110° C. for 30 minutes. The mixture was cooled to ambient temperature and poured onto ice. The solid was isolated, washed with water and dried. There was thus obtained 7-chloro-6-nitroquinazolin-4-one (6.89 g, 92%).

A mixture of a portion (4 g) of the material so obtained, thionyl chloride (30 ml), phosphoryl chloride (5 ml) and DMF (10 drops) was stirred and heated to reflux for 4 hours. The mixture was evaporated. A mixture of the residue, 3'-methylaniline (1.89 g) and isopropanol (25 ml) was stirred and heated to reflux for 2 hours. The mixture was filtered and the solid was washed with isopropanol and with diethyl ether. There was thus obtained 7-chloro-4-(3'-methylanilino)- 6-nitroquinazoline (3.74 g, 67%), m.p. 271°–274° C.

NMR Spectrum: $(CD_3SOCD_3)$ 2.37 (s, 3H), 7.13 (d, 1H), 7.47 (t, 1H), 7.57 (m, 2H), 8.20 (s, 1H), 8.83 (s, 1H), 9.72 (s, 1H).

3-Dimethylaminopropylamine (2.44 g) was added to a stirred solution of a portion (0.75 g) of the material so obtained in DMA (20 ml). The mixture was heated to 70° C. for 1 hour and to 90° C. for a further hour. The mixture was evaporated. The residue was triturated under water to give a solid. The solid was taken into hot methanol. Water was added and the solution was allowed to cool. The resultant precipitate was isolated and dried. There was thus obtained 7-(3-dimethylaminopropylamino)-4-(3'-methylanilino)-6-nitroquinazoline (0.47 g, 52%), m.p. 112°–118° C.

NMR Spectrum: $(CD_3SOCD_3)$ 1.61 (m, 2H), 2.2–2.3 (3 s's, 9H), 2.39 (t, 2H), 3.39 (m, 2H), 6.93 (s, 1H), 6.96 (d, 1H), 7.27 (t, 1H), 7.61 (s, 1H), 7.63 (d, 1H), 8.36 (t, 1H), 8.42 (s, 1H), 9.50 (s, 1H), 10.07 (broad s, 1H).

EXAMPLE 19

A mixture of 6,7-dimethoxy-4-(3'-methylanilino)quinazoline (4 g), sodium ethanethiolate (9.8 g) and DMF (100 ml) was stirred and heated to 80° C. for 6 hours. The mixture was cooled and poured into a mixture of ethyl acetate and water. The mixture was acidified to $pH_7$ by the addition of dilute aqueous hydrochloric acid. The organic phase was dried ($MgSO_4$) and evaporated. The residue was purified by column chromatography using increasingly polar mixtures of methylene chloride and methanol as eluent. The oil so obtained was triturated under diethyl ether to give a solid. There was thus obtained 7-hydroxy-6-methoxy-4-(3'-methylanilino)quinazoline (1.02 g), m.p. 139°–149° C.

NMR Spectrum: ($CD_3SOCD_3$) 2.35 (s, 3H), 3.97 (s, 3H), 6.90 (m, 1H), 7.05 (s, 1H), 7.26 (m, 1H), 7.5–7.7 (m, 2H), 7.84 (s, 1H), 8.39 (s, 1H), 9.34 (broad s, 1H);

Elemental Analysis: Found C, 66.5; H, 5.7; N, 13.7; $C_{16}H_{15}N_3O_2$. $0.15Et_2O$. $0.5H_2O$ requires C, 66.3; H, 5.5; N, 14.0%.

EXAMPLE 20

A mixture of 6,7-dimethoxy-4-(3'-methylanilino)quinazoline (4 g), sodium ethanethiolate (9.8 g) and DMF (100 ml) was stirred and heated to 80° C. for 3 hours. The mixture was cooled to ambient temperature and acidified to $pH_4$ by the addition of glacial acetic acid. The mixture was evaporated and the residue was purified by column chromatography using increasingly polar mixtures of methylene chloride and methanol as eluent. There was thus obtained 6-hydroxy-7-methoxy-4-(3'-methylanilino)quinazoline (0.3 g), m.p. 265°–267° C.

NMR Spectrum: ($CD_3SOCD_3$) 2.32 (s, 3H), 3.97 (s, 3H), 6.90 (m, 1H), 7.15–7.30 (m, 2H), 7.66 (m, 2H), 7.80 (s, 1H), 8.41 (s, 1H), 9.24 (broad s, 1H), 9.53 (broad s, 1H);

Elemental Analysis: Found C, 65.2; H, 5.2; N, 14.0; $C_{16}H_{15}N_3O_2$. $0.67H_2O$ requires C, 65.5; H, 5.6; N, 14.3%.

EXAMPLE 21

Ethyl bromoacetate (0.033 g) was added dropwise to a stirred mixture of 7-hydroxy-6-methoxy-4-(3'-methylanilino)quinazoline (0.05 g), potassium carbonate (0.074 g) and DMF (1 ml). The mixture was stirred at ambient temperature for 1 hour. The mixture was evaporated and the residue was purified by column chromatography using increasingly polar mixtures of methylene chloride and ethyl acetate as eluent. There was thus obtained 7-(ethoxycarbonylmethoxy)-6-methoxy- 4-(3'-methylanilino)quinazoline (0.051 g), m.p. 165°–168° C.

NMR Spectrum: ($CD_3SOCD_3$) 1.24 (t, 3H), 2.35 (s, 3H), 3.99 (s, 3H), 4.99 (q, 2H), 4.33 (s, 2H), 6.9–7.9 (m, 6H), 8.43 (s, 1H), 9.40 (s, 1H);

Elemental Analysis: Found C, 64.8; H, 5.9; N, 10.9; $C_{20}H_{21}N_3O_4$. $0.2H_2O$ requires C, 64.7; H, 5.8; N, 11.3%.

EXAMPLE 22

The procedure described in Example 21 was repeated except that 2-iodoacetamide was used in place of ethyl bromoacetate. There was thus obtained 7-(carbamoylmethoxy)-6-methoxy-4-(3'-methylanilino)quinazoline in 91% yield, m.p. 214°–222° C.

NMR Spectrum: ($CD_3SOCD_3$) 2.35 (s, 3H), 3.99 (s, 3H), 4.65 (s, 2H), 6.9–7.9 (m, 6H), 8.45 (s, 1H);

Elemental Analysis: Found C, 47.8; H, 4.9; N, 11.9; $C_{18}H_{18}N_4O_3$. 0.1HI requires C, 47.5; H, 4.8; N, 12.3%.

EXAMPLE 23

A mixture of 7-hydroxy-6-methoxy-4-(3'-methylanilino)quinazoline (0.556 g), 2-bromoethanol (0.153 ml), potassium carbonate (0.819 g) and DMF (10 ml) was stirred and heated to 80° C. for 3 hours. The mixture was evaporated and the residue was purified by column chromatography using a 19:1 mixture of ethyl acetate and methanol as eluent. The product was further purified by reverse phase chromatography using a 50:50:0.2 mixture of methanol, water and trifluoroacetic acid as eluent. There was thus obtained 7-(2-hydroxyethoxy)-6-methoxy-4-(3,-methylanilino)quinazoline (0.154 g), m.p. 122°–124° C.

NMR Spectrum: ($CD_3SOCD_3$) 2.35 (s, 3H), 3.81 (m, 2H), 3.97 (s, 3H), 4.17 (t, 2H), 6.9–7.9 (m, 6H), 8.45 (s, 1H);

Elemental Analysis: Found C, 52.9; H, 4.9; N, 8.7; $C_{18}H_{19}N_3O_3$. $1.1CF_3CO_2H$. $0.5H_2O$ requires C, 52.7; H, 4.6; N, 91%.

EXAMPLE 24

The procedure described in Example 21 was repeated except that 2-bromoethyl methyl ether was used in place of ethyl bromoacetate and that the reaction mixture was stirred at ambient temperature for 16 hours. There was thus obtained 6-methoxy-7-(2-methoxyethoxy)-4-( 3'-methylanilino)quinazoline as a colourless oil. The oil was dissolved in ethyl acetate (2 ml) and a saturated solution of hydrogen chloride in diethyl ether was added. There was thus obtained the hydrochloride salt of the product in an overall yield of 73%, m.p. 211°–227° C.

NMR Spectrum: ($CD_3SOCD_3$) 2.35 (s, 3H), 3.34 (s, 3H), 3.78 (q, 2H), 4.01 (s, 3H), 4.31 (q, 2H), 6.9–7.6 (m, 5H), 8.23 (s, 1H), 8.75 (s, 1H);

Elemental Analysis: Found C, 61.2; H, 6.0; N, 10.9; $C_{19}H_{21}N_3O_3$. 0.9 HCl requires C, 61.2; H, 5.9; N, 11.3%.

EXAMPLE 25

A mixture of 7-(ethoxycarbonylmethoxy)-6-methoxy-4-(3,methylanilino)quinazoline (0.262 g), 2N aqueous sodium hydroxide solution (2 ml) and 1,4-dioxan (2 ml) was stirred at ambient temperature for 3 hours. The mixture was acidified by the addition of 2N aqueous hydrochloric acid and the acidity was reduced to $pH_6$ by the addition of aqueous ammonium hydroxide solution. The precipitate was isolated and dried. There was thus obtained 7-(carboxymethoxy)-6-methoxy-4-(3'-methylanilino)quinazoline (0.159 g), m.p. 215°–222° C.

NMR Spectrum: ($CD_3SOCD_3$) 2.34 (s, 3H), 3.95 (s, 3H), 4.33 (s, 2H), 6.9–7.9 (m, 6H), 8.41 (s, 1H);

Elemental Analysis: Found C, 53.5; H, 5.0; N, 10.5; $C_{18}H_{16}NaN_3O_4$. $2.3H_2O$ requires C, 53.6; H, 5.1; N, 10.4%.

EXAMPLE 26

A mixture of 7-(2-hydroxyethoxy)-6-methoxy-4-(3,-methylanilino)quinazoline (0.23 g), DMF (1 drop) and thionyl chloride (5 ml) was heated to reflux for 2 hours. The mixture was evaporated.

The residue was dissolved in DMF (3 ml) and the solution was saturated with dimethylamine gas. The solution was stirred and heated to 100° C. for 3 hours. The mixture was evaporated and the residue was purified by reverse phase column chromatography using a 50:50:0.2 mixture of methanol, water and trifluoroacetic acid as eluent. There was thus obtained 7-(2-dimethylaminoethoxy)-6-methoxy-4-(3'-methylanilino)quinazoline (0.24 g), m.p. 97°–100° C.

NMR Spectrum: (CD$_3$SOCD$_3$) 2.37 (s, 3H), 2.93 (s, 6H), 3.66 (t, 2H), 3.98 (s, 3H), 4.57 (t, 2H), 7.1–8.2 (m, 6H), 8.78 (s, 1H), 10.82 (s, 1H);

Elemental Analysis: Found C, 46.4; H, 4.2; N, 8.8; C$_{20}$H$_{24}$N$_4$O$_2$. 2.6CF$_3$CO$_2$H requires C, 46.6; H, 4.1; N, 8.6%.

EXAMPLE 27

2-Iodoethanol (0.327 ml) was added to a mixture of 6,7-dihydroxy-4-(3'-methylanilino)quinazoline (0.534 g), potassium carbonate (1.1 g) and DMA (10 ml). The mixture was stirred at ambient temperature for 18 hours. The mixture was evaporated and the residue was purified by reverse phase column chromatography using a 50:50:0.2 mixture of methanol, water and trifluoroacetic acid as eluent. There was thus obtained 6,7-di-(2-hydroxyethoxy)-4-(3'-methylanilino)quinazoline (0.049 g), m.p. 96°–102° C.

NMR Spectrum: (CD$_3$SOCD$_3$) 2.37 (s, 3H), 3.85 (m, 4H), 4.23 (m, 4H), 7.05–7.55 (m, 5H), 8.06 (s, 1H), 8.76 (s, 1H), 10.78 (broad s, 1H);

Elemental Analysis: Found C, 49.2; H, 4.5; N, 7.9; C$_{19}$H$_{21}$N$_3$O$_4$. 1.6CF$_3$CO$_2$H requires C, 49.5; H, 4.2; N, 7.8%.

The 6,7-dihydroxy-4-(3'-methylanilino)quinazoline used as a starting material was obtained in 77% yield from 6,7-dimethoxy-4-(3'-methylanilino)quinazoline using an analogous procedure to that described in Example 4.

EXAMPLE 28

A solution of 6-bromomethyl-4-(3'-methylanilino)quinazoline in DMF (3 ml) was saturated with dimethylamine gas and the resultant solution was stirred at ambient temperature for 16 hours. The mixture was evaporated and the residue was purified by column chromatography using a 17:3 mixture of methylene chloride and methanol as eluent. The resultant solid (0.308 g) was further purified by reversed-phase column chromatography using a 3:2:0.01 mixture of water, methanol and trifluoroacetic acid as eluent. There was thus obtained 6-dimethylaminomethyl-4-(3'-methylanilino)quinazoline (0.172 g), m.p. 174°–177° C.

NMR Spectrum: (CD$_3$SOCD$_3$) 2.35 (s, 3H), 2.85 (s, 6H), 4.47 (s, 2H), 7.0–8.1 (m, 6H), 8.66 (d, 1H), 8.85 (s, 1H);

Elemental Analysis: Found C, 49.2; H, 4.2; N, 10.4; C$_{18}$H$_{20}$N$_4$. 2.25CF$_3$CO$_2$H requires C, 49.2; H, 4.1; N, 10.2%.

EXAMPLE 29

Using an analogous procedure to that described in Example 28, 6-bromomethyl-4-chloroquinazoline was reacted with 3-methylaniline and the product so formed was reacted with piperazine. There was thus obtained 4-(3'-methylanilino)-6-(piperazin-1-ylmethylquinazoline in 45% yield, m.p. 175°–178° C.

NMR Spectrum: (CD$_3$SOCD$_3$) 2.38 (s, 3H), 2.73 (m, 4H), 3.17 (m, 4H), 3.86 (s, 2H), 7.1–8.1 (m, 6H), 8.66 (d, 1H), 8.90 (s, 1H);

Elemental Analysis: Found C, 43.0; H, 3.7; N, 9.0; C$_{20}$H$_{23}$N$_5$. 3.9CF$_3$CO$_2$H requires C, 42.9; H, 3.5; N, 9.0%.

EXAMPLE 30

Using an analogous procedure to that described in Example 28, 6-bromomethyl-4-chloroquinazoline (0.5 g) was reacted with 3-methylaniline (0.204 g). A mixture of the product so formed and the sodium salt of 2-mercaptoethanol [prepared by the reaction of 2-mercaptoethanol (0.38 g) with sodium hydride (60% dispersion in mineral oil, 0.17 g) in DMA (5 ml)] was stirred at ambient temperature for 2 hours. The mixture was evaporated and the residue was purified by reverse phase column chromatography using an 11:9:0.04 mixture of methanol, water and trifluoroacetic acid as eluent. There was thus obtained 6-(2-hydroxyethylthiomethyl)-4-(3'-methylanilino)quinazoline (0.38 g), m.p. 93°–94° C.

NMR Spectrum: (CD$_3$SOCD$_3$) 2.37 (s, 3H), 2.52 (m, 2H), 3.56 (m, 2H), 3.98 (s, 2H), 7.1–8.1 (m, 6H), 8.60 (d, 1H), 8.84 (s, 1a);

Elemental Analysis: Found C, 54.1; H, 4.5; N, C$_{18}$H$_{19}$N$_3$OS. 1.1CF$_3$CO$_2$H requires C, 53.8; H, 4.5; N, 9.3Z.

EXAMPLE 31

A mixture of 7-methoxycarbonyl-4-(3'-methylanilino)quinazoline (1.3 g) and 2N aqueous sodium hydroxide solution (10 ml) was stirred and heated to 40° C. for 4 hours. The mixture was cooled to ambient temperature and acidified to pH$_6$ by the addition of glacial acetic acid. The precipitate was isolated, washed with water and dried. There was thus obtained 7-carboxy-4-(3'-methylanilino)quinazoline (1.16 g), m.p. >280° C.

NHR Spectrum: (CD$_3$SOCD$_3$) 2.36 (s, 3H), 6.98 (d, 1H), 7.29 (t, 1H), 7.66 (m, 2H), 8.18 (m, 1H), 8.28 (d, 1H), 8.64 (s, 1H), 8.66 (d, 1H), 9.88 (s, 1H);

Elemental Analysis: Found C, 67.3; H, 4.8; N, 14.8; C$_{16}$H$_{13}$N$_3$O$_2$. 0.3H$_2$O requires C, 67.3; H, 4.8; N, 14.7%.

EXAMPLE 32

Ethyl chloroformate (0.146 g) and triethylamine (0.162 g) were added in turn to a stirred mixture of 7-carboxy-4-(3'-methylanilino)quinazoline (0.3 g) and THF (5 ml). The mixture was stirred at ambient temperature for 1 hour. Sodium borohydride (0.123 g) was added and the mixture was stirred at ambient temperature for 2 hours. The mixture was acidified by the addition of 2N aqueous hydrochloric acid and evaporated. The residue was dissolved in water and extracted with methylene chloride. The aqueous phase was basified to pH$_9$ by the addition of a saturated aqueous ammonium hydroxide solution and extracted with ethyl acetate. The organic phase was dried (MgSO$_4$) and evaporated. The residue was purified by column chromatography using increasingly polar mixtures of methylene chloride and methanol as eluent. There was thus obtained 7-hydroxymethyl-4-( 3'-methylanilino)quinazoline (0.125 g), m.p. 175°–177° C.

NHR Spectrum: (CD$_3$SOCD$_3$) 2.35 (s, 3H), 4.70 (d, 2H), 5.45 (t, 1H), 6.96 (d, 1H), 7.2–7.7 (m, 5H), 8.50 (s, 1H), 8.57 (s, 1H), 9.64 (s, 1H);

Elemental Analysis: Found C, 72.2; H, 5.8; N, 15.8; C$_{16}$H$_{15}$N$_3$O requires C, 72.4; H, 5.7; N, 15.8Z.

EXAMPLE 33

Using an analogous procedure to that described in Example 11, 6-amino-4-(3'-trifluoromethylanilino)quinazoline was reacted with acetic anhydride to give 6-acetamido-4-(3'-trifluoromethylanilino)quinazoline in 87% yield as a solid.

NMR Spectrum: (CDSOCD₃) 2.14 (s, 3H), 7.45 (d, 1H), 7.64 (t, 1H}, 7.78 (d, 1H}, 7.87 (m, 1H), 8.18 (d, 1H), 8.26 (s, 1H), 8.60 (s, 1H), 8.73 (d, 1H);

Elemental Analysis: Found C, 58.7; H, 3.9; N, 16.1; $C_{17}H_{13}F_3N_4O$ requires C, 59.0; H, 3.8; N, 16.5%.

EXAMPLE 34

Using an analogous procedure to that described in Example 1, the appropriate substituted 4-chloroquinazoline was reacted with the appropriate aniline to give, as hydrochloride salts, the compounds described in the following table, the structures of which were confirmed by proton magnetic resonance spectroscopy and by elemental analysis.

TABLE III

| Example 34 Compd. No. | $(R^1)_m$ | $(R^2)_n$ | m.p. (°C.) |
|---|---|---|---|
| 1ª | 6-methoxy | 3'-methyl | 236–240 |
| 2ᵇ | 6-methoxy | 3'-chloro | 261–265 |
| 3ᶜ | 6-hydroxy | 3'-methyl | 150–156 |
| 4ᵈ | 6-trifluoromethyl | 3'-methyl | >300 |
| 5ᵉ | 6,7-dimethoxy | 3'-chloro-4'-fluoro | >240 |
| 6ᶠ | 6,7-dimethoxy | 3'-chloro-4'-cyano | >240 |
| 7ᵍ | 6,7-dimethoxy | 3',4'-dichloro | >240 |
| 8ʰ | 6,7-dimethoxy | 3'-nitro | >240 |
| 9ⁱ | 6,7-dimethoxy | hydrogen | 234–236 |
| 10ʲ | 6,7-dimethoxy | 4'-chloro-3'-nitro | >240 |
| 11ᵏ | 6,7-dimethoxy | 4'-fluoro-3'-nitro | >240 |

Notes a. The product gave the following analytical data: Found C, 63.1; H, 5.2; N, 13.5; $C_{16}H_{15}N_3O$. 1.1HCl requires C, 62.9; H, 5.3; N, 13.8%; and the following characteristic NMR data: (CD₃SOCD₃) 2.37 (s, 3H), 4.01 (s, 3H), 7.16 (d, 1H), 7.38 (m, 1H), 7.52 (s, 2H), 7.73 (m, 1H), 7.94 (d, 1H), 8.43 (d, 1H), 8.84 (s, 1H), 11.63 (s, 1H).

The 4-chloro-6-methoxyquinazoline used as a starting material was obtained from 5-methoxyanthranilic acid using analogous procedures to those described in the portion of Example 1 which is concerned with the preparation of starting materials.

The 5-methoxyanthranilic acid used as a starting material was obtained as follows:

A mixture of 5-chloro-2-nitrobenzoic acid (60.5 g) and thionyl chloride (113 ml) was stirred and heated to reflux for 4 hours. The mixture was evaporated. The material so obtained was added to a solution obtained by adding sodium (15.2 g) to methanol (250 ml). The mixture was heated to reflux for 4 hours. The mixture was evaporated and the residue was partitioned between ethyl acetate and water. The organic layer was dried (MgSO₄) and evaporated. The residue was purified by column chromatography using increasingly polar mixtures of methylene chloride and methanol as eluent. There was thus obtained methyl 5-methoxy-2-nitrobenzoate as an oil (22.5 g).

A mixture of the material so obtained, 10% palladium-on-charcoal catalyst (2.1 g), ethanol (200 ml) and ammonium formate (25.2 g) was stirred and heated to 70° C. for 2 hours. The mixture was filtered and the filtrate was evaporated. The residue was partitioned between methylene chloride and a dilute aqueous sodium bicarbonate solution. The organic layer was dried (MgSO₄) and evaporated to give methyl 2-amino-5-methoxybenzoate (15.2 g).

A mixture of the material so obtained, 2N aqueous sodium hydroxide solution (150 ml) and 1,4-dioxan (50 ml) was stirred and heated to 40° C. for 3 hours. The bulk of the 1,4-dioxan was evaporated, the aqueous residue was acidified to pH4 by the addition of concentrated hydrochloric acid and the solution was extracted with ethyl acetate. The organic phase was dried (MgSO₄) and evaporated to give 5-methoxyanthranilic acid (14.1 g).

b. The reaction mixture was heated to reflux for 3 hours. The product gave the following analytical data: Found C, 55.4; H, 4.0; N, 12.8; $C_{15}H_{12}ClN_3O$. 1.1HCl requires C, 55.2; H, 4.0; N, 12.9%; and the following characteristic NMR data: (CD₃SOCD₃) 4.02 (s, 3H), 7.37 (m, 1H), 7.53 (m, 1H), 7.67 (m, 2H), 7.95 (m, 2H), 8.51 (d, 1H), 8.91 (s, 1H), 11.62 (s, 1H).

c. 6-Acetoxy-4-chloroquinazoline was used as the appropriate quinazoline and the reaction mixture was heated to reflux for 2.5 hours. The product gave the following analytical data: Found C, 58.6; H, 5.3; N, 13.4; $C_{15}H_{13}N_3O$. 1HCl. 1H₂O requires C, 58.9; H, 5.2; N, 13.7%; and the following characteristic NMR data: (CD₃SOCD₃) 2.36 (s, 3H), 7.14 (d, 1H), 7.36 (t, 1H), 7.51 (d, 2H), 7.72 (m, 1H), 7.90 (d, 1H), 8.07 (d, 1H), 8.78 (s, 1H), 10.42 (s, 1H), 11.22 (s, 1H).

The 6-acetoxy-4-chloroquinazoline used as a starting material was obtained as follows:

Using an analogous procedure to that described in the portion of Example 1 which is concerned with the preparation of starting materials, 5-hydroxyanthranilic acid was converted into 6-hydroxyquinazolin-4-one. Acetic anhydride (1.38 g) was added dropwise to a mixture of 6-hydroxyquinazolin-4-one (2 g), triethylamine (1.37 g) and DMF (60 ml). The mixture was stirred at ambient temperature for 1 hour. The mixture was evaporated to give 6-acetoxyquinazolin-4-one which was reacted with thionyl chloride using an analogous procedure to that described in the portion of Example 1 which is concerned with the preparation of starting materials.

d. The product gave the following analytical data: Found C, 54.1; H, 3.7; N, 11.7; $C_{16}H_{12}F_3N_3O$. 1HCl requires C, 54.0; H, 3.7; N, 11.8%; and the following characteristic NMR data: (CD₃SOCD₃) 2.37 (s, 3H), 7.17 (s, 1H), 7.38 (t, 1H), 7.51 (d, 2H), 8.07 (m, 2H), 8.91 (m, 2H), 11.45 (s, 1H).

The 4-chloro-6-trifluoromethoxyquinazoline used as a starting material was obtained from 5-trifluoromethoxyanthranilic acid using analogous procedures to those described in the portion of Example 1 which is concerned with the preparation of starting materials.

e. The reaction mixture was heated to reflux for 2 hours. The product gave the following analytical data: Found C, 51.7; H, 3.7; N, 11.1; $C_{16}H_{13}ClFN_3O_2$. 1HCl requires C, 51.9; H, 3.8; N, 11.4%; and the following characteristic NMR data: (CD₃SOCD₃) 4.01 (s, 3H), 4.04 (s, 3H), 7.45 (s, 1H), 7.59 (t, 1H), 7.84 (m, 1H), 8.1 (m, 1H), 8.51 (s, 1H), 8.93 (s, 1H), 11.74 (s, 1H).

f. The reaction mixture was heated to reflux for 2 hours. The product gave the following characteristic NMR data: (CD₃SOCD₃) 4.04 (s, 3H), 4.08 (s, 3H), 7.35 (s, 1H), 7.91 (s, 1H), 8.03 (d, 1H), 8.18 (m, 1H), 8.47 (d, 1H), 8.74 (s, 1H), 9.93 (s, 1H).

g. The reaction mixture was heated to reflux for 2 hours. The product gave the following analytical data: Found C, 49.7; H, 3.7; N, 11.0; $C_{16}H_{13}C_{12}N_3O_2$. 1HCl requires C, 49.7; H, 3.65; N, 10.9%; and the following characteristic NMR data: $(CD_3SOCD_3)$ 4.01 (s, 3H), 4.04 (s, 3H), 7.36 (s, 1H), 7.74 (m, 1H), 7.83 (m, 1H), 8.17 (d, 1H), 8.38 (s, 1H), 8.91 (s, 1H), 11.55 (s, 1H).

h. The reaction mixture was heated to reflux for 2 hours. The product gave the following analytical data: Found C, 53.1; H, 4.2; N, 15.3; $C_{16}H_{14}N_4O_4$ 1HCl requires C, 53.0; H, 4.2; N, 15.4%; and the following characteristic NMR data: $(CD_3SOCD_3)$ 4.0 (s, 3H), 4.04 (s, 3H), 7.37 (s, 1H), 7.75 (t, 1H), 8.11 (m, 1H), 8.33 (m, 1H), 8.40 (s, 1H), 8.74 (m, 1H), 8.88 (s, 1H), 11.58 (s, 1H).

i. The reaction mixture was heated to reflux for 3 hours. The product gave the following analytical data: Found C, 59.1; H, 5.0; N, 12.7; $C_{16}H_{15}N_3O_2$. 1HCl. 0.35$H_2O$ requires C, 59.3; H, 5.2; N, 13.0%; and the following characteristic NMR data: $(CD_3SOCD_3)$ 3.99 (s, 3H), 4.02 (s, 3H), 7.1–7.6 (m, 4H), 7.68–7.75 (m, 2H), 8.43 (s, 1H}, 8.80 (s, 1H).

j. The reaction mixture was heated to reflux for 2 hours. The product gave the following analytical data: Found C, 48.3; H, 3.5; N, 13.5; $C_{16}H_{13}ClN_4O_4$. 1HCl requires C, 48.4; H, 3.5; N, 14.1%; and the following characteristic NMR data: $(CD_3SOCD_3)$ 4.01 (s, 3H), 4.05 (s, 3H), 7.34 (s, 1H), 7.86 (d, 1H), 7.88 (d, 1H), 8.23 (m, 1H), 8.48 (s, 1H), 8.64 (d, 1H), 8.94 (s, 1H), 11.87 (s, 1H).

k. The product gave the following analytical data: Found C, 50.7; H, 3.4; N, 14.2; $C_{16}H_{13}FN_4O_4$.1HCl requires C, 50.5; H, 3.7; N, 14.7%; and the following characteristic NMR data: $(CD_3SOCD_3)$ 4.0 (s, 3H), 4.04 (s, 3H), 7.40 (s, 1H), 7.71 (m, 1H), 8.29 (m, 1H), 8.50 (s, 1H), 8.65 (m, 1H), 8.92 (s, 1H), 11.9 (broad s, 1H).

EXAMPLE 35

3-Methylaniline (0.123 g) was added dropwise to a stirred solution of 6-bromomethyl-4-chloroquinazoline (0.3 g) in DMF (3 ml). The mixture was stirred at ambient temperature for 2 hours. Diethyl ether (10 ml) was added and the precipitate was isolated. There was thus obtained 6-bromomethyl-4-(3'-methylanilino)quinazoline in 32% yield, m.p. >260° C. (decomposes);

NMR Spectrum: $(CD_3SOCD_3)$ 2.37 (s, 3H), 4.98 (s, 2H), 7.17 (d, 1H), 7.39 (t, 1H), 7.53 (m, 2H), 7.95 (d, 1H), 8.15 (m, 1H), 8.93 (s, 1H), 8.96 (d, 1H), 11.59 (broad s, 1H);

Elemental Analysis: Found C, 56.5; H, 4.6; N, 12.3; $C_{16}H_{14}BrN_3$. 0.25HCl requires C, 56.9; H, 4.3; N, 12.4%.

The 6-bromomethyl-4-chloroquinazoline used as a starting material was obtained as described in Note g. below Table II in Example 6.

Example 36

Using an analogous procedure to that described in Example 7, 6,7-dimethoxy-4-(3'-methylanilino)-5-nitroquinazoline was reduced to give 5-amino-6,7-dimethoxy-4-(3'-methylanilino)quinazoline which was purified by column chromatography using increasingly polar mixtures of methylene chloride and ethyl acetate as eluent. There was thus obtained the required product in 55% yield, m.p. 181°–182° C. NMR Spectrum: $(CD_3SOCD_3)$ 2.30 (s, 3H), 3.70 (s, 3H), 3.86 (s, 3H), 6.51 (s, 1H), 6.86 (d, 1H), 7.10 (m, 2H), 7.19 (t, 1H), 7.90 (s, 1H); Elemental Analysis: Found C, 65.4; H, 5.9; N, 17.6; $C_{17}H_{18}N_4O_2$. 0.15$H_2O$ requires C, 65.2; H, 5.8; N, 17.9%.

The 6,7-dimethoxy-4-(3'-methylanilino)-5-nitroquinazoline used as a starting material was obtained as follows:

6,7-Dimethoxyquinazolin-4-one (10 g) was added portionwise to a stirred mixture of concentrated sulphuric acid (30 ml) and fuming nitric acid (30 ml) which had been cooled to 0° C. The mixture was stirred at ambient temperature for 1 hour. The mixture was poured onto a mixture of ice and water (500 ml). The precipitate was isolated, washed with water and dried. There was thus obtained 6,7-dimethoxy-5-nitroquinazolin-4-one (9.51 g).

Using analogous procedures to those described in Example 1, the compound so obtained was converted into 6,7-dimethoxy-4-(3'-methylanilino)-5-nitroquinazoline in 71% yield, m.p. 151°–155° C. NMR Spectrum: $(CD_3SOCD_3)$ 2.30 (s, 3H), 3.86 (s, 3H), 4.02 (s, 3H), 6.75 (m, 2H), 6.88 (d, 1H), 7.22 (t, 1H), 7.28 (s, 1H), 7.85 (s, 1H).

Example 37

Using an analogous procedure to that described in Example 7, except that the reaction mixture was heated to 70° C. for 2 hours, 4-(3'-methylanilino)-7-methylthio-6-nitroquinazoline was reduced to 6-amino-4-(3'-methylanilino)-7-methylthioquinazoline which was purified by column chromatography using increasingly polar mixtures of methylene chloride and ethyl acetate as eluent. There was thus obtained the required product in 22% yield, m.p. 217°–218° C. NMR Spectrum: $(CD_3SOCD_3)$ 2.33 (s, 3H), 2.59 (s, 3H), 5.34 (broad s, 2H), 6.90 (d, 1H), 7.24 (t, 1H), 7.44 (s, 1H), 7.50 (s, 1H), 7.63 (s, 2H), 8.47 (s, 1H); Elemental Analysis: Found C, 64.8; H, 5.4; N, 18.7; $C_{16}H_{16}N_4S$ requires C, 64.8; H, 5.4; N, 18.9%.

The 4-(3'-methylanilino)-7-methylthio-6-nitroquinazoline used as a starting material was obtained as follows:

A mixture of 4-chloroanthranilic acid (17.2 g) and formamide (10 ml) was stirred and heated to 130° C. for 45 minutes and to 175° C. for 75 minutes. The mixture was allowed to cool to approximately 100° C. and 2-(2-ethoxyethoxy)ethanol (50 ml) was added. The solution so formed was poured into a mixture (250 ml) of ice and water. The precipitate was isolated, washed with water and dried. There was thus obtained 7-chloroquinazolin-4-one (15.3 g, 85%).

After repetition of this reaction, 7-chloroquinazolin-4-one (30 g) was added portionwise to a stirred mixture of concentrated sulphuric acid (60 ml) and fuming nitric acid (60 ml) which had been cooled to 0° C. The mixture was stirred at ambient temperature for 1 hour and then heated to 110° C. for 30 minutes. The mixture was cooled to ambient temperature and poured onto a mixture of ice and water (1L). The precipitate was isolated, washed with water and dried. There was thus obtained 7-chloro-6-nitroquinazolin-4-one (38.1 g).

Using analogous procedures to those described in Example 1, the material so obtained was converted into 7-chloro-4-(3'-methylanilino)-6-nitroquinazoline in 59% yield, m.p. 271°–274° C.

A portion (0.9 g) of the material so obtained was dissolved in DMA (15 ml). Sodium methanethiolate (0.44 g) was added and the mixture was stirred at ambient temperature for 1 hour. Them mixture was acidified by the addition of glacial acetic acid. The mixture was evaporated and the residue was triturated under methylene chloride. The solid so obtained was partitioned between methylene chloride and a dilute aqueous ammonium hydroxide solution. The organic layer was dried (MgSO$_4$) and evaporated to give 4-(3'-methylanilino)-7-methyl-thio-6-nitroquinazoline (0.473 g), m.p. 230°–231° C. NMR Spectrum: $(CD_3SOCD_3)$ 2.33 (s, 3H), 2.63 (s, 3H), 6.97 (d, 1H), 7.28 (t, 1H), 7.61 (s, 1H), 7.63 (m, 2H), 8.63 (s, 1H), 9.70 (s, 1H); Elemental Analysis: Found C, 58.6; H, 4.6; N, 17.2; $C_{16}H_{14}N_4O_2S$ requires C, 58.8; H, 4.3; N, 17.1%.

Example 38

A mixture of 7-methoxy-4-(3'-methylanilino)-6-nitroquinazoline (0.4 g), 10% palladium-on-charcoal catalyst (0.06 g), DMF (5 ml) and ethanol (20 ml) was stirred under an atmosphere pressure of hydrogen for 5 hours. The mixture was filtered and the filtrate was evaporated. The residue was purified by column chromatography on reversed-phase silica using decreasingly polar mixtures of methanol, water and trifluoroacetic acid as eluent. There were thus obtained in turn: 6-hydroxyamino-7-methoxy-4-(3'-methylanilino)quinazoline (0.038 g), m.p. 130°–147° C. NMR Spectrum: $(CD_3SOCD_3)$ 2.35 (s, 3H), 4.02 (s, 3H), 7.12 (d, 1H), 7.19 (s, 1H), 7.34 (t, 1H), 7.48 (m, 2H), 8.10 (s, 1H), 8.70 (s, 1H); Elemental Analysis: Found C, 44.0; H, 3.5; N, 10.5; $C_{16}H_{16}N_4O_2$. $1H_2O$. $2CF_3CO_2H$ requires C, 44.3; H, 3.7; N, 10.7%; and 6-amino-7-methoxy-4-(3'-methylanilino)quinazoline (0.049 g), m.p. 85°–95° C. NMR Spectrum: $(CD_3SOCD_3)$ 2.36 (s, 3H), 4.03 (s, 3H), 7.12 (d, 1H), 7.18 (s, 1H), 7.35 (t, 1H), 7.45 (m, 2H), 7.62 (s, 1H), 8.69 (s, 1H); Elemental Analysis: Found C, 52.3; H, 4.0; N, 13.0; $C_{16}H_{16}N_4O$. $1.3CF_3CO_2H$ requires C, 52.1; H, 4.0; N, 13.1%.

The 7-methoxy-4-(3'-methylanilino)-6-nitroquinazoline used as a starting material was obtained as follows:

7-Chloro-4-(3'-methylanilino)-6-nitroquinazoline (0.35 g) was added portionwise to a methanolic solution of sodium methoxide [prepared by the addition of sodium (0.055 g) to methanol (5 ml)]. The mixture was stirred and heated to reflux for 1 hour. A second portion of sodium (0.069 g) was added and the mixture was heated to reflux for 5 hours. The mixture was evaporated and the residue was purified by column chromatography on reversed-phase silica using initially a 50:50:0.2 mixture of water, methanol and trifluoroacetic acid and then decreasingly polar mixtures of water, methanol and trifluoroacetic acid as eluent. There was thus obtained 7-methoxy-4-(3'-methylanilino)-6-nitroquinazoline (0.81 g), m.p. 149°–154° C. Example 39

1,2-Dibromoethane (10.9 g) was added to a stirred mixture of 7-hydroxy-6-methoxy-4-(3'-methylanilino)quinazoline (2.5 g), potassium carbonate (3.69 g) and DMF (60 ml). The mixture was stirred at ambient temperature for 30 minutes and then heated to 80° C. for 2 hours. The mixture was evaporated and the residue was partitioned between methylene chloride and water. The organic phase was dried $(MgSO_4)$ and evaporated. The residue was purified by column chromatography using increasingly polar mixtures of methylene chloride and methanol as eluent. There was thus obtained 7-(2-bromoethoxy)- 6-methoxy-4-(3'-methylanilino)quinazoline (2.8 g), m.p. 86°–89° C. NMR Spectrum: $(CD_3SOCD_3)$ 2.35 (s, 3H), 3.89 (t, 2H), 3.99 (s, 3H), 4.51 (t, 2H), 7.21 (s, 1H), 7.28 (t, 1H), 7.58 (s, 1H), 7.62 (d, 1H), 7.88 (s, 1H), 8.46 (s, 1H), 8.94 (d, 1H), 9.46 (s, 1H); Elemental Analysis: Found C, 55.7; H, 5.9; N, 11.9; $C_{18}H_{18}Br N_3O_2$. 0.9DMF requires C, 55.5; H, 5.6; N, 11.7%.

Example 40

A mixture of 7-(2-bromoethoxy)-6-methoxy-4-(3'-methylanilino)quinazoline (0.25 g) and aniline (4 ml) was stirred at ambient temperature for 16 hours. The mixture was evaporated and the residue was purified by column chromatography using increasingly polar mixtures of methylene chloride and ethyl acetate as eluent. There was thus obtained 7-(2-anilinoethoxy)-6-methoxy-4-(3'-methylanilino)quinazoline (0.169 g), m.p. 160°–162° C. NMR Spectrum: $(CD_3SOCD_3)$ 2.35 (s, 3H), 3.51 (m, 2H), 3.97 (s, 3H), 4.30 (t, 2H), 6.58 (t, 1H), 6.66 (d, 2H), 6.94 (d, 1H), 7.12 (t, 2H), 7.20 (s, 1H), 7.28 (t, 1H), 7.58 (s, 1H), 7.63 (d, 1H), 7.87 (s, 1H), 8.48 (s, 1H), 9.50 (s, 1H); Elemental Analysis: Found C, 69.6; H, 6.2; N, 13.6; $C_{24}H_{24}N_4O_2$. $0.75H_2O$ requires C, 69.6; H, 6.2; N, 13.5%.

Example 41

A mixture of 7-(2-bromoethoxy)-6-methoxy-4-(3'-methylanilino)quinazoline (0.25 g) and morpholine (4 ml) was stirred at ambient temperature for 4 hours. The mixture was evaporated and the residue was partitioned between methylene chloride and a dilute aqueous sodium bicarbonate solution. The organic phase was dried $(MgSO_4)$ and evaporated. The residue was triturated under diethyl ether to give 6-methoxy-4-(3'-methylanilino)-7-(2-morpholinoethoxy)quinazoline (0.198 g), m.p. 168°–170° C. NMR Spectrum: $(CD_3SOCD_3+CD_3CO_2D)$ 2.35 (s, 3H), 3.15 (t, 4H), 3.81 (t, 4H), 3.96 (s, 3H), 6.93 (d, 1H), 7.21 (s, 1H), 7.26 (t, 1H), 7.58 (s, 1H), 7.63 (d, 1H), 7.84 (s, 1H), 8.44 (s, 1H), 9.58 (s, 1H); Elemental Analysis: Found C, 64.3; H, 6.9; N, 13.8; $C_{22}H_{26}N_4O_3$. $0.9H_2O$ requires C, 64.3; H, 6.8; N, 13.6%.

Example 42

2-Methoxyacetyl chloride (0.085 g) was added to a stirred solution of 7-hydroxy-6-methoxy-4-(3'-methylanilino)quinazoline (0.2 g) in DMA (1 ml) and the mixture was stirred at ambient temperature for 16 hours. A second portion of 2-methoxyacetyl chloride (0.085 g) was added and the mixture was heated to 45° C. for 3 hours. The mixture was cooled to ambient temperature and ethyl acetate (5 ml) was added. The precipitate was isolated, washed with ethyl acetate and with diethyl ether and dried under vacuum. There was thus obtained 6-methoxy-7-(2-methoxyacetoxy)-4-(3'-methylanilino)quinazoline (0.218 g), m.p. 215°–219° C. NMR Spectrum: $(CD_3SOCD_3)$ 2.37 (s, 3H), 3.43 (s, 3H), 4.06 (s, 3H), 4.45 (s, 2H), 7.16 (d, 1H), 7.33 (s, 1H), 7.38 (t, 1H), 7.52 (m, 2H), 8.83 (s, 1H), 8.62 (s, 1H); Elemental Analysis: Found C, 53.5; H, 5.8; N, 10.0; $C_{19}H_{19}N_3O_4$. 1HCl. $2H_2O$ requires C, 53.5; H, 5.6; N, 9.9%.

Example 43

A mixture of 6-amino-4-(3'-methylanilino)quinazoline (0.25 g), benzoyl chloride (0.148 g), triethylamine (2 ml) and DMF (2 ml) was stirred and heated to 100° C. for 3 hours. A further portion of benzoyl chloride (0.296 g) was added and the mixture was heated to 100° C. for a further 3 hours. The mixture was cooled to ambient temperature and partitioned between methylene chloride and water. The organic phase was dried $(MgSO_4)$ and evaporated. The residue was purified by column chromatography using increasingly polar mixtures of methylene chloride and ethyl acetate as eluent. There was thus obtained 6-benzamido-4-(3'-methylanilino)quinazoline (0.142 g), m.p. 243°–245° C. NMR Spectrum: $(CD_3SOCD_3)$ 2.34 (s, 3H), 6.95 (d, 1H), 7.27 (m, 1H), 7.6 (m, 5H), 7.79 (d, 1H), 8.01 (m, 1H), 8.04 (m, 2H), 8.52 (s, 1H), 8.90 (d, 1H), 9.80 (s, 1H), 10.55 (s, 1H); Elemental Analysis: Found C, 73.2; H, 5.0; N, 15.4; $C_{22}H_{18}N_4O$. $0.25H_2O$ requires C, 73.6; H, 5.2; N, 15.6%.

Example 44

A mixture of 6-amino-4-(3'-methylanilino)quinazoline (0.75 g), methyl 3-chloroformylpropionate (0.451 g), triethylamine (0.303 g) and toluene (6 ml) was stirred and heated to reflux for 4 hours. The mixture was evaporated and the residue was purified by column chromatography using increasingly polar mixtures of methylene chloride and methanol as eluent. There was thus obtained 6-(3-methoxycarbonylpropionamido)-4-(3'-methylanilino)quinazoline (0.46 g), m.p. 202°–203° C. NMR Spectrum: ($CD_3SOCD_3$) 2.34 (s, 3H), 2.68 (m, 4H), 3.61 (s, 3H), 6.95 (d, 1H), 7.26 (t, 1H), 7.6 (s, 2H), 7.74 (d, 1H), 7.84 (m, 1H), 8.52 (s, 1H), 8.70 (d, 1H), 9.8 (s, 1H), 10.3 (s, 1H); Elemental Analysis: Found C, 65.3; H, 5.5; N, 14.8; $C_{20}H_{20}N_4O_3$ requires C, 65.2; H, 5.5; N, 15.0%.

Example 45

A mixture of 6-amino-4-(3'-methylanilino)quinazoline (0.5 g), methyl 4-chlorobutyrate (1 ml) and triethylamine (0.55 ml) was stirred and heated to 100° C. for 4 hours. The mixture was cooled to ambient temperature and partitioned between methylene chloride and water. The organic layer was dried ($MgSO_4$) and evaporated. The residue was purified by column chromatography using a 20:1 mixture of methylene chloride and methanol as eluent. There was thus obtained 6-(3-methoxycarbonylpropylamino)-4-(3'-methylanilino)quinazoline (0.32 g). NMR Spectrum: ($CD_3SOCD_3$) 1.92 (m, 2H), 2.34 (s, 3H), 3.23 (m, 4H), 3.61 (s, 3H), 6.22 (t, 1H), 6.93 (d, 1H), 7.18 (d, 1H), 7.25 (m, 1H), 7.29 (t, 1H), 7.6 (s, 1H), 7.65 (d, 1H), 8.43 (s, 1H), 9.25 (s, 1H).

A mixture of the material so obtained and diphenyl ether (0.5 ml) was stirred and heated to 160° C. for 3 hours. The mixture was cooled to ambient temperature and partitioned between methylene chloride and water. The organic phase was dried ($MgSO_4$) and evaporated. The residue was purified by column chromatography using a 20:1 mixture of methylene chloride and methanol as eluent. There was thus obtained 4-(3'-methylanilino)-6-(2-oxopyrrolidin-1-yl)quinazoline (0.053 g), m.p. 212°–215° C. NMR Spectrum: ($CD_3SOCD_3$) 2.15 (m, 2H), 2.35 (s, 3H), 2.59 (t, 2H), 4.01 (t, 2H), 7.02 (d, 1H), 7.30 (t, 1H), 7.6 (m, 2H), 7.8 (d, 1H), 8.24 (d, 1H), 8.55 (s, 1H), 8.60 (m, 1H), 9.88 (s, 1H); Elemental Analysis: Found C, 64.8; H, 5.0; N, 14.9; $C_{19}H_{18}N_4O$. $0.75CH_2Cl_2$. $0.5H_2O$ requires C, 64.4; H, 5.4; N, 14.6%.

Example 46

Phenyl isocyanate (0.193 g) was added to a stirred mixture of 6-amino-4-(3'-methylanilino)quinazoline (0.39 g) and THF (15 ml) which had been cooled to −2° C. The mixture was stirred at 5° C. for 10 minutes and then allowed to warm to ambient temperature. The mixture was evaporated and the residue was purified by column chromatography using a 20:1 mixture of methylene chloride and methanol as eluent. There was thus obtained 4-(3'-methylanilino)-6-(3-phenylureido)quinazoline (0.335 g), m.p. 224°–226° C. NMR Spectrum: ($CD_3SOCD_3$) 2.34 (s, 3H), 6.94 (d, 1H), 7.01 (m, 1H), 7.28 (m, 2H), 7.30 (t, 1H), 7.51 (m, 2H), 7.62 (m, 2H), 7.73 (d, 1H), 7.92 (m, 1H), 8.46 (d, 1H), 8.49 (s, 1H), 8.90 (s, 1H), 8.94 (s, 1H), 9.75 (s, 1H); Elemental Analysis: Found C, 65.2; H, 5.5; N, 17.2; $C_{22}H_{19}N_5O$. $2H_2O$ requires C, 65.2; H, 5.7; N, 17.3%.

Example 47

A solution of sodium cyanate (0.195 g) in water (3 ml) was added to a stirred solution of 6-amino-4-(3'-methylanilino)quinazoline (0.25 g) in water (5 ml) and acetic acid (0.1 ml). The mixture was stirred at ambient temperature for 2 hours. The mixture was evaporated and the residue was purified by column chromatography on reversed-phase silica using initially a 30:70:0.2 mixture and then a 45:55:0.2 mixture of methanol, water and trifluoroacetic acid as eluent. There was thus obtained 4-(3'-methylanilino)-6-ureidoquinazoline (0.047 g), m.p. >230° C. (decomposes). NMR Spectrum: ($CD_3SOCD_3$) 2.36 (s, 3H), 6.18 (s, 2H), 7.12 (d, 1H), 7.36 (m, 1H), 7.48 (m, 2H), 7.79 (d, 1H), 8.01 (m, 1H), 8.65 (d, 1H), 8.75 (s, 1H), 9.11 (s, 1H), 11.12 (s, 1H); Elemental Analysis: Found C, 48.8; H, 4.1; N, 15.4; $C_{16}H_{15}N_5O$. $1H_2O$. $1.3CF_3CO_2H$ requires C, 48.6; H, 4.0; N, 15.2%.

Example 48

Benzyl chloride (0.378 g) was added to a stirred mixture of 7-hydroxy-6-methoxy-4-(3'-methylanilino)quinazoline (0.281 g), potassium carbonate (0.414 g) and DMA (4 ml). The mixture was stirred at ambient temperature for 10 minutes and then heated to 60° C. for 1 hour. The mixture was evaporated and the residue was purified by column chromatography using initially methylene chloride and then a 100:3 mixture of methylene chloride and methanol as eluent. There was thus obtained 7-benzyloxy-6-methoxy-4-(3'-methylanilino)quinazoline (0.225 g), m.p. 203°–205° C. NMR Spectrum: ($CD_3SOCD_3$) 2.34 (s, 3H), 3.97 (s, 3H), 5.28 (s, 2H), 6.93 (d, 1H), 7.27 (t, 1H), 7.28 (s, 1H), 7.22-7.55 (m, 5H), 7.58 (s, 1H), 7.63 (d, 1H), 7.87 (s, 1H), 8.44 (s, 1H), 9.41 (s, 1H); Elemental Analysis: Found C, 74.0; H, 5.8; N, 11.1; $C_{23}H_{21}N_3O_2$ requires C, 74.4; H, 5.7; N, 11.3%.

Example 49

Isopropyl bromide (0.246 g) was added to a stirred mixture of 7-hydroxy-6-methoxy-4-(3'-methylanilino)quinazoline (0.281 g), potassium carbonate (0.414 g) and DMA (3 ml). The mixture was stirred at ambient temperature for 30 minutes and then heated to 70° C. for 1 hour. The mixture was partitioned between ethyl acetate and water. The organic phase was dried ($MgSO_4$) and evaporated to give 7-isopropoxy-6-methoxy-4-(3'-methylanilino)quinazoline (0.28 g), m.p. 218°–221° C. NMR Spectrum: ($CD_3SOCD_3$) 1.36 (d, 6H), 2.34 (s, 3H), 3.94 (s, 3H), 4.83 (m, 1H), 6.94 (d, 1H), 7.17 (s, 1H), 7.27 (t, 1H), 7.57 (s, 1H), 7.64 (d, 1H), 7.82 (s, 1H), 8.43 (s, 1H); Elemental Analysis: Found C, 69.4; H, 6.7; N, 12.0; $C_{19}H_{21}N_3O_2$. $0.3H_2O$. $0.1EtOAc$ requires C, 69.0; H, 6.6; N, 12.4%.

Example 50

Ethyl iodide (0.624 g) was added to a stirred mixture of 6,7-dihydroxy-4-(3'-methylanilino)quinazoline (0.534 g), potassium carbonate (0.828 g) and DMA (10 ml). The mixture was heated to 50° C. for 2 hours. A second portion of ethyl iodide (0.624 g) was added and the mixture was heated to 60° C. for 2 hours. The mixture was evaporated and the residue was purified by column chromatography using initially methylene chloride and then increasingly polar mixtures of methylene chloride and methanol as eluent. There was thus obtained 6,7-diethoxy-4-(3'-methylanilino)quinazoline (0.26 g), m.p. 178°–180° C. NMR Spectrum: ($CD_3SOCD_3$) 1.43 & 1.44 (2 t's, 6H), 2.34 (s, 3H), 4.2 (m, 4H), 6.92 (d, 1H), 7.14 (s, 1H), 7.26 (t, 1H), 7.57 (s, 1H), 7.63 (d, 1H), 7.82 (s, 1H), 8.42 (s, 1H); Elemental Analysis: Found C, 69.1; H, 6.6; N, 12.2; $C_{19}H_{21}N_3O_2$. $0.48H_2O$ requires C, 68.7; H, 6.6; N, 12.6%.

Example 51

2-Bromoethyl methyl ether (0.834 g) was added to a stirred mixture of 6,7-dihydroxy-4-(3'-methylanilino)quinazoline (0.534 g), potassium carbonate (0.828 g) and DMA (10 ml). The mixture was stirred at ambient temperature for 16 hours. The mixture was evaporated and the residue was partitioned between ethyl acetate and water. The organic layer was dried ($MgSO_4$) and evaporated. The residue was purified by column chromatography using increasingly polar mixtures of methylene chloride and methanol as eluent. The gum so obtained was dissolved in ethyl acetate (4 ml) and acidified by the addition of a saturated solution of hydrogen chloride in diethyl ether. The precipitate was isolated. There was thus obtained 6,7-di-(2-methoxyethoxy)-4-(3'-methylanilino)quinazoline hydrochloride (0.292 g), m.p. 218°–220° C. NMR Spectrum: ($CD_3SOCD_3$) 2.34 (s, 3H), 3.36 (s, 6H), 3.75–3.8 (m, 4H), 4.1–4.5 (m, 4H), 7.14 (d, 1H), 7.37 (t, 1H), 7.40 (s, 1H), 7.48 (m, 2H), 8.35 (s, 1H), 8.79 (s, 1H); Elemental Analysis: Found C, 59.8; H, 6.4; N, 9.9; $C_{21}H_{25}N_3O_4$. 1HCl requires C, 60.0; H, 6.2; N, 10.0%.

Example 52

1,2-Dibromoethane (0,376 g) was added to a stirred mixture of 6,7-dihydroxy-4-(3'-methylanilino)quinazoline (0.534 g), potassium carbonate (0.828 g) and DMA (20 ml). The mixture was heated to 100° C. for 30 minutes. The mixture was evaporated and the residue was purified by column chromatography using increasingly polar mixtures of methylene chloride and ethyl acetate as eluent. There was thus obtained 6,7-ethylenedioxy-4-(3'-methylanilino)quinazoline (0.23 g), m.p. 223°–226° C. NMR Spectrum: ($CD_3SOCD_3$) 2.34 (s, 3H), 4.40 (s, 4H), 7.14 (d, 1H), 7.17 (s, 1H), 7.26 (t, 1H), 7.66 (m, 2H), 8.10 (s, 1H), 8.43 (s, 1H), 9.38 (s, 1H); Elemental Analysis: Found C, 67.5; H, 5.1; N, 13.0; $C_{17}H_{15}N_3O_2$. $0.33H_2O$. 0.25EtOAc requires C, 67.2; H, 5.5; N, 13.1%.

Example 53

A mixture of 6-bromomethyl-4-(3'-methylanilino)quinazoline (0.415 g) and morpholine (2 ml) was stirred and heated to 60° C. for 2 hours. The mixture was cooled to ambient temperature and the precipitate was isolated. The solid so obtained was partitioned between methylene chloride and water. The organic phase was washed with brine, dried ($MgSO_4$) and evaporated. There was thus obtained 6-morpholinomethyl-4-(3'-methylanilino)quinazoline (0.195 g), m.p. 191°–193° C. NMR Spectrum: ($CD_3SOCD_3$) 2.34 (s, 3H), 2.49 (t, 4H), 3.62 (t, 4H), 3.69 (s, 2H), 6.96 (d, 1H), 7.29 (t, 1H), 7.69 (m, 2H), 7.74 (d, 1H), 7.85 (m, 1H), 8.45 (s, 1H), 8.55 (s, 1H), 9.71 (s, 1H); Elemental Analysis: Found C, 71.2; H, 6.8; N, 16.2; $C_{20}H_{22}N_4O$ requires C, 71.2; H, 6.6; N, 16.6%.

Example 54

A mixture of 6-bromomethyl-4-(3'-methylanilino)quinazoline (0.3 g), aniline (0.085 g) and DMA (5 ml) was stirred and heated to 80° C. for 2 hours. The mixture was evaporated and the residue was purified by column chromatography using increasingly polar mixtures of methylene chloride and methanol as eluent. There was thus obtained 6-anilinomethyl-4-(3'-methylanilino)quinazoline as an oil (0.254 g), which was dissolved in ethyl acetate. A saturated solution of hydrogen chloride in diethyl ether was added and the precipitate so formed was isolated. There was thus obtained 6-anilinomethyl-4-(3'-methylanilino)quinazoline dihydrochloride, m.p. 216°–221° C. NMR Spectrum: ($CD_3SOCD_3$) 2.30 (s, 3H), 4.45 (s, 2H), 6.6 (t, 1H), 6.7 (d, 2H), 7.05 (d, 1H), 7.08 (d, 1H), 7.10 (d, 1H), 7.31 (m, 1H), 7.5 (m, 2H), 7.88 (d, 1H), 8.06 (m, 1H), 8.83 (s, 1H), 9.02 (s, 1H); Elemental Analysis: Found C, 60.4; H, 5.8; N, 12.9; $C_{22}H_{20}N_4$. 2HCl. $1.33H_2O$ requires C, 60.4; H, 5.6; N, 12.8%.

Example 55

Sodium methoxide (0.073 g) was added to a stirred mixture of 6-bromomethyl-4-(3'-methylanilino)quinazoline (0.3 g) and methanol (5 ml). The mixture was stirred at ambient temperature for 2 hours. The mixture was evaporated and the residue was purified by column chromatography using increasingly polar mixtures of methylene chloride and ethyl acetate as eluent. There was thus obtained 6-methoxymethyl-4-(3'-methylanilino)quinazoline as a gum (0.045 g). NMR Spectrum: ($CD_3SOCD_3$) 2.36 (s, 3H), 3.39 (s, 3H), 4.62 (s, 2H), 7.07 (d, 1H), 7.35 (t, 1H), 7.58 (s, 2H), 7.82 (d, 1H), 7.92 (d, 1H), 8.65 (s, 1H), 8.76 (s, 1H).

Example 56

A mixture of 6-bromomethyl-4-(3'-methylanilino)quinazoline (0.5 g) and 2-methoxyethanol (2.5 ml) was stirred and heated to 80° C. for 2 hours. The mixture was cooled to ambient temperature and partitioned between methylene chloride and water. The organic phase was washed with brine, dried ($MgSO_4$) and evaporated. The residue was purified by column chromatography using increasingly polar mixtures of methylene chloride and ethyl acetate as eluent. There was thus obtained 6-(2-methoxyethoxymethyl)-4-(3'-methylanilino)quinazoline as an oil (0.211 g). NMR Spectrum: ($CD_3SOCD_3$) 2.34 (s, 3H), 3.27 (s, 3H), 3.53 (m, 2H), 3.63 (m, 2H), 4.67 (s, 2H), 6.96 (d, 1H), 7.28 (t, 1H), 7.7 (m, 2H), 7.8 (m, 2H), 8.5 (s, 1H), 8.57 (s, 1H), 9.8 (s, 1H); Elemental Analysis: Found C, 68.5; H, 6.8; N, 12.5; $C_{19}H_{21}N_3O_2$ requires C, 68.6; H, 6.7; N, 12.6%.

Example 57

Sodium methanethiolate (0.141 g) was added to a stirred mixture of 6-bromomethyl-4-(3'-methylanilino)quinazoline (0.6 g), triethylamine (0.203 g) and DMF (2 ml). The mixture was stirred at ambient temperature for 4 hours. The mixture was evaporated and the residue was purified by column chromatography using increasingly polar mixtures of methylene chloride and ethyl acetate as eluent. There was thus obtained an oil which was triturated under a mixture of hexane and diethyl ether to give 4-(3'-methylanilino)-6-methylthiomethylquinazoline (0.205 g), m.p. 134°–136° C. NMR Spectrum: ($CD_3SOCD_3$) 2.01 (s, 3H), 2.34 (s, 3H), 3.88 (s, 2H), 6.97 (d, 1H), 7.28 (t, 1H), 7.6 (m, 2H), 7.75 (d, 1H), 7.83 (m, 1H), 8.45 (d, 1H), 8.58 (s, 1H), 9.8 (broad s, 1H); Elemental Analysis: Found C, 69.7; H, 5.8; N, 14.21 $C_{17}H_{17}N_3S$. $0.1C_6H_{14}$ requires C, 69.5; H, 6.1; N, 13.8%.

Example 58

Triethylamine (0.1 ml) was added to a stirred mixture of 6-bromomethyl-4-(3'-methylanilino)quinazoline (0.33 g), benzenethiol (0.11 g) and DMA (2 ml). The mixture was stirred at ambient temperature for 5 hours. The mixture was evaporated and the residue was purified by column chromatography using increasingly polar mixtures by methylene chloride and ethyl acetate as eluent. There was thus obtained 4-(3'-methylanilino)-6-phenylthiomethylquinazoline (0.155 g), m.p. 145°–148° C. NMR Spectrum: (CD$_3$SOCD$_3$) 2.34 (s, 3H), 4.41 (s, 2H), 6.96 (d, 1H), 7.24 (t, 1H), 7.3 (s, 5H), 7.65 (m, 2H), 7.72 (d, 1H), 7.86 (m, 1H), 8.54 (d, 1H), 8.55 (s, 1H), 9.73 (s, 1H); Elemental Analysis: Found C, 73.7; H, 5.3; N, 11.5; C$_{22}$H$_{19}$N$_3$S requires C, 73.9; H, 5.4; N, 11.8%.

Example 59

Succinyl dichloride (0.207 g) was added to a mixture of 6-amino-4-(3'-methylanilino)quinazoline (0.32 g), triethylamine (0.128 g) and toluene (5 ml). The mixture was stirred and heated to reflux for 2 hours. The mixture was evaporated and the residue was purified by column chromatography using increasingly polar mixtures of methylene chloride and methanol as eluent. There was thus obtained 4-(3'-methylanilino)-6-(2,5-dioxopyrrolidin-1-yl)quinazoline (0.082 g), m.p. >150° C. NMR Spectrum: (CD$_3$SOCD$_3$) 2.34 (s, 3H), 2.90 (s, 4H), 6.98 (d, 1H), 7.28 (t, 1H), 7.61 (d, 2H), 7.75 (m, 1H), 7.88 (d, 1H), 8.50 (d, 1H), 8.64 (s, 1H), 9.95 (s, 1H); Elemental Analysis: Found C, 64.9; H, 5.2; N, 15.2; C$_{19}$H$_{16}$N$_4$O$_2$. 0.4HCl. 0.4CH$_3$OH requires C, 64.8; H, 5.0; N, 15.6%.

Example 60

3-Chloroacetyl chloride (0.473 g) was added to a mixture of 6-amino-4-(3'-methylanilino)quinazoline (1 g), triethylamine (0.423 g) and DMF (5 ml). The mixture was stirred and heated to 50° C. for 2 hours. The mixture was evaporated and the residue was purified by column chromatography using increasingly polar mixtures of methylene chloride and methanol as eluent. There was thus obtained 6-(2-chloroacetamido)-4-(3'-methylanilino)quinazoline (0.775 g), m.p. >290° C. NMR Spectrum: (CD$_3$SOCD$_3$) 2.32 (s, 3H), 4.33 (s, 2H), 6.94 (d, 1H), 7.25 (t, 1H), 7.6 (m, 2H), 7.75 (d, 1H), 7.84 (m, 1H), 8.50 (s, 1H), 8.68 (d, 1H), 9.80 (s, 1H), 10.57 (s, 1H); Elemental Analysis: Found C, 62.6; H, 4.5; N, 17.1; C$_{17}$H$_{15}$ClN$_4$O requires C, 62.5; H, 4.6; N, 17.1%.

Example 61

Sodium cyanoborohydride (0.2 g) was added portionwise to a mixture of 6-amino-4-(3'-methylanilino)quinazoline (0.5 g), formaldehyde (37% solution in water, 0.8 ml) and acetonitrile (15 ml). The mixture was stirred at ambient temperature for 45 minutes. The mixture was neutralised by the addition of glacial acetic acid and evaporated. The residue was partitioned between methylene chloride and 2N aqueous sodium hydroxide. The organic phase was dried (MgSO$_4$) and evaporated. The residue was purified by column chromatography using increasingly polar mixtures of methylene chloride and methanol as eluent. There was thus obtained 6-dimethylamino-4-(3'-methylanilino)quinazoline (0.237 g), m.p. >200° C. (decomposes). NMR Spectrum: (CD$_3$SOCD$_3$) 2.33 (s, 3H), 3.06 (s, 6H), 6.95 (d, 1H), 7.26 (t, 1H), 7.41 (s, 1H), 7.48 (d, 1H), 7.6 (m, 2H), 7.65 (d, 1H), 8.37 (s, 1H), 9.5 (s, 1H); Elemental Analysis: Found C, 71.2; H, 6.3; N, 19.4; C$_{17}$H$_{18}$N$_4$. 0.4H$_2$O requires C, 71.5; H, 6.6; N, 19.6%.

Example 62

Using an analogous procedure to that described in Example 39, except that DMA was used in place of DMF and that the reaction mixture was heated to 80° C. for 4 hours, 6-hydroxy-4-(3'-methylanilino)quinazoline was reacted with 1,2-dibromoethane to give 6-(2-bromoethoxy)-4-(3'-methylanilino)quinazoline in 47% yield, m.p. 129°–135° C. NMR Spectrum: (CD$_3$SOCD$_3$) 2.35 (s, 3H), 3.92 (t, 2H), 4.52 (t, 2H), 6.95 (d, 1H), 7.28 (t, 1H), 7.53 (m, 1H), 7.63 (m, 2H), 7.74 (d, 1H), 7.96 (d, 1H), 8.49 (s, 1H), 9.52 (s, 1H); Elemental Analysis: Found C, 57.5; H, 4.2; N, 11.57 C$_{17}$H$_{16}$BrN$_3$O requires C, 57.0; H, 4.5; N, 11.7%.

Example 63

The procedure described in Example 62 was repeated except that 2-bromoethyl methyl ether was used in place of 1,2-dibromoethane. There was thus obtained 6-(2-methoxyethoxy)-4-(3'-methylanilino)quinazoline in 52% yield, m.p. 177°–179° C. NMR Spectrum: (CD$_3$SOCD$_3$) 2.35 (s, 3H), 3.36 (s, 3H), 3.76 (t, 2H), 4.29 (t, 2H), 6.95 (d, 1H), 7.28 (m, 1H), 7.51 (m, 1H), 7.62 (s, 1H), 7.65 (d, 1H), 7.72 (d, 1H), 7.95 (d, 1H), 8.49 (s, 1H); Elemental Analysis: Found C, 69.4; H, 6.2; N, 13.2; C$_{18}$H$_{19}$N$_3$O$_2$. 0.1H$_2$O requires C, 69.4; H, 6.2; N, 13.5%.

Example 64

Dimethylamine gas was led into a stirred solution of 6-(2-bromoethoxy)-4-(3'-methylanilino)quinazoline (0.237 g) in DMA (5 ml) and the mixture was stirred at ambient temperature for 16 hours. The mixture was evaporated and the residue was purified by column chromatography using increasingly polar mixtures of methylene chloride and methanol as eluent. There was thus obtained 6-(2-dimethylaminoethoxy)-4-(3'-methylanilino)quinazoline hydrobromide (0.177 g), m.p. 83°–86° C. NMR Spectrum: (CD$_3$SOCD$_3$) 2.35 (s, 3H), 2.5 (s, 6H), 3.09 (t, 2H), 4.35 (t, 2H), 6.96 (d, 1H), 7.29 (m, 1H), 7.50 (m, 1H), 7.62 (m, 2H), 7.64 (d, 1H), 7.98 (d, 1H), 8.49 (s, 1H), 9.54 (s, 1H); Elemental Analysis: Found C, 56.6; H, 5.9; N, 13.6; C$_{19}$H$_{22}$N$_4$O. 1HBr requires C, 56.6; H, 5.7; N, 13.9%.

Example 65

Sodium cyanide (0.121 g) and triethylamine (0.303 g) were added in turn to a mixture of 6-bromomethyl-4-(3'-methylanilino)quinazoline (0.3 g) and DMA (5 ml). The mixture was stirred at ambient temperature for 16 hours. The mixture was evaporated and the residue was purified by column chromatography using increasingly polar mixtures of methylene chloride and ethyl acetate as eluent. There was thus obtained 6-cyanomethyl-4-(3'-methylanilino)quinazoline as a solid (0.084 g). NMR Spectrum: (CD$_3$SOCD$_3$) 2.34 (s, 3H), 4.24 (s, 2H), 6.98 (d, 1H), 7.29 (t, 1H), 7.61 (m, 2H), 7.83 (s, 2H), 8.56 (s, 1H), 8.62 (s, 1H); Elemental Analysis: Found C, 72.7; H, 4.9; N, 19.6; C$_{17}$H$_{14}$N$_4$. 0.33H$_2$O requires C, 72.8; H, 5.2; N, 20.0%.

Example 66

Di-(1-imidazolyl) ketone (0.421 g) was added to a mixture of 7-carboxy-4-(3'-methylanilino)quinazoline (0.558 g), THF (40 ml) and DMF (20 ml). The mixture was stirred and heated to 40° C. for 90 minutes. The mixture was cooled to 5° C. and dimethylamine was led into the mixture for 40 minutes. The mixture was evaporated and the residue was triturated under water. The solid so obtained was isolated and dried. There was thus obtained 7-(N,N-dimethyl-carbamoyl)-4-(3'-methylanilino)quinazoline (0.55 g), m.p. 207°–209° C. NMR Spectrum: (CD$_3$SOCD$_3$+CD$_3$CO$_2$D) 2.35 (s, 3H), 2.96 (s, 3H), 3.07 (s, 3H), 7.04 (d, 1H), 7.32 (t, 1H), 7.63 (m, 1H), 7.66 (s, 2H), 7.82 (d, 1H), 8.60 (d, 1H), 8.64 (s, 1H); Elemental Analysis: Found C, 69.6; H, 5.8; N, 18.1; $C_{18}H_{18}N_4O$ 0.2H$_2$O requires C, 69.8; H, 5.9; N, 18.1%.

Example 67

Using an analogous procedure to that described in Example 1, 4-chloro-6-morpholinoquinazoline was reacted with 3-methylaniline to give 4-(3'-methylanilino)-6-morpholinoquinazoline hydrochloride in 76% yield, m.p. 276°–278° C. NMR Spectrum: (CD$_3$SOCD$_3$) 2.38 (s, 3H), 3.41 (m, 4H), 3.82 (m, 4H), 7.18 (d, 1H), 7.38 (m, 1H), 7.48 (s, 1H), 7.50 (d, 1H), 7.87 (s, 2H), 8.08 (s, 1H), 8.75 (s, 1H); Elemental Analysis: Found C, 63.9; H, 6.0; N, 15.4; $C_{19}H_{20}N_4O$ 1HCl requires C, 64.1; H, 5.9; N, 15.8%.

The 4-chloro-6-morpholinoquinazoline used as a starting material was obtained as follows:

A mixture of 5-chloro-2-nitrobenzoic acid (20.2 g) and morpholine (50 ml) was stirred and heated to reflux for 3 hours. The mixture was evaporated. Water (100 ml) was added and the mixture was acidified to pH2 by the addition of concentrated hydrochloric acid. The precipitate was isolated, washed with water and dried. There was thus obtained 2-nitro-5-morpholinobenzoic acid (24.3 g).

A mixture of a portion (10 g) of the material so obtained, 10% palladium-on-charcoal catalyst (1 g) and DMA (150 ml) was heated to 40° C. and stirred under an atmosphere of hydrogen for 4 hours. The mixture was filtered and the filtrate was evaporated. The residue was triturated under diethyl ether to give 5-morpholinoanthranilic acid (6.05 g).

A mixture of a portion (5.5 g) of the material so obtained and formamide (20 ml) was stirred and heated to 170° C. for 4 hours. The mixture was cooled to ambient temperature and the precipitate was isolated, washed in turn with formamide, ethyl acetate and diethyl ether and dried. There was thus obtained 6-morpholinoquinazolin-4-one (4.8 g), m.p. 270°–273° C.

Phosphoryl chloride (0.664 g) was added to a stirred mixture of 6-morpholinoquinazoline (0.5 g), N,N-dimethylaniline (0.471 g) and toluene (10 ml). The mixture was heated to reflux for 1 hour. The mixture was cooled to ambient temperature, diluted with toluene (25 ml) and extracted with dilute aqueous ammonium chloride solution. The organic phase was dried (MgSO$_4$) and evaporated. The residue was purified by column chromatography using increasingly polar mixtures of methylene chloride and ethyl acetate as eluent. There was thus obtained 4-chloro-6-morpholinoquinazoline as a solid (0.52 g).

Example 68

A mixture of 4-chloro-6,7-dimethoxyquinazoline (0.449 g), 1,3-phenylenediamine (0.433 g) and THF (16 ml) was stirred and heated to reflux for 20 hours. The mixture was cooled to ambient temperature. The precipitate was isolated, washed with diethyl ether and dried. There was thus obtained 4-(3'-aminoanilino)-6,7-dimethoxy-quinazoline hydrochloride (0.367 g), m.p. 242°–243° C. NMR Spectrum: (CD$_3$SOCD$_3$) 3.97 (s, 3H), 4.0 (s, 3H), 6.64 (m, 1H), 6.95 (d, 1H), 7.02 (d, 1H), 7.16 (t, 1H), 7.87 (s, 1H), 8.25 (s, 1H), 8.72 (s, 1H), 10.99 (broad s, 1H); Elemental Analysis: Found C, 57.6; H, 5.0; N, 16.4; $C_{16}H_{16}N_4O_2$. 1HCl. 0.1H$_2$O requires C, 57.4; H, 5.2; N, 16.7%.

Example 69

Using an analogous procedure to that described in Example 68, 4-chloro-6,7-dimethoxyquinazoline was reacted with 3-aminophenol to give 4-(3'-hydroxyanilino)-6,7-dimethoxyquinazoline in 92% yield, m.p. 256°–257° C. NMR Spectrum: 3.98 (s, 3H), 4.02 (s, 3H), 6.75 (m, 1H), 7.12 (d, 1H), 7.14 (d, 1H), 7.25 (t, 1H), 7.42 (s, 1H), 8.37 (s, 1H), 8.80 (s, 1H), 9.5 (broad hump, 1H), 11.4 (broad s, 1H); Elemental Analysis: Found C, 57.1; H, 4.8; N, 12.1; $C_{16}H_{15}N_3O_3$. 1HCl. 0.25H$_2$O requires C, 56.8; H, 4.9; N, 12.4%.

Example 70

A mixture of 4-chloro-6-piperidinoquinazoline (0.371 g), 3,4-dichloroaniline (0.243 g), isopropanol (3 ml) and THF (4 ml) was stirred and heated to reflux for 3 hours. The mixture was allowed to cool to ambient temperature. The precipitate was isolated, washed with THF and diethyl ether and dried. There was thus obtained 4-(3',4'-dichloroanilino)-6-piperidinoquinazoline hydrochloride (0.331 g, 54%), m.p. >280° C. NMR Spectrum: (CD$_3$SOCD$_3$) 1.68 (m, 6H), 3.49 (m, 4H), 7.7–8.0 (m, 5H), 8.13 (s, 1H), 8.81 (s, 1H); Elemental Analysis: Found C, 56.4; H, 4.7; N, 13.6; $C_{19}H_{18}Cl_2N_4$. 0.9HCl requires C, 56.3; H, 4.7; N, 13.8%.

The 4-chloro-6-piperidinoquinazoline used as a starting material was obtained as follows:

A mixture of 5-chloro-2-nitrobenzoic acid (13.7 g), piperidine (27 ml) and DMA (100 ml) was stirred and heated to 120° C. for 18 hours. The mixture was evaporated. The residue was dissolved in water and the solution was basified to pH10 by the addition of 2N aqueous sodium hydroxide solution. The solution was extracted with ethyl acetate. The aqueous layer was acidified to pH2 by the addition of concentrated hydrochloric acid and extracted with ethyl acetate. The organic layer was dried (MgSO$_4$) and evaporated to give 2-nitro-5-piperidinobenzoic acid (16.25 g), m.p.130°–140° C.

A mixture of a portion (10 g) of the material so obtained, 10% palladium-on-charcoal catalyst (1 g) and DMA (150 ml) was heated to 40° C. and stirred under an atmosphere of hydrogen for 4 hours. The mixture was filtered and the filtrate was evaporated. There was thus obtained 5-piperidinoanthranilic acid as an oil (12.1 g) which was used without further purification.

A mixture of the material so obtained and formamide (50 ml) was stirred and heated to 170° C. for 90 minutes. The mixture was allowed to cool to ambient temperature. The precipitate was isolated, washed with formamide and with diethyl ether and dried. There was thus obtained 6-piperidinoquinazolin-4-one (5.95 g), m.p. 160°–166° C.

Phosphoryl chloride (5.37 g) was added to a stirred mixture of 6-piperidinoquinazoline (4 g), N,N-dimethylaniline (3.81 g) and toluene (70 ml). The mixture was heated to reflux for 2 hours. The mixture was allowed to cool to ambient temperature, diluted with toluene (80 ml) and extracted with dilute aqueous ammonium chloride solution. The organic phase was dried (MgSO$_4$) and evaporated. The residue was purified by column chromatography using increasingly polar mixtures of methylene chloride and ethyl acetate as eluent. There was thus obtained 4-chloro-6-piperidinoquinazoline as a solid (2.01 g).

Example 71

A mixture of 7-methylamino-4-(3'-methylanilino)-6-nitroquinazoline (1 g), 10% palladium-on-charcoal catalyst (0.1 g) and DMA (20 ml) was stirred and heated to 50° C. under an atmosphere of hydrogen for 3 hours. The mixture was cooled to ambient temperature and filtered. The filtrate was evaporated and the residue was partitioned between methylene chloride and aqueous ammonium hydroxide solution. The organic phase was dried (MgSO$_4$) and evaporated. The residue was purified by column chromatography using increasingly polar mixture of methylene chloride and methanol as eluent. There was thus obtained 6-amino-7-methylamino-4-(3'-methylanilino)quinazoline (0.056 g, 6%), m.p. 229°–232° C. NMR Spectrum: (CD$_3$SOCD$_3$) 2.31 (s, 3H), 2.86 (d, 3H), 5.10 (broad s, 2H), 5.98 (broad s, 1H), 6.65 (s, 1H), 6.84 (d, 1H), 7.20 (m, 1H), 7.32 (s, 1H), 7.60 (d, 1H), 7.62 (s, 1H), 8.29 (s, 1H), 9.10 (broad s, 1H Elemental Analysis: Found C, 65.9; H, 5.8; N, 23.8; C$_{16}$H$_{17}$N$_5$. 0.1H$_2$O. 0.15CH$_2$Cl$_2$ requires C, 66.2; H, 5.9; N, 23.7%.

The 7-methylamino-4-(3'-methylanilino)-6-nitroquinazoline used as a starting material was obtained as follows:

A mixture of 7-chloro-4-(3'-methylanilino)-6-nitroquinazoline (10.5 g), an ethanolic solution of methylamine (30% weight/volume; 100 ml) and ethanol (100 ml) was stirred at ambient temperature for 16 hours. The mixture was evaporated to give the required starting material which was used without further purification.

Example 72

Tert-butyl nitrite (0.051 g) was added to a mixture of 6-amino-4-(3'-methylanilino)-7-morpholinoquinazoline (0.167 g) and DMF (5 ml) which had been heated to 65° C. The mixture was heated to 65° C. for 30 minutes. A second portion (0.051 g) of tert-butyl nitrite was added and the mixture was stirred at ambient temperature for 65 hours. The mixture was evaporated and the residue was purified by reversed-phase column chromatography using a 60:40:0.2 mixture of methanol, water and trifluoroacetic acid as eluent. There was thus obtained 4-(3'-methylanilino)-7-morpholinoquinazoline (0.066 g, 41%), m.p. 227°–229° C. NMR Spectrum: (CD$_3$SOCD$_3$) 2.33 (s, 3H), 3.50 (m, 4H), 3.82 (m, 4H), 6.93 (d, 1H), 7.14 (d, 1H), 7.56 (d, 1H), 7.57 (s, 1H), 7.59 (m, 1H), 8.49 (d, 1H), 8.75 (s, 1H), 10.93 (broad s, 1H).

The 6-amino-4-(3'-methylanilino)-7-morpholinoquinazoline used as a starting material was obtained as follows:

A mixture of 7-chloro-4-(3'-methylanilino)-6-nitroquinazoline (1 g) and morpholine (0.306 ml) was stirred and heated to 70° C. for 3 hours. The mixture was evaporated and the residue was triturated under methylene chloride. There was thus obtained 4-(3'-methylanilino)-7-morpholino-6-nitroquinazoline (1.02 g), m.p. 212°–215° C. NMR Spectrum: (CD$_3$SOCD$_3$) 2.34 (s, 3H), 3.11 (t, 4H), 3.74 (t, 4H), 6.97 (d, 1H), 7.28 (t, 1H), 7.31 (s, 1H), 7.62 (s, 1H), 7.64 (d, 1H), 8.58 (s, 1H), 9.19 (s, 1H), 9.90 (broad s, 1H); Elemental Analysis: Found C, 55.7; H, 16.4; N, 4.7; C$_{19}$H$_{19}$N$_5$O$_3$. 0.73CH$_2$Cl$_2$ requires C, 55.4; H, 16.4; N, 4.6%.

Using an analogous procedure to that described in Example 70 except that the reaction was conducted at ambient temperature, 4-(3'-methylanilino)-7-morpholino-6-nitroquinazoline was reduced to give 6-amino-4-(3'-methylanilino-7-morpholinoquinazoline in 48% yield, m.p. 211°–213° C. NMR Spectrum: (CD$_3$SOCD$_3$) 2.32 (s, 3H), 2.98 (m, 4H), 3.84 (m, 4H), 5.24 (broad s, 2H), 6.92 (d, 1H), 7.18 (s, 1H), 7.25 (t, 1H), 7.52 (s, 1H), 7.62 (d, 2H), 8.38 (s, 1H), 9.37 (broad s, 1H); Elemental Analysis: Found C, 67.7; H, 6.4; N, 20.5; C$_{19}$H$_{21}$N$_5$O requires C, 68.0; H, 6.3; N, 20.9%.

Example 73

Using an analogous procedure to that described in Example 1 except that the reaction mixture was heated to reflux for 2 hours, the appropriate 4-chloroquinazoline was reacted with the appropriate aniline to give, as hydrochloride salts (unless otherwise stated), the compounds described in the following table, the structures of which were confirmed by proton magnetic resonance spectroscopy and by elemental analysis.

TABLE IV

| Example 73 Compd. No. | (R$^1$)$_m$ | (R$^2$)$_n$ | m.p. (°C.) |
|---|---|---|---|
| 1[a] | 6,7-dimethoxy | 3'-cyano | >240 |
| 2[b] | 6,7-dimethoxy | 3'-acetyl | >240 |
| 3[c] | 6,7-dimethoxy | 2',6'-difluoro | >240 |
| 4[d] | 6-piperidino | 3'-methyl | 230–232 |

Notes a. The product, obtained initially as the hydrochloride salt, was converted into the corresponding free base as follows. The salt was treated with a mixture of methylene chloride and 1N aqueous sodium hydroxide solution. The mixture was filtered and the solid so isolated was washed with a 10:1 mixture of methylene chloride and methanol and dried. There was thus obtained the required free base, m.p. >240° C.; NMR Spectrum: (CD$_3$SOCD$_3$) 3.97 (s, 3H), 4.0 (s, 3H), 7.22 (s, 1H), 7.55 (m, 1H), 7.62 (m, 1H), 7.83 (s, 1H), 8.16 (m, 1H), 8.38 (m, 1H), 8.56 (s, 1H), 9.67 (broad s, 1H); Elemental Analysis: Found C, 66.0; H, 4.6; N, 18.0; C$_{17}$H$_{14}$N$_4$O$_2$. 0.2H$_2$O requires C, 65.9; H, 4.7; N, 18.1%.

b. The product gave the following analytical data: Found C, 58.3; H, 5.0; N, 11.2; C$_{18}$H$_{17}$N$_3$O$_3$. 1HCl. 0.5H$_2$O requires C, 58.6; H, 5.2; N, 11.4%; and the following characteristic NMR data: 2.62 (s, 3H), 3.99 (s, 3H), 4.04 (s, 3H), 7.43 (s, 1H), 7.62 (m, 1H), 7.90 (m, 1H), 8.05 (m, 1H), 8.29 (m, 1H), 8.47 (s, 1H), 8.84 (s, 1H), 11.74 (broad s, 1H).

c. The product, obtained initially as the hydrochloride salt, was converted into the corresponding free base as follows. The salt was partitioned between ethyl acetate and 1N aqueous sodium hydroxide solution. The organic phase was washed with brine, dried (MgSO$_4$) and evaporated. The residue was purified by column chromatography using a 19:1 mixture of methylene chloride and methanol as eluent. There was thus obtained the required free base, m.p. >240° C.; NMR Spectrum: (CD$_3$SOCD$_3$) 3.82 (s, 6H), 7.05–7.35 (m, 3H), 7.72 (s, 1H), 8.21 (s, 1H), 9.34 (broad s, 1H); Elemental Analysis: Found C, 60.6; H, 4.1; N, 13.4; C$_{16}$H$_{13}$F$_2$N$_3$O$_2$ requires C, 60.6; H, 4.1; N, 13.2%.

d. The product gave the following analytical data: Found C, 67.8; H, 6.9; N, 15.3; C$_{20}$H$_{22}$N$_4$. 1.03 HCl requires C, 67.4; H, 6.5; N, 15.7%; and the following characteristic NMR data: (CD$_3$SOCD$_3$) 1.63 (m, 6H), 2.35 (s, 3H), 3.45 (m, 4H), 7.13 (d, 1H), 7.36 (m, 1H), 7.45 (m, 2H), 7.75 (d, 1H), 7.84 (m, 1H), 8.69 (s, 1H), 8.88 (d, 1H), 11.2 (broad s, 1H).

Example 74

A mixture of 4-chloro-6,7-dimethoxyquinazoline (0.674 g), 1,2-phenylenediamine (0.649 g) and THF (24 ml) was stirred and heated to reflux for 40 hours. The mixture was cooled to ambient temperature. The precipitate was isolated, washed with diethyl ether and dried. There was thus obtained 4-(2'-aminoanilino)-6,7-dimethoxyquinazoline hydrochloride (0.83 g, 83%), m.p. 241°–243° C. NMR Spectrum; (CD$_3$SOCD$_3$) 3.98 (s, 6H), 6.68 (m, 1H), 6.87 (d, 1H), 7.12 (m, 2H), 7.40 (s, 1H), 8.29 (s, 1H), 8.68 (s, 1H), 11.05 (broad s, 1H); Elemental Analysis: Found C, 57.9; H, 5.2; N, 16.6; C$_{16}$H$_{16}$N$_4$O$_2$. 1HCl requires C, 57.7; H, 5.15; N, 16.8%.

Example 75

Using an analgous procedure to that described in Example 74, 4-chloro-6,7-dimethoxyquinazoline was reacted with 1,4-phenylenediamine to give 4-(4'-aminoanilino)-6,7-dimethoxyquinazoline hydrochloride in 85% yield, m.p. 274°–276° C. NMR Spectrum: (CD$_3$SOCD$_3$) 3.95 (s, 3H), 3.98 (s, 3H), 6.75 (d, 2H), 7.35 (s, 1H), 7.38 (d, 2H), 8.25 (s, 1H), 8.67 (s, 1H), 11.05 (broad s, 1H); Elemental Analysis: Found C, 57.6; H, 5.0; N, 16.9; C$_{16}$H$_{16}$N$_4$O$_2$. 1HCl requires C, 57.7; H, 5.15; N, 16.8%.

Example 76

Sodium cyanoborohydride (0.013 g) was added to a mixture of 6-amino-4-(3'-methylanilino)quinazoline (0.5 g), formaldehyde (37% solution in water, 0.16 ml) and DMA (5 ml). The mixture was stirred at ambient temperature for 1 hour. The mixture was neutralised by the addition of glacial acetic acid. The mixture was evaporated and the residue was purified by column chromatography using increasingly polar mixtures of methylene chloride and methanol as eluent. There was thus obtained 6-methylamino-4-(3'-methylanilino)quinazoline (0.15 g, 28%), m.p. 99°–102° C. NMR Spectrum: (CD$_3$SOCD$_3$) 2.34 (s, 3H), 2.85 (d, 3H), 6.32 (q, 1H), 6.96 (d, 1H), 7.20 (d, 1H), 7.28 (m, 2H), 7.54 (d, 1H), 7.6 (m, 2H), 8.48 (s, 1H), 9.52 (broad s, 1H); Elemental Analysis: Found C, 70.8; H, 5.9; N, 20.5; C$_{16}$H$_{16}$N$_4$. 0.4H$_2$O requires C, 70.7; H, 6.2; N, 20.6%.

Example 77

A mixture of 6-amino-4-(3'-methylanilino)quinazoline (0.05 g), benzaldehyde (0.02 ml) and methanol (5 ml) was stirred and heated to reflux for 1 hour. The mixture was cooled to ambient temperature and sodium borohydride (0.0076 g) was added portionwise. The mixture was stirred at ambient temperature for 16 hours. The mixture was evaporated and the residue was purified by column chromatography using a 4:1 mixture of methylene chloride and ethyl acetate as eluent. There was thus obtained 6-benzylamino-4-(3'-methylanilino)quinazoline (0.068 g). NMR Spectrum: (CD$_3$SOCD$_3$) 2.35 (s, 3H), 4.36 (d, 1H), 6.67 (t, 1H), 6.93 (d, 1H), 7.2–7.7 (m, 11H), 8.33 (s, 1H), 9.26 (broad s, 1H); Elemental Analysis: Found C, 77.3; H, 6.1; N, 16.0; C$_{22}$H$_{20}$N$_4$. 0.125H$_2$O requires C, 77.1; H, 5.9; N, 16.4%.

Example 78

DMA (3 ml) was saturated with dimethylamine gas and 6-(2-chloroacetamido)-4-(3'-methylanilino)quinazoline (0.2 g) was added. The mixture was stirred at ambient temperature for 18 hours. The mixture was evaporated and the residue was purified by column chromatography using increasingly polar mixtures of methylene chloride and methanol as eluent. There was thus obtained 6-(2-dimethylaminoacetamido)-4-(3'-methylanilino)quinazoline (0.127 g, 62%), m.p. 146°–148° C. NMR Spectrum: (CD$_3$SOCD$_3$) 2.32 (s, 9H), 3.14 (s, 2H), 6.94 (d, 1H), 7.26 (t, 1H), 7.65 (m, 2H), 7.75 (d, 1H), 8.13 (m, 1H), 8.53 (s, 1H), 8.61 (d, 1H), 9.64 (broad s, 1H), 9.89 (broad s, 1H); Elemental Analysis: Found C, 67.7; H, 6.5; N, 20.6; C$_{19}$H$_{21}$N$_5$O requires C, 68.0; H, 6.3; N, 20.9%.

Example 79

Using an analogous procedure to that described in Example 11, 4-(3'-aminoanilino)-6,7-dimethoxyquinazoline hydrochloride was reacted with acetic anhydride. The crude product was purified by column chromatography using a 150:8:1 mixture of methylene chloride, methanol and ammonia as eluent. There was thus obtained 4-(3'-acetamidoanilino)-6,7-dimethoxyquinazoline in 47% yield, m.p. 252°–255° C. NMR Spectrum: (CD$_3$SOCD$_3$) 2.06 (s, 3H), 3.94 (s, 3H), 3.96 (s, 3H), 7.18 (s, 1H), 7.27-7.35 (m, 2H), 7.45 (m, 1H), 7.87 (s, 1H), 8.06 (s, 1H), 8.45 (s, 1H), 9.5 (broad s, 1H}, 9.9 (broad s, 1H); Elemental Analysis: Found C, 62.9; H, 5.5; N, 16.1; C$_{18}$H$_{18}$N$_4$O$_3$. 0.25H$_2$O requires C, 63.1; H, 5.4; N, 16.3%.

Example 80

A mixture of 4-(3'-aminoanilino)-6,7-dimethoxyquinazoline hydrochloride (0.083 g), benzoyl chloride (0.042 g), triethylamine (0.101 g) and DMF (1.5 ml) was stirred at ambient temperature for 20 hours. The mixture was evaporated and the residue was purified by column chromatography using a 100:8:1 mixture of methylene chloride, methanol and ammonia as eluent. There was thus obtained 4-(3'-benzamidoanilino)-6,7-dimethoxyquinazoline (0.15 g, 15%), m.p. 239°–242° C. NMR Spectrum: (CD$_3$SOCD$_3$) 3.92 (s, 3H), 3.96 (s, 3H), 7.18 (s, 1H), 7.34 (t, 1H), 7.45–7.63 (m, 5H), 7.87 (s, 1H), 7.96 (m, 2H), 8.26 (t, 1H), 8.45 (s, 1H), 9.52 (broad s, 1H), 10.29 (broad s, 1H); Elemental Analysis: Found C, 65.9; H, 5.3; N, 13.0; C$_{23}$H$_{20}$N$_4$O$_3$. 0.3CH$_3$OH. 0.75H$_2$O requires C, 66.1; H, 5.4; N, 13.2%.

Example 81

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| -continued | |
|---|---|
| (d) Capsule | mg/capsule |
| Compound X | 10 |
| Lactose Ph. Eur | 488.5 |
| Magnesium stearate | 1.5 |
| (e) Injection I | (50 mg/ml) |
| Compound X | 5.0% w/v |
| 1M Sodium hydroxide solution | 15.0% w/v |
| 0.1M Hydrochloric acid (to adjust pH to 7.6) | |
| Polyethylene glycol 400 | 4.5% w/v |
| Water for injection to 100% | |
| (f) Injection II | 10 mg/ml) |
| Compound X | 1.0% w/v |
| Sodium phosphate BP | 3.6% w/v |
| 0.1M Sodium hydroxide solution | 15.0% w/v |
| Water for injection to 100% | |
| (g) Injection III | (1 mg/ml, buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

CHEMICAL FORMULAE

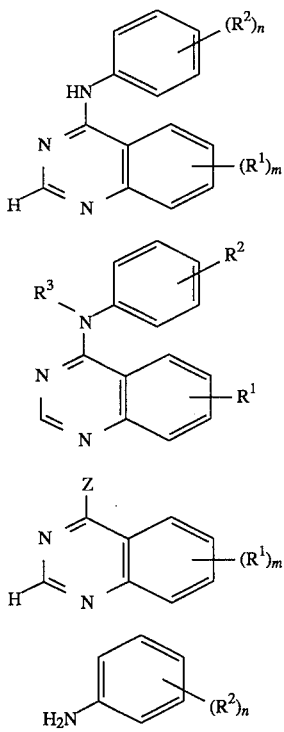

I claim:
1. A quinazoline derivative of the formula I

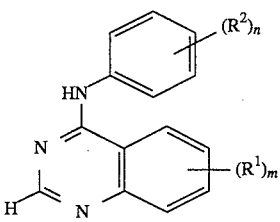

wherein m is 1, 2 or 3 and each $R^1$ is independently 6-hydroxy, 7-hydroxy, amino, carboxy, carbamoyl, ureido, (1-4C)alkoxycarbonyl, N-(1-4C)alkylcarbamoyl, N,N-di-[(1-4C)alkyl]carbamoyl, hydroxyamino, (1-4C)alkoxyamino, (2-4C)alkanoyloxyamino, trifluoromethoxy, (1-4C)alkyl, 6-(1-4C)alkoxy, 7-(1-4C)alkoxy, (1-3C)alkylenedioxy, (1-4C)alkylamino, di-l[(1-4C)alkyl]amino, pyrrolidin-1-yl, piperidino, morpholino, piperazin-1-yl, 4-(1-4C)alkylpiperazin-1-yl, (1-4C)alkylthio, (1-4C)alkylsulphinyl, (1-4C)alkylsulphonyl, bromomethyl, dibromomethyl, hydroxy-(1-4C)alkyl, (2-4C)alkanoyloxy-(1-4C)alkyl, (1-4C)alkoxy-(1-4C)alkyl, carboxy-(1-4C)alkyl, (1-4C)alkoxycarbonyl-(1-4C)alkyl, carbamoyl-(1-4C)alkyl, N-(1-4C)alkylcarbamoyl-(1-4C)alkyl, N, N-di[(1-4C)alkyl]carbamoyl-(1-4C)alkyl, amino-(1-4C)alkyl, (1-4C)alkylamino-(1-4C)alkyl, di-[(1-4C)alkyl]amino-(1-4C)alkyl, piperidino-(1-4C)alkyl, morpholino-(1-4C)alkyl, piperazin-1-yl-(1-4C) alkyl, 4-(1-4C)alkylpiperazin-1-yl-(1-4C) alkyl, hydroxy-(2-4C)alkoxy-(1-4C) alkyl, (1-4C)alkoxy-(2-4C)alkoxy-( 1-4C)alkyl, hydroxy-(2-4C)alkylamino-(1-4C)alkyl, (1-4C)alkoxy-(2-4C)alkylamino-(1-4C)alkyl, (1-4C)alkylthio-( 1-4C)alkyl, hydroxy-(2-4C)alkylthio-(1-4C)alkyl, (1-4C)alkoxy-(2-4C)alkylthio-(1-4C)alkyl, phenoxy-(1-4C)alkyl, anilino-(1-4C)alkyl, phenylthio-(1-4C)alkyl, cyano-(1-4C)alkyl, halogeno-(2-4C)alkoxy, hydroxy-(2-4C)alkoxy, (2-4C)alkanoyloxy-(2-4C)alkoxy, (1-4C)alkoxy-(2-4C)alkoxy, carboxy-(1-4C)alkoxy, (1-4C)alkoxycarbonyl-(1-4C)alkoxy, carbamoyl-(1-4C)alkoxy, N-(1-4C) alkylcarbamoyl-(1-4C)alkoxy, N, N-di-[(1-4C)alkyl]carbamoyl-(1-4C)alkoxy, amino-(2-4C)alkoxy, (1-4C)alkylamino-(2-4C)alkoxy, di-[(1-4C)alkyl]amino-(2-4C)alkoxy, (2-4C)alkanoyloxy, hydroxy-(2-4C)alkanoyloxy, (1-4C)alkoxy-(2-4C)alkanoyloxy, phenyl-(1-4C)alkoxy, phenoxy-(2-4C)alkoxy, anilino-(2-4C)alkoxy, phenylthio-(2-4C)alkoxy, piperidino-(2-4C)alkoxy, morpholino-(2-4C)alkoxy, piperazin-1-yl-(2-4C)alkoxy, 4-(1-4C)alkylpiperazin-1-yl-(2-4C)alkoxy, halogeno-(2-4C)alkylamino, hydroxy-(2-4C)alkylamino, (2-4C)alkanoyloxy-(2-4C)alkylamino, (1-4C)alkoxy-(2-4C)alkylamino, carboxy-(1-4C)alkylamino, (1-4C)alkoxycarbonyl-(1-4C)alkylamino, carbamoyl-(1-4C)alkylamino, N-(1-4C)alkylcarbamoyl-(1-4C)alkylamino, N, N-di-[(1-4C)alkyl]carbamoyl-(1-4C)alkylamino, amino-(2-4C)alkylamino, (1-4C)alkylamino-(2-4C)alkylamino, di-1(1-4C)alkyl]amino-(2-4C)alkylamino, phenyl-(1-4C)alkylamino, phenoxy-(2-4C)alkylamino, anilino-(2-4C)alkylamino, phenylthio-(2-4C)alkylamino, (2-4C)alkanoylamino, (1-4C)alkoxycarbonylamino, (1-4C)alkylsulphonylamino, benzamido, benzenesulphonamido, 3-phenylureido, 2-oxopyrrolidin-1-yl, 2,5-dioxopyrrolidin-1-yl, halogeno-(2-4C)alkanoylamino, hydroxy-(2-4C)alkanoylamino, (1-4C)alkoxy-(2-4C)alkanoylamino, carboxy-(2-4C)alkanoylamino, (1-4C)alkoxycarbonyl-(2-4C)alkanoylamino, carbamoyl-(2-4C)alkanoylamino, N-(1-4C)alkylcarbamoyl-(2-4C)alkanoylamino, N,N-di-[(1-4C)alkyl]carbamoyl-(2-4C)alkanoylamino, amino-(2-4C)alkanoylamino, (1-4C)alkylamino-(2-4C)alkanoylamino or di-[(1-4C)alkyl]amino-(2-4C)alkanoylamino, and wherein said benzamido or benzenesulphonamido substituent or any anilino, phenoxy or phenyl group in a $R^1$ substituent may optionally bear one or two halogeno, (1-4C)alkyl or (1-4C)alkoxy substituents; n is 1 or 2 and each $R^2$ is independently hydrogen, hydroxy, halogeno, trifluoromethyl, amino, nitro, cyano, (1-4C)alkyl, (1-4C)alkoxy, (1-4C)alkylamino, di-[(1-4C)alkyl]amino, (1-4C)alkylthio, (1-4C)alkylsulphinyl or (1-4C)alkylsulphonyl; or a pharmaceutically-acceptable salt thereof; except that 4-(4'-hydroxyanilino)-6-methoxyquinazoline, 4-(4,-hydroxyanilino)-6,7-methylenedioxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof are excluded.

2. A quinazoline derivative of the formula I

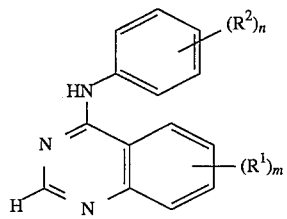

wherein m is 1, 2 or 3 and each $R^1$ is independently 6-hydroxy, 7-hydroxy, amino, carboxy, carbamoyl, ureido, (1-4C)alkoxycarbonyl, N-(1-4C)alkylcarbamoyl, N,N-di-[(1-4C)alkyl]carbamoyl, hydroxyamino, (1-4C)alkoxyamino, (2-4C)alkanoyloxyamino, trifluoromethoxy, (1-4C)alkyl, 6-(1-4C)alkoxy, 7-(1-4C)alkoxy, (1-3C)alkylenedioxy, (1-4C) alkylamino, di-[(1-4C)alkyl]amino, pyrrolidin-1-yl, piperidino, morpholino, piperazin-1-yl, 4-(1-4C)alkylpiperazin-1-yl, (1-4C)alkylthio, (1-4C)alkylsulphinyl, (1-4C)alkylsulphonyl, bromomethyl, dibromomethyl, hydroxy-(1-4C)alkyl, (2-4C)alkanoyloxy-(1-4C)alkyl, (1-4C) alkoxy-(1-4C)alkyl, carboxy-(1-4C)alkyl, (1-4C)alkoxycarbonyl-(1-4C)alkyl, carbamoyl-(1-4C)alkyl, N-(1-4C) alkylcarbamoyl-(1-4C)alkyl, N,N-di-[(1-4C)alkyl]carbamoyl-(1-4C)alkyl, amino-(1-4C)alkyl, (1-4C)alkylamino-(1-4C)alkyl, di-[(1-4C)alkyl]amino-(1-4C)alkyl, piperidino-(1-4C)alkyl, morpholino-(1-4C)alkyl, piperazin-1-yl-(1-4C)alkyl, 4-(1-4C)alkylpiperazin-1-yl-(1-4C)alkyl, hydroxy-(2-4C)alkoxy-(1-4C)alkyl, (1-4C)alkoxy-(2-4C)alkoxy-( 1-4C)alkyl, hydroxy-(2-4C)alkylamino-(1-4C)alkyl, (1-4C)alkoxy-(2-4C)alkylamino-(1-4C)alkyl, (1-4C)alkylthio-( 1-4C)alkyl, hydroxy-(2-4C)alkylthio-(1-4C)alkyl, (1-4C)alkoxy-(2-4C)alkylthio-(1-4C)alkyl, phenoxy-(1-4C)alkyl, anilino-(1-4C)alkyl, phenylthio-(1-4C)alkyl, cyano-(1-4C)alkyl, halogeno-(2-4C)alkoxy, hydroxy-(2-4C)alkoxy, (2-4C)alkanoyloxy-(2-4C)alkoxy, (1-4C)alkoxy-(2-4C)alkoxy, carboxy-(1-4C)alkoxy, (1-4C)alkoxycarbonyl-(1-4C)alkoxy, carbamoyl-(1-4C)alkoxy, N-(1-4C)alkylcarbamoyl-(1-4C)alkoxy, N,N-di-[(1-4C)alkyl]carbamoyl-(1-4C)alkoxy, amino-(2-4C)alkoxy, (1-4C)alkylamino-(2-4C)alkoxy, di-[(1-4C)alkyl]amino-(2-4C)alkoxy, (2-4C)alkanoyloxy, hydroxy-(2-4C)alkanoyloxy, (1-4C)alkoxy-(2-4C)alkanoyloxy, phenyl-(1-4C)alkoxy, phenoxy-(2-4C)alkoxy, anilino-(2-4C)alkoxy, phenylthio-(2-4C)alkoxy, piperidino-(2-4C)alkoxy, morpholino-(2-4C)alkoxy, piperazin-1-yl-(2-4C)alkoxy, 4-(1-4C)alkylpiperazin-1-yl-(2-4C)alkoxy, halogeno-(2-4C)alkylamino, hydroxy-(2-4C)alkylamino, (2-4C)alkanoyloxy-(2-4C)alkylamino, (1-4C)alkoxy-(2-4C)alkylamino, carboxy-(1-4C)alkylamino, (1-4C)alkoxycarbonyl-(1-4C)alkylamino, carbamoyl-(1-4C)alkylamino, N-(1-4C)alkylcarbamoyl-(1-4C)alkylamino, N, N-di-[(1-4C)alkyl]carbamoyl-(1-4C)alkylamino, amino-(2-4C)alkylamino, (1-4C)alkylamino-(2-4C)alkylamino, di-1[(1-4C)alkyl]amino-(2-4C)alkylamino, phenyl-(1-4C)alkylamino, phenoxy-(2-4C)alkylamino, anilino-(2-4C)alkylamino, phenylthio-(2-4C)alkylamino, (2-4C)alkanoylamino, (1-4C)alkoxycarbonylamino, (1-4C)alkylsulphonylamino, benzamido, benzenesulphonamido, 3-phenylureido, 2-oxopyrrolidin-1-yl, 2,5-dioxopyrrolidin-1-yl, halogeno-(2-4C)alkanoylamino, hydroxy-(2-4C)alkanoylamino, (1-4C)alkoxy-(2-4C)alkanoylamino, carboxy-(2-4C)alkanoylamino, (1-4C)alkoxycarbonyl-(2-4C)alkanoylamino, carbamoyl-(2-4C)alkanoylamino, N-(1-4C)alkylcarbamoyl-(2-4C)alkanoylamino, N,N-di-[(1-4C)alkyl]carbamoyl-(2-4C)alkanoylamino, amino-(2-4C)alkanoylamino, (1-4C)alkylamino-(2-4C)alkanoylamino or di-[(1-4C)alkyl]amino-(2-4C)alkanoylamino, and wherein said benzamido or benzenesulphonamido substituent or any anilino, phenoxy or phenyl group in a $R^1$ substituent may optionally bear one or two halogeno, (1-4C)alkyl or (1-4C)alkoxy substituents; n is 1 or 2 and each $R^2$ is independently hydrogen, hydroxy, halogeno, trifluoromethyl, amino, nitro, cyano, (1-4C)alkyl, (1-4C)alkoxy, (1-4C)alkylamino, di-[(1-4C)alkyl]amino, (1-4C)alkylthio, (1-4C)alkylsulphinyl, (1-4C)alkylsulphonyl, (2-4C)alkanoylamino, (2-4C)alkanoyl, or benzamido, wherein said benzamido group may optionally bear one or two halogeno, (1-4C)alkyl or (1-4C)alkoxy substituents; or a pharmaceutically-acceptable salt thereof; except that 4-(4'-hydroxyanilino)-6-methoxyquinazoline, 4-(4'-hydroxyanilino)-6,7-methylenedioxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof are excluded.

3. A quinazoline derivative of the formula I as claimed in claim 1 wherein m is 1, 2 or 3 and each $R^1$ is independently 6-hydroxy, 7-hydroxy, amino, carboxy, carbamoyl, ureido, (1-4C)alkoxycarbonyl, N-(1-4C)alkylcarbamoyl, N,N-di-[(1-4C) alkyl]carbamoyl, (1-4C)alkyl, 6-(1-4C)alkoxy, 7-(1-4C)alkoxy, (1-3C)alkylenedioxy, (1-4C)alkylamino, di-[(1-4C)alkyl]amino, (1-4C)alkylthio, (1-4C)alkylsulphinyl, (1-4C)alkylsulphonyl, bromomethyl, dibromomethyl, hydroxy-(1-4C)alkyl, (2-4C)alkanoyloxy-(1-4C)alkyl, (1-4C)alkoxy-(1-4C)alkyl, carboxy-(1-4C)alkyl, (1-4C)alkoxycarbonyl-(1-4C)alkyl, carbamoyl-(1-4C)alkyl, N-(1-4C)alkylcarbamoyl-(1-4C)alkyl, N,N-di-[(1-4C)alkyl]-carbamoyl-(1-4C)alkyl, amino-(1-4C)alkyl, (1-4C)alkylamino-(1-4C)alkyl, di-[(1-4C)alkyl]amino-(1-4C)alkyl, piperidino-(1-4C)alkyl, morpholino-(1-4C)alkyl, piperazin-1-yl-(1-4C)alkyl, 4-(1-4C)alkylpiperazin-1-yl-(1-4C)alkyl, hydroxy-(2-4C)alkoxy-(1-4C)alkyl, (1-4C)alkoxy-(2-4C)alkoxy-( 1-4C)alkyl, hydroxy-(2-4C)alkylamino-(1-4C)alkyl, (1-4C)alkoxy-(2-4C)alkylamino-(1-4C)alkyl, (1-4C)alkylthio-( 1-4C)alkyl, hydroxy-(2-4C)alkylthio-(1-4C)alkyl, (1-4C)alkoxy-(2-4C)alkylthio-(1-4C)alkyl, halogeno-(2-4C)alkoxy, hydroxy-(2-4C)alkoxy, (2-4C)alkanoyloxy-(2-4C)alkoxy, (1-4C)alkoxy-(2-4C)alkoxy, carboxy-(1-4C)alkoxy, (1-4C)alkoxycarbonyl-(1-4C)alkoxy, carbamoyl-(1-4C)alkoxy, N-(1-4C)alkylcarbamoyl-(1-4C)alkoxy, N,N-di-[(1-4C)alkyl]carbamoyl(1-4C)alkoxy, amino-(2-4C)alkoxy, (1-4c)alkylamino-(2-4C)alkoxy, di-[(1-4C)alkyl]amino-(2-4C)alkoxy, halogeno-(2-4C)alkylamino, hydroxy-(2-4C)alkylamino, (2-4C)alkanoyloxy-(2-4C)alkylamino, (1-4C)alkoxy-(2-4C)alkylamino, carboxy-(1-4C)alkylamino, (1-4C)alkoxycarbonyl-(1-4C)alkylamino, carbamoyl-(1-4C)alkylamino, N-(1-

4C)alkylcarbamoyl-(1-4C)alkylamino, N,N-di-[(1-4C)alkyl]carbamoyl-(1-4C)alkylamino, amino-(2-4C)alkylamino, (1-4C)alkylamino-(2-4C)alkylamino, di-[(1-4C)alkyl]amino-(2-4C)alkylamino, (2-4C)alkanoylamino, (1-4C)alkoxycarbonylamino, (1-4C)alkylsulphonylamino, benzamido, benzenesulphonamido, halogeno-(2-4C)alkanoylamino, hydroxy-(2-4C)alkanoylamino, (1-4C)alkoxy-(2-4C)alkanoylamino, carboxy-(2-4C)alkanoylamino, (1-4C)alkoxycarbonyl-(2-4C)alkanoylamino, carbamoyl-(2-4C)alkanoylamino, N-(1-4C)alkylcarbamoyl-(2-4C)alkanoylamino, N,N-di-[(1-4C)alkyl]carbamoyl-(2-4C)alkanoylamino, amino-(2-4C)alkanoylamino, (1-4C)alkylamino-(2-4C)alkanoylamino or di-[(1-4C)alkyl]amino-(2-4C)alkanoylamino, and wherein said benzamido or benzenesulphonamido substituent may optionally bear one or two halogeno, (1-4C)alkyl or (1-4C)alkoxy substituents; n is 1 or 2 and each $R^2$ is independently hydrogen, hydroxy, halogeno, trifluoromethyl, amino, nitro, cyano, (1-4C)alkyl, (1-4C)alkoxy, (1-4C)alkylamino, di-[(1-4C)alkyl]amino, (1-4C)alkylthio, (1-4C)alkylsulphinyl or (1-4C)alkylsulphonyl; or a pharmaceutically-acceptable salt thereof; except that 4-(4'-hydroxyanilino)-6-methoxyquinazoline, 4-(4'-hydroxyanilino)-6,7-methylenedioxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof are excluded.

4. A quinazoline derivative of the formula I as claimed in claim 1 wherein m is 1 or 2 and each $R^1$ is independently 6-hydroxy, 7-hydroxy, amino, carboxy, (1-4C)alkoxycarbonyl, (1-4C)alkyl, 6-(1-4C)alkoxy, 7-(1-4C)alkoxy, (1-3C)alkylenedioxy, (1-4C)alkylamino, di-[(1-4C)alkyl]amino, (1-4C)alkylthio, (1-4C)alkylsulphinyl, (1-4C)alkylsulphonyl, hydroxy-(1-4C)alkyl, (1-4C)alkoxy-(1-4C)alkyl, amino-(1-4C)alkyl, (1-4C)alkylamino-(1-4C)alkyl, di-[(1-4C)alkyl]amino-(1-4C)alkyl, hydroxy-(2-4C)alkoxy, (1-4C)alkoxy-(2-4C)alkoxy, carboxy-(1-4C)alkoxy, (1-4C)alkoxycarbonyl-(1-4C)alkoxy, (2-4C)alkanoylamino, (1-4C)alkylsulphonylamino, benzamido or benzenesulphonamido, and wherein said last 2 substituents may optionally bear one or two halogeno, (1-4C)alkyl or (1-4C)alkoxy substituents; n is 1 or 2 and each $R^2$ is independently hydrogen, hydroxy, halogeno, trifluoromethyl, amino, nitro, cyano, (1-4C)alkyl, (1-4C)alkoxy, (1-4C)alkylamino, di-[(1-4C)alkyl]amino, (1-4C)alkylthio, (1-4C)alkylsulphinyl or (1-4C)alkylsulphonyl; or a pharmaceutically-acceptable salt thereof; except that 4-(4'-hydroxyanilino)-6-methoxyquinazoline, 4-(4'-hydroxyanilino)-6,7-methylenedioxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof are excluded.

5. A quinazoline derivative of the formula I as claimed in claim 1 and subject to the provisos stated in claim 1 wherein m is 1, 2 or 3 and each $R^1$ is independently 6-hydroxy, 7-hydroxy, amino, ureido, methoxycarbonyl, ethoxycarbonyl, hydroxyamino, trifluoromethoxy, methyl, ethyl, a 6- or 7-methoxy, ethoxy, propoxy, isopropoxy or butoxy group, methylenedioxy, ethylenedioxy, methyl amino, ethyl amino, dimethylamino, diethylamino, piperidino, morpholino, methylthio, ethylthio, bromomethyl, dibromomethyl, methoxymethyl, piperidinomethyl, morpholinomethyl, piperazin-1-ylmethyl, methoxyethoxymethyl, methylthiomethyl, 2-hydroxyethylthiomethyl, anilinomethyl, phenylthiomethyl, cyanomethyl, 2-bromoethoxy, 2-hydroxyethoxy, 3-hydroxypropoxy, 2-methoxyethoxy, 2-ethoxyethoxy, 3-methoxypropoxy, 3-ethoxypropoxy, methoxycarbonylmethoxy, ethoxycarbonylmethoxy, carbamoylmethoxy, 2-dimethylaminoethoxy, 2-diethylaminoethoxy, 2-methoxyacetoxy, benzyloxy, 2-anilinoethoxy, 2-piperidinoethoxy, 2-morpholinoethoxy, 2-(piperazin-1-yl)ethoxy, 2-hydroxyethylamino, 3-hydroxypropylamino, 2-methoxyethylamino, 2-ethoxyethylamino, 3-methoxypropylamino, 3-ethoxypropylamino, 2-dimethylaminoethylamino, 2-diethylaminoethylamino, 3-dimethylaminopropylamino, 3-diethylaminopropylamino, acetamido, propionamido, benzamido, 3-phenylureido, 2-chloroacetamido, 2-oxopyrrolidin-1-yl, 2-hydroxyacetamido, 2-methoxyacetamido or 2-ethoxyacetamido; n is 1 or 2 and each $R^2$ is independently hydrogen, fluoro, chloro, bromo, trifluoromethyl, nitro, cyano, methyl or ethyl; or a pharmaceutically-acceptable salt thereof.

6. A quinazoline derivative of the formula I as claimed in claim 1 and subject to the provisos stated in claim 1 wherein $(R^1)_m$ is 6-hydroxy, 7-hydroxy, 6,7-dihydroxy, 6-amino, 7-amino, 6-ureido, 6-trifluoromethoxy, 6-methyl, 6,7-dimethyl, 6-methoxy, 7-methoxy, 6,7-dimethoxy, 6,7-diethoxy, 6-hydroxy-7-methoxy, 7-hydroxy-6-methoxy, 6-amino-7-methoxy, 6-amino-7-methylthio, 5-amino-6,7-dimethoxy, 6-methoxy-7-isopropoxy, 6,7-methylenedioxy, 6,7-ethylenedioxy, 6-dimethylamino, 6-methoxymethyl, 6-(2-methoxyethoxymethyl), 6-cyanomethyl, 7-(2-hydroxyethoxy)-6-methoxy, 6,7-di-(2-hydroxyethoxy), 6-(2-methoxyethoxy), 6-methoxy-7-(2-methoxyethoxy), 6,7-di-(2-methoxyethoxy), 7-(2-bromoethoxy)-6-methoxy, 7-benzyloxy-6-methoxy, 6-(2-methoxyethylamino), 6-acetamido, 6-(2-chloroacetamido), 6-(2-methoxyacetamido) or 7-(2-methoxyacetamido); and $(R^2)_n$ is hydrogen, 4'-fluoro, 3'-chloro, 3'-bromo, 3',4'-dichloro, 4'-fluoro-3'-chloro, 3'-trifluoromethyl, 4'-fluoro-3'-trifluoromethyl, 3'-nitro, 3'-nitro-4'-chloro, 3'-nitro-4'-fluoro or 3'-methyl; or a pharmaceutically-acceptable acid-addition salt thereof.

7. A quinazoline derivative, or a pharmaceutically-acceptable acid-addition salt thereof, selected from: 4-(3,-chloro-4'-fluoroanilino)-6,7-dimethoxyquinazoline, 4-(3,,4,-dichloroanilino)-6,7-dimethoxyquinazoline, 6,7-dimethoxy-4-(3'-nitroanilino)quinazoline, 6,7-diethoxy-4-(3'-methylanilino)quinazoline, 6-methoxy-4-(3'-methylanilino)quinazoline, 4-(3,-chloroanilino)-6-methoxyquinazoline, 6,7-ethylenedioxy-4-(3'-methylanilino)quinazoline, 6-amino-7-methoxy-4-(3'-methylanilino)quinazoline, 4-(3'-methylanilino)-6-ureidoquinazoline and 6-(2-methoxyethoxymethyl)-4-(3'-methylanilino)quinazoline.

8. A quinazoline derivative of the formula I as claimed in claim 1 and subject to the provisos stated in claim 1 wherein $(R^1)_m$ is 6-hydroxy, 7-hydroxy, 6,7-dihydroxy, 6-amino, 7-amino, 6-ureido, 6-trifluoromethoxy, 6-methyl, 6,7-dimethyl, 6-methoxy, 7-methoxy, 6,7-dimethoxy, 6,7-diethoxy, 6-hydroxy-7-methoxy, 7-hydroxy-6-methoxy, 6-amino-7-methoxy, 6-amino-7-methylthio, 5-amino-6,7-dimethoxy, 6-methoxy-7-isopropoxy, 6,7-methylenedioxy, 6,7-ethylenedioxy, 6-methylamino, 7-methylamino, 6-dimethylamino, 6-amino-7-methylamino, 6-methoxymethyl, 6-bromomethyl, 6-(2-methoxyethoxymethyl), 6-cyanomethyl, 6-methylthiomethyl, 6-phenylthiomethyl, 7-(2-hydroxyethoxy)-6-methoxy, 6,7-di-(2-hydroxyethoxy), 6-(2-bromoethoxy), 6-(2-methoxyethoxy), 6-methoxy-7-(2-methoxyethoxy), 6,7-di-(2-methoxyethoxy), 7-(2-bromoethoxy)-6-methoxy, 7-benzyloxy-6-methoxy, 6-(2-methoxyethylamino), 6-acetamido, 6-benzamido, 6-(2-chloroacetamido), 6-(2-methoxyacetamido) or 7-(2-methoxyacetamido); and $(R^2)_n$ is hydrogen, 4'-fluoro, 3'-chloro, 3'-bromo, 3',4'-dichloro, 4'-fluoro-3'-chloro, 3'-trifluoromethyl, 4'-fluoro-3'-trifluoromethyl, 3'-nitro, 3'-nitro- 4'-chloro, 3'-nitro-4'-fluoro or 3'-methyl; or a pharmaceutically-acceptable acid-addition salt thereof.

9. A quinazoline derivative, or a pharmaceutically-acceptable acid-addition salt thereof, selected from: 6,7-di-(2-methoxyethoxy)-4-(3'-methylanilino)quinazoline, 6-dimethylamino-4-(3'-methylanilino)quinazoline and 6-benzamido-4-(3'-methylanilino)quinazoline.

10. A pharmaceutical composition which comprises a quinazoline derivative of the formula I

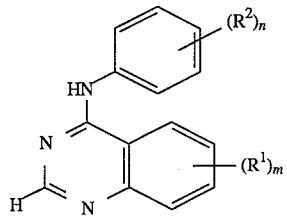

wherein m is 1, 2 or 3 and each R¹ is independently 6-hydroxy, 7-hydroxy, amino, carboxy, carbamoyl, ureido, (1-4C) alkoxycarbonyl, N-(1-4C) alkylcarbamoyl, N,N-di-[(1-4C)alkyl]carbamoyl, hydroxyamino, (1-4C)alkoxyamino, (2-4C)alkanoyloxyamino, trifluoromethoxy, (1-4C)alkyl, 6-(1-4C)alkoxy, 7-(1-4C)alkoxy, (1-3C)alkylenedioxy, (1-4C)alkylamino, di-[(1-4C)alkyl]amino, pyrrolidin-1-yl, piperidino, morpholino, piperazin-1-yl, 4-(1-4C)alkylpiperazin-1-yl, (1-4C)alkylthio, (1-4C)alkylsulphinyl, (1-4C)alkylsulphonyl, bromomethyl, dibromomethyl, hydroxy-(1-4C)alkyl, (2-4C)alkanoyloxy-(1-4C)alkyl, (1-4C)alkoxy-(1-4C)alkyl, carboxy-(1-4C)alkyl, (1-4C)alkoxycarbonyl-(1-4C)alkyl, carbamoyl-(1-4C)alkyl, N-(1-4C)alkylcarbamoyl-(1-4C)alkyl, N,N-di-[(1-4C)alkyl]carbamoyl-(1-4C)alkyl, amino-(1-4C)alkyl, (1-4C)alkylamino-(1-4C)alkyl, di-[(1-4C)alkyl]amino-(1-4C)alkyl, piperidino-(1-4C)alkyl, morpholino-(1-4C)alkyl, piperazin-1-yl-(1-4 C)alkyl, 4-(1-4C)alkylpiperazin-1-yl-(1-4C)alkyl, hydroxy-(2-4C)alkoxy-(1-4C)alkyl, (1-4C)alkoxy-(2-4C)alkoxy-( 1-4C)alkyl, hydroxy-(2-4C)alkylamino-(1-4C)alkyl, (1-4C)alkoxy-(2-4C)alkylamino-(1-4C)alkyl, (1-4C)alkylthio-( 1-4C)alkyl, hydroxy-(2-4C)alkylthio-(1-4C)alkyl, (1-4C)alkoxy-(2-4C)alkylthio-(1-4C)alkyl, phenoxy-(1-4C)alkyl, anilino-(1-4C)alkyl, phenylthio-(1-4C)alkyl, cyano-(1-4C)alkyl, halogeno-(2-4C)alkoxy, hydroxy-(2-4C)alkoxy, (2-4C)alkanoyloxy-(2-4C)alkoxy, (1-4C)alkoxy-(2-4C)alkoxy, carboxy-(1-4C)alkoxy, (1-4C)alkoxycarbonyl-(1-4C)alkoxy, carbamoyl-(1-4C)alkoxy, N-(1-4C)alkylcarbamoyl-(1-4C)alkoxy, N,N-di-[(1-4C)alkyl]carbamoyl-(1-4C)alkoxy, amino-(2-4C)alkoxy, (1-4C)alkylamino-(2-4C)alkoxy, di-[(1-4C)alkyl]amino-(2-4C)alkoxy, (2-4C)alkanoyloxy, hydroxy-(2-4C)alkanoyloxy, (1-4C)alkoxy-(2-4C)alkanoyloxy, phenyl-(1-4C)alkoxy, phenoxy-(2-4C)alkoxy, anilino-(2-4C)alkoxy, phenylthio-(2-4C)alkoxy, piperidino-(2-4C)alkoxy, morpholino-(2-4C)alkoxy, piperazin-1-yl-(2-4C)alkoxy, 4-(1-4C)alkylpiperazin-1-yl-(2-4C)alkoxy, halogeno-(2-4C)alkylamino, hydroxy-(2-4C)alkylamino, (2-4C)alkanoyloxy-(2-4C)alkylamino, (1-4C)alkoxy-(2-4C)alkylamino, carboxy-(1-4C)alkylamino, (1-4C)alkoxycarbonyl-(1-4C)alkylamino, carbamoyl-(1-4C)alkylamino, N-(1-4C)alkylcarbamoyl-(1-4C)alkylamino, N,N-di-[(1-4C)alkyl]carbamoyl-(1-4C)alkylamino, amino-(2-4C)alkylamino, (1-4C)alkylamino-(2-4C)alkylamino, di-1(1-4C)alkyl]amino-(2-4C)alkylamino, phenyl-(1-4C)alkylamino, phenoxy-(2-4C)alkylamino, anilino-(2-4C)alkylamino, phenylthio-(2-4C)alkylamino, (2-4C)alkanoylamino, (1-4C)alkoxycarbonylamino, (1-4C)alkylsulphonylamino, benzamido, benzenesulphonamido, 3-phenylureido, 2-oxopyrrolidin-1-yl, 2,5-dioxopyrrolidin-1-yl, halogeno-(2-4C)alkanoylamino, hydroxy-(2-4C)alkanoylamino, (1-4C)alkoxy-(2-4C)alkanoylamino, carboxy-(2-4C)alkanoylamino, (1-4C)alkoxycarbonyl-(2-4C)alkanoylamino, carbamoyl-(2-4C)alkanoylamino, N-(1-4C)alkylcarbamoyl-(2-4C)alkanoylamino, N,N-di-[(1-4C)alkyl]carbamoyl-(2-4C)alkanoylamino, amino-(2-4C)alkanoylamino, (1-4C)alkylamino-(2-4C)alkanoylamino or di-[(1-4C)alkyl]amino-(2-4C)alkanoylamino, and wherein said benzamido or benzenesulphonamido substituent or any anilino, phenoxy or phenyl group in a R¹ substituent may optionally bear one or two halogeno, (1-4C)alkyl or (1-4C)alkoxy substituents; n is 1 or 2 and each R² is independently hydrogen, hydroxy, halogeno, trifluoromethyl, amino, nitro, cyano, (1-4C)alkyl, (1-4C)alkoxy, (1-4C)alkylamino, di-[(1-4C)alkyl]amino, (1-4C)alkylthio, (1-4C)alkylsulphinyl or (1-4C)alkylsulphonyl; or a pharmaceutically-acceptable salt thereof; except that 4-anilino-6,7-dimethoxyquinazoline or the hydrochloride salt thereof are excluded.

11. A pharmaceutical composition which comprises a quinazoline derivative of the formula I

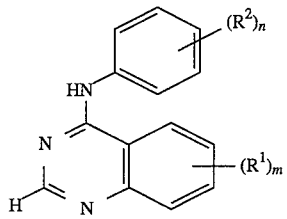

wherein m is 1, 2 or 3 and each R¹ is independently 6-hydroxy, 7 -hydroxy, amino, carboxy, carbamoyl, ureido, (1-4C)alkoxycarbonyl, N-(1-4C)alkylcarbamoyl, N,N-di-[(1-4C)alkyl]carbamoyl, hydroxyamino, (1-4C)alkoxyamino, (2-4C)alkanoyloxyamino, trifluoromethoxy, (1-4C)alkyl, 6-(1-4C)alkoxy, 7-(1-4C)alkoxy, (1-3C)alkylenedioxy, (1-4C)alkylamino, di-[(1-4C) alkyl]amino, pyrrolidin-1-yl, piperidino, morpholino, piperazin-1-yl, 4-(1-4C)alkylpiperazin-1-yl, (1-4C)alkylthio, (1-4C)alkylsulphinyl, (1-4C)alkylsulphonyl, bromomethyl, dibromomethyl, hydroxy-(1-4C)alkyl, (2-4C)alkanoyloxy-(1-4C)alkyl, (1-4C)alkoxy-(1-4C)alkyl, carboxy-(1-4C)alkyl, (1-4C)alkoxycarbonyl-(1-4C)alkyl, carbamoyl-(1-4C)alkyl, N-(1-4C)alkylcarbamoyl-(1-4C)alkyl, N,N-di-[(1-4C)alkyl]carbamoyl-(1-4C)alkyl, amino-(1-4C)alkyl, (1-4C)alkylamino-(1-4C)alkyl, di-[(1-4C)alkyl]amino-(1-4C)alkyl, piperidino-(1-4C)alkyl, morpholino-(1-4C)alkyl, piperazin-1-yl-(1-4C)alkyl, 4-(1-4C)alkylpiperazin-1-yl-(1-4C)alkyl, hydroxy-(2-4C)alkoxy-(1-4C)alkyl, (1-4C)alkoxy-(2-4C)alkoxy-( 1-4C)alkyl, hydroxy-(2-4C)alkylamino-(1-4C)alkyl, (1-4C)alkoxy-(2-4C)alkylamino-(1-4C)alkyl, (1-4C)alkylthio-( 1-4C)alkyl, hydroxy-(2-4C)alkylthio-(1-4C)alkyl, (1-4C)alkoxy-(2-4C)alkylthio-(1-4C)alkyl, phenoxy-(1-4C)alkyl, anilino-(1-4C)alkyl, phenylthio-(1-4C)alkyl, cyano-(1-4C)alkyl, halogeno-(2-4C)alkoxy, hydroxy-(2-4C)alkoxy, (2-4C)alkanoyloxy-(2-4C)alkoxy, (1-4C)alkoxy-(2-4C)alkoxy, carboxy-(1-4C)alkoxy, (1-4C)alkoxycarbonyl-(1-4C)alkoxy, carbamoyl-(1-4C)alkoxy, N-(1-4C)alkylcarbamoyl-(1-4C)alkoxy, N,N-di-[(1-4C)alkyl]carbamoyl-(1-4C)alkoxy, amino-(2-4C)alkoxy, (1-4C)alkylamino-(2-4C)alkoxy, di-[(1-4C)alkyl]amino-(2-4C)alkoxy, (2-4C)alkanoyloxy, hydroxy-(2-4C)alkanoyloxy, (1-4C)alkoxy-(2-4C)alkanoyloxy, phenyl-(1-4C)alkoxy, phenoxy-(2-4C)alkoxy, anilino- (2-4C)alkoxy, phenylthio-(2-4C)alkoxy, piperidino-(2-4C)alkoxy, morpholino-(2-4C)alkoxy, piperazin-1-yl-(2-4C)alkoxy, 4-(1-4C)alkylpiperazin-1-yl-(2 -4C)alkoxy, halogeno-(2-4C)alkylamino, hydroxy-(2-4C)alkylamino, (2-4C)alkanoyloxy-(2-4C)alkylamino, (1-4C)alkoxy-(2-4C)alkylamino, carboxy-(1-4C)alkylamino, (1-4C)alkoxycarbonyl-(1-4C)alkylamino, carbamoyl-(1-4C)alkylamino, N-(1-4C)alkylcarbamoyl-(1-4C)alkylamino, N,N-di-[(1-4C)alkyl]carbamoyl -(1-4C)alkylamino, amino-(2-4C)alkylamino, (1-4C)alkylamino-(2-4C)alkylamino, di-1(1-4C)alkyl]amino-(2-4C)alkylamino, phenyl-(1-4C)alkylamino, phenoxy-(2-4C)alkylamino, anilino-(2-4C)alkylamino, phenylthio-(2-4C)alkylamino, (2-4C)alkanoylamino, (1-4C)alkoxycarbonylamino, (1-4C)alkylsulphonylamino, benzamido, benzenesulphonamido, 3-phenylureido, 2-oxopyrrolidin-1-yl, 2,5-dioxopyrrolidin-1-yl, halogeno-(2-4C)alkanoylamino, hydroxy-(2-4C)alkanoylamino, (1-4C)alkoxy-(2-4C)alkanoylamino, carboxy-(2-4C)alkanoylamino, (1-4C)alkoxycarbonyl-(2-4C)alkanoylamino, carbamoyl-( 2-4C)alkanoylamino, N-(1-4C)alkylcarbamoyl-(2-4C)alkanoylamino, N,N-di-[(1-4C)alkyl]carbamoyl-(2-4C)alkanoylamino, amino-(2-4C)alkanoylamino, (1-4C)alkylamino-(2-4C)alkanoylamino or di-1(1-4C)alkyl]amino-(2-4C)alkanoylamino, and wherein said benzamido or benzenesulphonamido substituent or any anilino, phenoxy or phenyl group in a $R^1$ substituent may optionally bear one or two halogeno, (1-4C)alkyl or (1-4C)alkoxy substituents; n is 1 or 2 and each $R^2$ is independently hydrogen, hydroxy, halogeno, trifluoromethyl, amino, nitro, cyano, (1-4C)alkyl, (1-4C)alkoxy, (1-4C)alkylamino, di-[(1-4C)alkyl]amino, (1-4C)alkylthio, (1-4C)alkylsulphinyl, (1-4C)alkylsulphonyl, (2-4C)alkanoylamino, (2-4C)alkanoyl, or benzamido, wherein said benzamido group may optionally bear one or two halogeno, (1-4C)alkyl or (1-4C)alkoxy substituents; or a pharmaceutically-acceptable salt thereof; except that 4-anilino-6,7-dimethoxyquinazoline or the hydrochloride salt thereof are excluded.

12. A method for producing an anti-cancer effect in a warm-blooded animal in need of such treatment which comprises administering to said animal an effective amount of a quinazoline derivative of the formula I

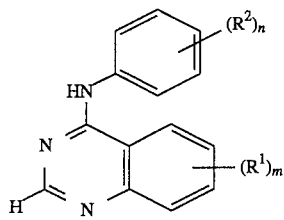

wherein m is 1, 2 or 3 and each $R^1$ is independently 6-hydroxy, 7-hydroxy, amino, carboxy, carbamoyl, ureido, (1-4C)alkoxycarbonyl, N-(1-4C)alkylcarbamoyl, N,N-di-[(1-4C)alkyl]carbamoyl, hydroxyamino, (1-4C)alkoxyamino, (2-4C)alkanoyloxyamino, trifluoromethoxy, (1-4C)alkyl, 6-(1-4C)alkoxy, 7-(1-4C)alkoxy, (1-3C)alkylenedioxy, (1-4C)alkylamino, di-[(1-4C)alkyl]amino, pyrrolidin-1-yl, piperidino, morpholino, piperazin-1-yl, 4-(1-4C)alkylpiperazin-1-yl, (1-4C)alkylthio, (1-4C)alkylsulphinyl, (1-4C)alkylsulphonyl, bromomethyl, dibromomethyl, hydroxy-(1-4C)alkyl, (2-4C)alkanoyloxy-(1-4C)alkyl, (1-4C)alkoxy-(1-4C)alkyl, carboxy-(1-4C)alkyl, (1-4C)alkoxycarbonyl-(1-4C)alkyl, carbamoyl-(1-4C)alkyl, N-(1-4C)alkylcarbamoyl-(1-4C)alkyl, N,N-di-[(1-4C)alkyl]carbamoyl-(1-4C)alkyl, amino-(1-4C)alkyl, (1-4C)alkylamino-(1-4C)alkyl, di-[(1-4C)alkyl]amino-(1-4C)alkyl, piperidino-(1-4C)alkyl, morpholino-(1-4C)alkyl, piperazin-1-yl-(1-4C)alkyl, 4-(1-4C)alkylpiperazin-1-yl-(1-4C)alkyl, hydroxy-(2-4C)alkoxy-(1-4C)alkyl, (1-4C)alkoxy-(2-4C)alkoxy-( 1-4C) alkyl, hydroxy-(2-4C)alkylamino-(1-4C)alkyl, (1-4C)alkoxy-(2-4C)alkylamino-(1-4C)alkyl, (1-4C)alkylthio-( 1-4C)alkyl, hydroxy-(2 -4C)alkylthio-(1-4C)alkyl, (1-4C)alkoxy-(2-4C)alkylthio-(1-4C)alkyl, phenoxy-(1-4C)alkyl, anilino-(1-4C)alkyl, phenylthio-(1-4C)alkyl, cyano-(1-4C)alkyl, halogeno-(2-4C)alkoxy, hydroxy-(2-4C)alkoxy, (2-4C)alkanoyloxy-(2-4C)alkoxy, (1-4C)alkoxy-(2-4C)alkoxy, carboxy-(1-4C)alkoxy, (1-4C)alkoxycarbonyl-(1-4C)alkoxy, carbamoyl-(1-4C)alkoxy, N-(1-4C)alkylcarbamoyl-(1-4C)alkoxy, N,N-di-[(1-4C)alkyl]carbamoyl-(1-4C)alkoxy, amino-(2-4C)alkoxy, (1-4C)alkylamino-(2-4C)alkoxy, di-[(1-4C)alkyl]amino-(2-4C)alkoxy, (2-4C)alkanoyloxy, hydroxy-(2-4C)alkanoyloxy, (1-4C)alkoxy-(2-4C)alkanoyloxy, phenyl-(1-4C)alkoxy, phenoxy-(2-4C)alkoxy, anilino-(2-4C)alkoxy, phenylthio-(2-4C)alkoxy, piperidino-(2-4C)alkoxy, morpholino-(2-4C)alkoxy, piperazin-1-yl-(2-4C)alkoxy, 4-(1-4C)alkylpiperazin-1-yl-(2-4C)alkoxy, halogeno-(2-4C)alkylamino, hydroxy-(2-4C)alkylamino, (2-4C)alkanoyloxy-(2-4C)alkylamino, (1-4C)alkoxy-(2-4C)alkylamino, carboxy-(1-4C)alkylamino, (1-4C)alkoxycarbonyl-(1-4C)alkylamino, carbamoyl-( 1-4C )alkylamino, N-(1-4C)alkylcarbamoyl-(1-4C)alkylamino, N,N-di-[(1-4C)alkyl]carbamoyl-(1-4C)alkylamino, amino-(2-4C)alkylamino, (1-4C)alkylamino-(2-4C)alkylamino, di-[(1-4C)alkyl]amino-(2-4C)alkylamino, phenyl-(1-4C)alkylamino, phenoxy-(2-4C)alkylamino, anilino-(2-4C)alkylamino, phenylthio-(2-4C)alkylamino, (2-4C)alkanoylamino, (1-4C)alkoxycarbonylamino, (1-4C)alkylsulphonylamino, benzamido, benzenesulphonamido, 3-phenylureido, 2-oxopyrrolidin-1-yl, 2,5-dioxopyrrolidin-1-yl, halogeno-(2-4C)alkanoylamino, hydroxy-(2-4C)alkanoylamino, (1-4C)alkoxy-(2-4C)alkanoylamino, carboxy-(2-4C)alkanoylamino, (1-4C)alkoxycarbonyl-(2-4C)alkanoylamino, carbamoyl-(2-4C)alkanoylamino, N-(1-4C)alkylcarbamoyl-(2-4C)alkanoylamino, N,N-di-[(1-4C)alkyl]carbamoyl-(2-4C)alkanoylamino, amino-(2-4C)alkanoylamino, (1-4C)alkylamino-(2-4C)alkanoylamino or di-1(1-4C)alkyl]amino-(2-4C)alkanoylamino, and wherein said benzamido or benzenesulphonamido substituent or any anilino, phenoxy or phenyl group in a $R^1$ substituent may optionally bear one or two halogeno, (1-4C)alkyl or (1-4C)alkoxy substituents; n is 1 or 2 and each $R^2$ is independently hydrogen, hydroxy, halogeno, trifluoromethyl, amino, nitro, cyano, (1-4C)alkyl, (1-4C)alkoxy, (1-4C)alkylamino, di-[(1-4C)alkyl]amino, (1-4C)alkylthio, (1-4C)alkylsulphinyl, (1-4C)alkylsulphonyl, (2-4C)alkanoylamino, (2-4C)alkanoyl, or benzamido, wherein said benzamido group may optionally bear one or two halogeno, (1-4C) alkyl or (1-4C)alkoxy substituents; or a pharmaceutically-acceptable salt thereof.

13. A quinazoline derivative, or a pharmaceutically-acceptable acid-addition salt thereof, selected from:
6,7-dimethoxy-4-(3'-trifluoromethylanilino)quinazoline,
6-hydroxy-7-methoxy-4-(3'-methylanilino)quinazoline, 7-hydroxy-6-methoxy-4-(3'-methylanilino)quinazoline, 7-amino-4-(3'-methylanilino)quinazoline, 6-amino-4-(3'-methylanilino)quinazoline, 6-amino-4-(3'-chloroanilino)quinazoline, 6-acetamido-4-(3'-methylanilino)quinazoline, 6-(2-methoxyethylamino)-4-(3'-methylanilino)quinazoline, 7-(2-methoxyacetamido)-4-(3'-methylanilino)quinazoline, 7-(2-hydroxyethoxy)-6-methoxy-4-(3'- methylanilino)quinazoline and 7-(2-methoxyethoxy)-6-methoxy-4-(3'-methylanilino)quinazoline.

14. The quinazoline derivative, or pharmaceutically-acceptable acid-addition salt thereof, as claimed in claim 13, being:

6-amino-4-(3'-methylanilino)quinazoline.

15. A method for producing an anti-cancer effect in a warm-blooded animal having a receptor tyrosine kinase sensitive cancer which comprises administering to said animal an effective amount of a quinazoline derivative of the formula I, or a pharmaceutically-acceptable salt thereof, as claimed in any one of claims 1, 13 or 14, or a quinazoline derivative selected from 4-(4'-hydroxyanilino)-6-methoxyquinazoline, 4-(4'-hydroxyanilino)-6,7-methylenedioxyquinazoline, 4-(4'-hydroxyanilino)-6,7,8-trimethoxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof.

16. A method for producing an anti-cancer effect in a warm-blooded animal having a receptor tyrosine kinase sensitive cancer selected from leukemia, breast, lung, colon, rectal, stomach, prostate, bladder, pancreatic and ovarian cancer, which comprises administering to said animal an effective amount of a quinazoline derivative of the formula I, or a pharmaceutically-acceptable salt thereof, as claimed in any one of claims 1, 13 or 14, or a quinazoline derivative selected from 4-(4'-hydroxyanilino)-6-methoxyquinazoline, 4-(4'-hydroxyanilino)-6,7-methylenedioxyquinazoline, 4-(4'-hydroxyanilino)-6,7,8-trimethoxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof.

17. A method for producing an anti-proliferative effect in a warm-blooded animal in need of such treatment which comprises administering to said animal an effective amount of a quinazoline derivative of the formula I, or a pharmaceutically-acceptable salt thereof, as claimed in any one of claims 1, 13 or 14, or a quinazoline derivative selected from 4-(4,-hydroxyanilino)-6-methoxyquinazoline, 4-(4,-hydroxyanilino)-6,7-methylenedioxyquinazoline, 4-(4,-hydroxyanilino)-6,7,8-trimethoxyquinazoline, 6-amino-4-(4'aminoanilino)quinazoline, 4-anilino-6-methylquinazoline or the hydrochloride salt thereof and 4-anilino-6,7-dimethoxvauinazoline or the hydrochloride salt thereof.

18. A method for producing an anti-proliferative effect mediated alone or in part by inhibition of the enzyme receptor tyrosine kinase in a warm-blooded animal which comprises administering to said animal an effective amount of a quinazoline derivative of the formula I, or a pharmaceutically-acceptable salt thereof, as claimed in any one of claims 1, 13 or 14, or a quinazoline derivative selected from 4-(4'-hydroxyanilino)-6-methoxyquinazoline, 4-(4'-hydroxyanilino)-6,7-methylenedioxyquinazoline, 4-(4'-hydroxyanilino)-6,7,8-trimethoxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof.

19. A method for treating the proliferation of malignant cells characterized by inhibition of the enzyme receptor tyrosine kinase which comprises administering an effective amount of a quinazoline derivative of the formula I, or a pharmaceutically-acceptable salt thereof, as claimed in any one of claims 1, 13 or 14, or a quinazoline derivative selected from 4-(4'-hydroxyanilino)-6-methoxyquinazoline, 4-(4'-hydroxyanilino)-6,7-methylenedioxyquinazoline, 4-(4'-hydroxyanilino)-6,7,8-trimethoxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof.

20. A method for producing a receptor tyrosine kinase inhibitory effect in a warm-blooded animal in need of such treatment which comprises administering to said animal an effective amount of a quinazoline derivative of the formula I, or a pharmaceutically-acceptable salt thereof, as claimed in any one of claims 1, 13 or 14, or a quinazoline derivative selected from 4-(4'-hydroxyanilino)-6-methoxyquinazoline, 4-(4'-hydroxyanilino)-6,7-methylenedioxyquinazoline, 4-(4'-hydroxyanilino)-6,7,8-trimethoxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof.

21. A method for treating in a warm-blooded animal a disease or medical condition mediated alone or in part by the enzyme receptor tyrosine kinase which comprises administering to said animal an effective amount of a quinazoline derivative of the formula I, or a pharmaceutically-acceptable salt thereof, as claimed in any one of claims 1, 3 or 14, or a quinazoline derivative selected from 4-(4'-hydroxyanilino)-6-methoxyquinazoline, 4-(4'-hydroxyanilino)-6,7-methylenedioxyquinazoline, 4-(4'-hydroxyanilino)-6,7,8-trimethoxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof.

22. A method for producing an anti-cancer effect in a warm-blooded animal in need of such treatment which comprises administering to said animal an effective amount of a quinazoline derivative of the formula I

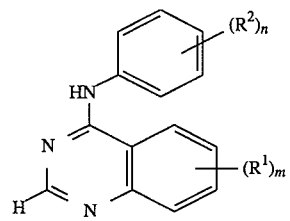

wherein m is 1, 2 or 3 and each $R^1$ is independently 6-hydroxy, 7-hydroxy, amino, carboxy, carbamoyl, ureido, (1-4C)alkoxycarbonyl, N-(1-4C)alkylcarbamoyl, N,N-di-[(1-4C)alkyl]carbamoyl, hydroxyamino, (1-4C)alkoxyamino, (2-4C)alkanoyloxyamino, trifluoromethoxy, (1-4C)alkyl, 6-(1-4C)alkoxy, 7-(1-4C)alkoxy, (1-3C)alkylenedioxy, (1-4C)alkylamino, di-[(1-4C)alkyl]amino, pyrrolidin-1-yl, piperidino, morpholino, piperazin-1-yl, 4-(1-4C)alkylpiperazin-1-yl, (1-4C)alkylthio, (1-4C)alkylsulphinyl, (1-4C)alkylsulphonyl, bromomethyl, dibromomethyl, hydroxy-(1-4C)alkyl, (2-4C)alkanoyloxy-(1-4C)alkyl, (1-4C)alkoxy-(1-4C)alkyl, carboxy-(1-4C)alkyl, (1-4C)alkoxycarbonyl-(1-4C)alkyl, carbamoyl-(1-4C)alkyl, N-(1-4C)alkylcarbamoyl-(1-4C)alkyl, N, N-di-[(1-4C)alkyl]carbamoyl-(1-4C)alkyl, amino-(1-4C)alkyl, (1-4C)alkylamino-(1-4C)alkyl, di-[(1-4C)alkyl]amino-(1-4C)alkyl, piperidino-(1-4C)alkyl, morpholino-(1-4C)alkyl, piperazin-1-yl-(1-4C)alkyl, 4-(1-4C)alkylpiperazin-1-yl-(1-4C)alkyl, hydroxy-(2-4C)alkoxy-(1-4C)alkyl, (1-4C)alkoxy-(2-4C)alkoxy-( 1-4C)alkyl, hydroxy-(2-4C) alkylamino-(1-4C) alkyl, (1-4C)alkoxy-(2-4C)alkylamino-(1-4C)alkyl, (1-4C)alkylthio-( 1-4C) alkyl, hydroxy-(2-

4C)alkylthio-(1-4C)alkyl, (1-4C) alkoxy-(2-4C)alkylthio-(1-4C)alkyl, phenoxy-(1-4C)alkyl, anilino-(1-4C)alkyl, phenylthio-(1-4C)alkyl, cyano-(1-4C)alkyl, halogeno-(2-4C)alkoxy, hydroxy-(2-4C)alkoxy, (2-4C)alkanoyloxy-(2-4C)alkoxy, (1-4C) alkoxy-(2-4C) alkoxy, carboxy-(1-4C)alkoxy, (1-4C)alkoxycarbonyl-(1-4C)alkoxy, carbamoyl-(1-4C)alkoxy, N-(1-4C)alkylcarbamoyl-(1-4C)alkoxy, N,N-di-[(1-4C)alkyl]carbamoyl-(1-4C)alkoxy, amino-(2-4C)alkoxy, (1-4C)alkylamino-(2-4C)alkoxy, di-[(1-4C)alkyl]amino-(2-4C)alkoxy, (2-4C)alkanoyloxy, hydroxy-(2-4C)alkanoyloxy, (1-4C)alkoxy-(2-4C)alkanoyloxy, phenyl-(1-4C)alkoxy, phenoxy-(2-4C)alkoxy, anilino-(2-4C)alkoxy, phenylthio-(2-4C)alkoxy, piperidino-(2-4C)alkoxy, morpholino-(2-4C)alkoxy, piperazin-1-yl-(2-4C)alkoxy, 4-(1-4C)alkylpiperazin-1-yl-(2-4C)alkoxy, halogeno-(2-4C)alkylamino, hydroxy-(2-4C)alkylamino, (2-4C)alkanoyloxy-(2-4C)alkylamino, (1-4C)alkoxy-(2-4C)alkylamino, carboxy-(1-4C)alkylamino, (1-4C)alkoxycarbonyl-(1-4C)alkylamino, carbamoyl-(1-4C)alkylamino, N-(1-4C)alkylcarbamoyl-(1-4C)alkylamino, N,N-di-[(1-4C)alkyl]carbamoyl-(1-4C)alkylamino, amino-(2-4C)alkylamino, (1-4C)alkylamino-(2-4C)alkylamino, di-[(1-4C)alkyl]amino-(2-4C)alkylamino, phenyl-(1-4C)alkylamino, phenoxy-(2-4C)alkylamino, anilino-(2-4C)alkylamino, phenylthio-(2-4C)alkylamino, (2-4C)alkanoylamino, (1-4C)alkoxycarbonylamino, (1-4C)alkylsulphonylamino, benzamido, benzenesulphonamido, 3-phenylureido, 2-oxopyrrolidin-1-yl, 2,5-dioxopyrrolidin-1-yl, halogeno-(2-4C)alkanoylamino, hydroxy-(2-4C)alkanoylamino, (1-4C)alkoxy-(2-4C)alkanoylamino, carboxy-(2-4C)alkanoylamino, (1-4C)alkoxycarbonyl-(2-4C)alkanoylamino, carbamoyl-(2-4C)alkanoylamino, N-(1-4C)alkylcarbamoyl-(2-4C)alkanoylamino, N,N-di-[(1-4C)alkyl]carbamoyl-(2-4C)alkanoylamino, amino-(2-4C)alkanoylamino, (1-4C)alkylamino-(2-4C)alkanoylamino or di-[(1-4C)alkyl]amino-(2-4C)alkanoylamino, and wherein said benzamido or benzenesulphonamido substituent or any anilino, phenoxy or phenyl group in a $R^1$ substituent may optionally bear one or two halogeno, (1-4C)alkyl or (1-4C)alkoxy substituents; n is 1 or 2 and each $R^2$ is independently hydrogen, hydroxy, halogeno, trifluoromethyl, amino, nitro, cyano, (1-4C)alkyl, (1-4C)alkoxy, (1-4C)alkylamino, di-[(1-4C)alkyl]amino, (1-4C)alkylthio, (1-4C)alkylsulphinyl, (1-4C)alkylsulphonyl, (2-4C)alkanoylamino, (2-4C)alkanoyl, or benzamido, wherein said benzamido group may optionally bear one or two halogeno, (1-4C)alkyl or (1-4C)alkoxy substituents; or a pharmaceutically-acceptable salt thereof.

23. A method for producing an anti-cancer effect in a warm-blooded animal in need of such treatment which comprises administering to said animal an effective amount of the quinazoline derivative 6-amino-4-(3'-methylamino-)quinazoline, or a pharmaceutically-acceptable salt thereof.

24. A method for producing an anti-cancer effect in a warm-blooded animal in need of such treatment which comprises administering to said animal an effective amount of the quinazoline derivative 6-acetamido-4-(3'-methylanilino) quinazoline, or a pharmaceutically-acceptable salt thereof.

25. A method for producing an anti-cancer effect in a warm-blooded animal in need of such treatment which comprises administering to said animal an effective amount of the quinazoline derivative 6-(2-methoxyethylamino))-4-(3'methylanilino)quinazoline, or a pharmaceutically-acceptable salt thereof.

26. A method for producing an anti-cancer effect in a warm-blooded animal in need of such treatment which comprises administering to said animal an effective amount of the quinazoline derivative 6-methoxy-7-(2-methoxyethoxy)-4-(3'-methylanilino)quinazoline, or a pharmaceutically-acceptable salt thereof.

27. A method for producing an anti-cancer effect in a warm-blooded animal in need of such treatment which comprises administering to said animal an effective amount of the quinazoline derivative 4-(3'-chloro-4'-fluoroanilino)-6,7-dimethoxyquinazoline, or a pharmaceutically-acceptable salt thereof.

28. A method for producing an anti-cancer effect in a warm-blooded animal in need of such treatment which comprises administering to said animal an effective amount of the quinazoline derivative 6-(2-chloroacetamido)-4-(3'-methylanilino)quinazoline, or a pharmaceutically-acceptable salt thereof.

29. A method for producing an anti-cancer effect in a warm-blooded animal in need of such treatment which comprises administering to said animal an effective amount of the quinazoline derivative 6-methylamino-4-(3'-methylanilino) quinazoline, or a pharmaceutically-acceptable salt thereof.

* * * * *

UNITED STATES PATENT AND TRADEMARK OFFICE
CERTIFICATE OF CORRECTION

PATENT NO. : 5,457,105
DATED : October 10, 1995
INVENTOR(S) : BARKER

It is certified that error appears in the above-indentified patent and that said Letters Patent is hereby corrected as shown below:

Column 62, line 51 (claim 12), after
"(1-4C)alkylsulphinyl" delete "," and insert --or--.

Column 62, lines 52-54 (claim 12), delete
", (2-4C)alkanoylamino, (2-4C)alkanoyl, or benzamido, wherein said benzamido group may optionally bear one or two halogeno, (1-4C)alkyl or (1-4C)alkoxy substituents".

Signed and Sealed this

Eighteenth Day of August, 1998

Attest:

BRUCE LEHMAN

*Attesting Officer*   *Commissioner of Patents and Trademarks*